(12) United States Patent
Capelli et al.

(10) Patent No.: US 7,279,474 B2
(45) Date of Patent: Oct. 9, 2007

(54) SUBSTITUTED PYRROLO[2,3-D]PYRIMIDINES AS ANTAGONISTS OF THE CORTICOTROPIN RELEASING FACTOR (CRF)

(75) Inventors: Anna Maria Capelli, Verona (IT); Chiara Marchionni, Verona (IT); Fabrizio Micheli, Verona (IT); Alessandra Pasquarello, Verona (IT); Benedetta Perini, Verona (IT); Yves St-Denis, Verona (IT); Romano Di Fabio, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 406 days.

(21) Appl. No.: 10/476,368

(22) PCT Filed: Apr. 30, 2002

(86) PCT No.: PCT/GB02/02029

§ 371 (c)(1),
(2), (4) Date: Apr. 16, 2004

(87) PCT Pub. No.: WO02/088095

PCT Pub. Date: Nov. 7, 2002

(65) Prior Publication Data

US 2004/0176400 A1    Sep. 9, 2004

(30) Foreign Application Priority Data

| Apr. 30, 2001 | (GB) | 0110567.5 |
| Apr. 30, 2001 | (GB) | 0110569.1 |
| Apr. 30, 2001 | (GB) | 0110570.9 |
| Jul. 17, 2001 | (GB) | 0117399.6 |
| Jul. 17, 2001 | (GB) | 0117401.0 |
| Jul. 17, 2001 | (GB) | 0117420.0 |
| Feb. 11, 2002 | (GB) | 0203201.9 |
| Mar. 22, 2002 | (GB) | 0206834.4 |

(51) Int. Cl.
| A61K 31/5355 | (2006.01) |
| A61K 31/519  | (2006.01) |
| C07D 487/04  | (2006.01) |
| C07D 413/14  | (2006.01) |
| A61P 25/24   | (2006.01) |
| A61P 25/22   | (2006.01) |

(52) U.S. Cl. ............. 514/234.2; 544/280; 544/117; 514/265.1

(58) Field of Classification Search ......... 544/280; 514/265.1

See application file for complete search history.

(56) References Cited

U.S. PATENT DOCUMENTS 5,962,479 A * 10/1999 Chen .................. 514/348

FOREIGN PATENT DOCUMENTS

| EP | 482804 A1    | 4/1992  |
| EP | 773023 A1    | 5/1997  |
| EP | 1040831 A2   | 10/2000 |
| EP | 1059100 A2   | 12/2000 |
| EP | 1 082 960    | 3/2001  |
| EP | 1 097 709    | 5/2001  |
| EP | 1 149 583    | 10/2001 |
| JP | 2000038350 A2| 2/2000  |
| WO | WO 95/33750  | 12/1995 |
| WO | WO98/08846 A1| 3/1998  |
| WO | WO 01/19829 A2| 3/2001 |
| WO | WO 01/23389 A2| 4/2001 |

OTHER PUBLICATIONS

Ayala, A.R.; Exp. Opin. Ther. Patents; 2000; 10(1); 67-74.*
Larsen et al. *Perkin*, 1(18): 3035-3038 (2000).
Afaf Elbanany. *J. Chem. Soc. Pak.*, 9(4): 547-550 (1987).
McCarthy, et al., Current Pharm. Design, 1999, vol. 5, No. 5, pp. 289-315.
Christos, et al., Expert Opinion on Ther. Patents, 1998, vol. 8, No. 2, pp. 143-152.

* cited by examiner

*Primary Examiner*—Mark L. Berch
*Assistant Examiner*—Susanna Moore
(74) *Attorney, Agent, or Firm*—Laura K. Madden; Loretta J. Sauermelon; Mary E. McCarthy

(57) ABSTRACT

The present invention provides compounds of formula (I) including stereoisomers, prodrugs and pharmaceutically acceptable salts or solvates thereof wherein the variables are as defined in the description, processes for their preparation, pharmaceutical compositions containing them and their use in the treatment of conditions mediated by corticotropin-releasing factor (CRF)

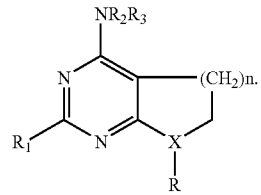

12 Claims, No Drawings

SUBSTITUTED PYRROLO[2,3-D]PYRIMIDINES AS ANTAGONISTS OF THE CORTICOTROPIN RELEASING FACTOR (CRF)

The present invention relates to bicyclic derivatives, to processes for their preparation, to pharmaceutical compositions containing them and to their use in therapy.

The first corticotropin-releasing factor (CRF) was isolated from ovine hypothalami and identified as a 41-amino acid peptide (Vale et al., Science 213: 1394-1397,1981).

CRF has been found to produce profound alterations in endocrine, nimbus and immune system function. CRF is believed to be the major physiological regulator of the basal and stress-release of adrenocorticotropic hormone ("ACTH"), Bendorphin and other proopiomelanocortin ("POMC")-derived peptides from the anterior pituitary (Vale et al., Science 213: 1394-1397,1981).

In addition to its role in stimulating the production of ACTH and POMC, CRF appears to be one of the pivotal central nervous system neurotransmitters and plays a crucial role in integrating the body's overall response to stress.

Administration of CRF directly to the brain elicits behavioral, physiological and endocrine responses identical to those observed for an animal exposed to a stressful environment.

Accordingly, clinical data suggests that CRF receptor antagonists may represent novel antidepressant and/or anxiolytic drugs that may be useful in the treatment of the neuropsychiatric disorders manifesting hypersecretion of CRF.

The first CRF receptor antagonists were peptides (see, e.g., Rivier et al., U.S. Pat. No. 4,605,642; Rivier et al., Science 224: 889,1984). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported.

WO 95/10506 describes inter alia compounds of general formula (A) with general CRF antagonist activity

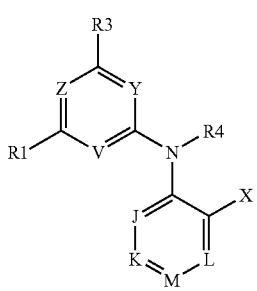

wherein Y may be CR29; V and Z may be nitrogen and carbon, R3 may correspond to an amine derivative and R4 may be taken together with R29 to form a 5-membered ring and is—CH(R28) when R29 is—CH(R30). There are no specific disclosures of compounds corresponding to this definition.

WO 95/33750 also describes compounds of general formula (B) having CRF antagonistic activity,

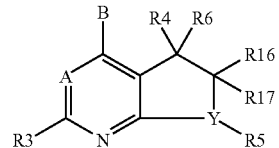

in which A and Y may be nitrogen and carbon and B may correspond to an amine derivative.

The compounds comprised in general formula (B), whose preparation is included in the Experimental Part of WO 95/33750, are characterized by having always at least one substituent other than hydrogen on the atoms different from Y in the 5-membered ring, when saturated.

WO 98/08846 describes compounds of general formula (C) having CRF antagonistic activity,

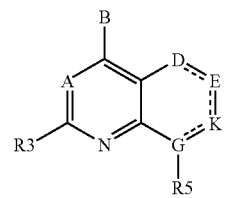

wherein A may be nitrogen, G may be nitrogen or carbon, B may be an amino derivative and the other groups have the meanings as defined.

The compounds comprised in general formula (C), in which A may be nitrogen and B may be an amino derivative, whose preparation is included in the Experimental Part WO 98/08846, are characterized by having always at least a substituent other than hydrogen on the atoms different from G in the 6-membered ring, when saturated.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

In particular the invention relates to novel compounds which are potent and specific antagonists of corticotropin-releasing factor (CRF) receptors.

The present invention provides compounds of formula (I) including stereoisomers, prodrugs and pharmaceutically acceptable salts or solvates thereof

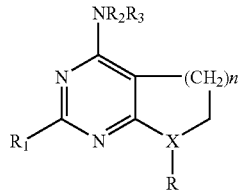

wherein
- R is aryl or heteroaryl, each of which may be substituted by 1 to 4 groups selected from:
  halogen, C1-C6 alkyl, C1-C6 alkoxy, halo C1-C6 alkyl, C2-C6 alkenyl, C2-C6 alkynyl, halo C1-C6 alkoxy, —$COR_4$, nitro, —$NR_9R_{10}$ cyano, and a group $R_5$;
- $R_1$ is hydrogen, C1-C6 alkyl, C2-C6 alkenyl, C2-C6 alkynyl, halo C1-C6 alkyl, halo C1-C6 alkoxy, halogen, $NR_9R_{10}$ or cyano;
- $R_2$ is hydrogen, C3-C7 cycloalkyl, or a group $R_6$;
- $R_3$ has the same meanings as $R_2$, but $R_2$ and $R_3$ may not be simultaneously hydrogen; or
- $R_2$ and $R_3$ together with N form a saturated or unsaturated heterocycle, which may be substituted by 1 to 3 $R_7$ groups; or
- $R_2$ and $R_3$ together with N form a 5-10 membered heteroaryl group, in which the 5-membered heteroaryl group contains at least one heteroatom selected from oxygen, sulphur or nitrogen and the 6-10 membered heteroaryl group contains from 1 to 3 nitrogen atoms and wherein said 5-10 membered heteroaryl may be substituted by 1 to 3 $R_7$ groups;
- $R_4$ is a C1-C4 alkyl, —$OR_9$ or —$NR_9R_{10}$;
- $R_5$ is a 5-6 membered heterocycle, which may be saturated or may contain one to three double bonds, and which may be substituted by 1 or more $R_8$ groups;
- $R_6$ is a C1-C6 alkyl that may be substituted by one or more groups selected from: C3-C7 cycloalkyl, C1-C6 alkoxy, haloC1-C6 alkoxy, hydroxy, haloC1-C6 alkyl;
- $R_7$ is a group R5, a group $R_6$, C3-C7 cycloalkyl, C1-C6 alkoxy, hydroxy, halogen, nitro, cyano, $C(O)NR_9R_{10}$, phenyl which may be substituted by 1 to 4 $R_8$ groups;
- $R_8$ is C1-C6 alkyl, halo C1-C2 alkyl, halogen, nitro, C1-C6 alkoxy or cyano;
- $R_9$ is hydrogen or C1-C6 alkyl;
- $R_{10}$ independently from $R_9$, has the same meanings;
- X is carbon or nitrogen;
- n is 1 or 2.

Acid addition salts of the free base amino compounds of the present invention may be prepared by methods well known in the art, and may be formed from organic and inorganic acids. Suitable organic acids include maleic, malic, fumaric, benzoic, ascorbic, succinic, methanesulfonic, p-toluensulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all acceptable salt forms.

The solvates may, for example, be hydrates.

References hereinafter to a compound according to the invention include both compounds of formula (I) and their pharmaceutically acceptable acid addition salts together with pharmaceutically acceptable solvates.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as recemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention.

The term C1-C6 alkyl as used herein as a group or a part of the group refers to a linear or branched alkyl group containing from 1 to 6 carbon atoms; examples of such groups include methyl, ethyl, propyl, isopropyl, n-butyl, isobutyl, tert butyl, pentyl or hexyl.

The term C3-C7 cycloalkyl group means a non aromatic monocyclic hydrocarbon ring of 3 to 7 carbon atom such as, for example, cyclopropyl, cyclobutyl, cyclopentyl, cyclohexyl or cycloheptyl; while unsaturated cycloalkyls include cyclopentenyl and cyclohexenyl, and the like.

The term halogen refers to a fluorine, chlorine, bromine or iodine atom.

The term halo C1-C6 alkyl, or halo C1-C2 alkyl means an alkyl group having one or more carbon atoms and wherein at least one hydrogen atom is replaced with halogen such as for example a trifluoromethyl group and the like.

The term C2-C6 alkenyl defines straight or branched chain hydrocarbon radicals containing one or more double bond and having from 2 to 6 carbon atoms such as, for example, ethenyl, 2-propenyl, 3-butenyl, 2-butenyl, 2-pentenyl, 3-pentenyl, 3-methyl-2-butenyl or 3-hexenyl and the like.

The term C1-C6 alkoxy group may be a linear or a branched chain alkoxy group, for example methoxy, ethoxy, propoxy, prop-2-oxy, butoxy, but-2-oxy or methylprop-2-oxy and the like.

The term halo C1-C6 alkoxy group may be a C1-C6 alkoxy group as defined before substituted with at least one halogen, preferably fluorine, such as $OCHF_2$, or $OCF_3$.

The term C2-C6 alkynyl defines straight or branched chain hydrocarbon radicals containing one or more triple bond and having from 2 to 6 carbon atoms including acetylenyl, propynyl, 1-butynyl, 1-pentynyl, 3-methyl-1-butynyl and the like.

The term aryl means an aromatic carbocyclic moiety such as phenyl, biphenyl or naphthyl.

The term heteroaryl means an aromatic heterocycle ring of 5 to 10 members and having at least one heteroatom selected from nitrogen, oxygen and sulfur, and containing at least 1 carbon atom, including both mono-and bicyclic ring systems.

Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, triazolyl, tetrazolyl, and quinazolinyl.

The term heterocycle means a 5 to 7-membered monocyclic, or 7-to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

The term 5-6 membered heterocycle means, according to the above definition, a 5-6 monocyclic heterocyclic ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized. Heterocycles include heteroaryls as defined above. The heterocycle may be attached via any heteroatom or carbon atom. Thus, the term include (but are not limited to) morpholinyl, pyridinyl, pyrazinyl, pyrazolyl, triazolyl, imidazolyl, oxadiazolyl, oxazolyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

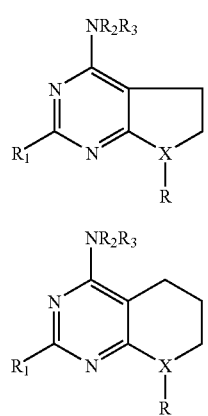

In one preferred embodiment in which n is 1 according to the definition of the compounds of formula (I) above, the CRF receptor antagonists of this invention have structure (Ia), and, when n is 2, then the CRF receptor antagonists of this invention have structure (Ib), wherein R, $R_1$, $R_2$ and $R_3$ are deined as above.

Further representative compounds of this invention include compounds of general formula (I), (Ia) and (Ib), in which $R_2$ and $R_3$ together with N form a saturated or unsaturated heterocycle, which may be substituted by 1 to 3 $R_7$ groups or $R_2$ and $R_3$ together with N form a 5-10 membered heteroaryl group, in which the 5-membered heteroaryl group contains at least one heteroatom selected from oxygen, sulphur or nitrogen and the 6-10 membered heteroaryl group contains from 1 to 3 nitrogen atoms and wherein said 5-10 membered heteroaryl may be substituted by 1 to 3 $R_7$ groups, such $R_7$ groups are defined as above.

Depending upon the choice of X, the CRF receptor antagonists of this invention include compounds having the following structures (Ia-1), (Ia-2), (Ib-1), (Ib-2).

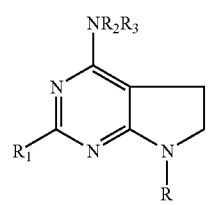

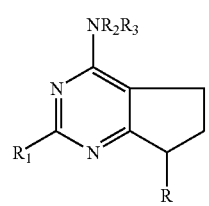

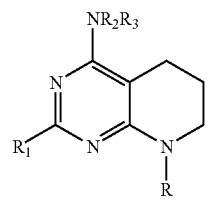

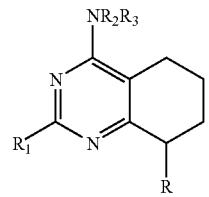

More specific embodiments of the invention include, but are not limited to, compounds of general formula (Ia-1), (Ia-2), (Ib-1), and (Ib-2), in which the group $NR_2R_3$ represents a secondary amine or a tertiary amine.

In particular compounds of formula (1-1), (1-2), (1-3), (1-4), (1-5), (2-1), (2-2), (2-3), (3-1), (3-2), (3-3), (4-1), (4-2) are preferred
(1-1)
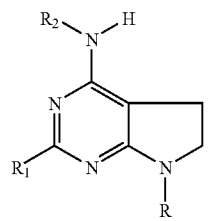
(1-2)
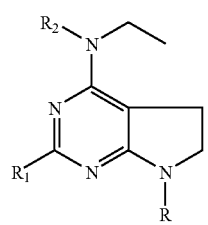
(1-3)
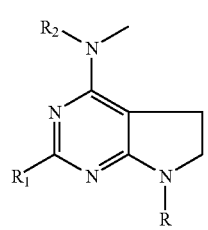
(1-4)
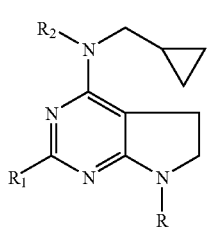
(1-5)
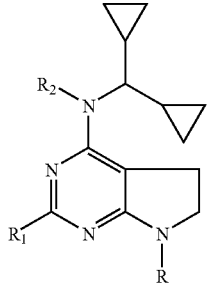
(2-1)
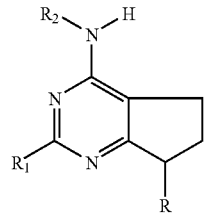
-continued
(2-2)
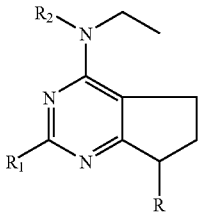
(2-3)
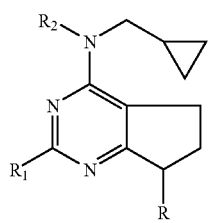
(3-1)
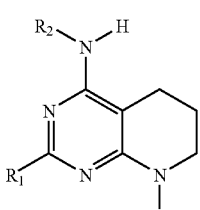
(3-2)
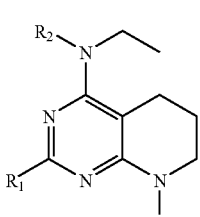
(3-3)
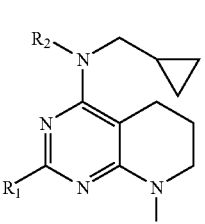
(4-1)
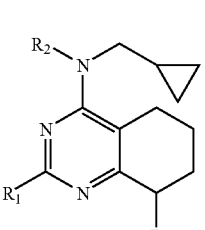
(4-2)
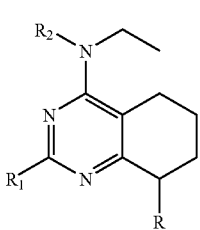

in which $R_1$, $R_2$, R have the meanings as defined before. Examples of such compounds are reported in the Experimental Part.

Further specific embodiments of the invention include, but are not limited to, compounds of the formula (Ia-1), (Ia-2), (Ib-1) and (Ib-2), in which the group $NR_2R_3$ represents a 5-6 membered heterocycle.

In particular compounds of formula (1-6), (1-7), (1-8), (1-9), (1-10), (1-11), (1-12), (2-4), (2-5) and (3-4) are preferred

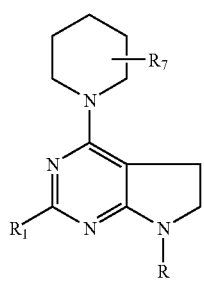
(1-6)

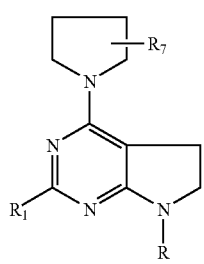
(1-7)

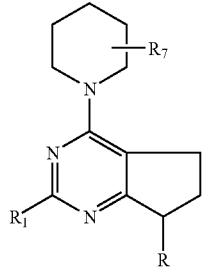
(2-4)

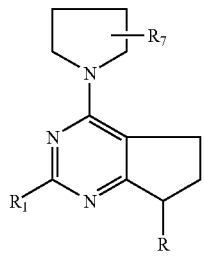
(2-5)

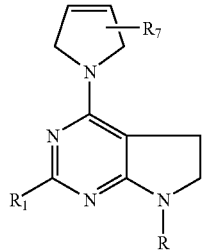
(1-8)

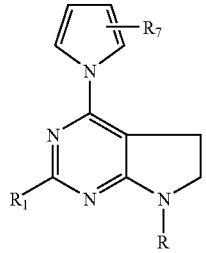
(1-9)

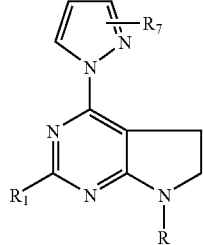
(1-10)

(1-11)

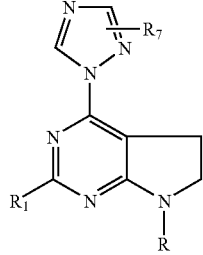
(1-12)

(3-4)

in which $R_1$, R and $R_7$ have the meanings as defined before.

Examples of such compounds are reported in the Experimental Part.

Even more preferred embodiments of the invention include, but are not limited to, compounds of the formula (I); (Ia), (Ib), (Ic), (Id); (Ia-1), (Ia-2), (Ib-1), (Ib-2), (Ic-1), (Ic-2), (Id-1), (Id-2), (1-1), (1-2), (1-3), (1-4), (1-5), (1-6), (1-7), (1-8), (1-9), (1-10), (1-11), (1-12), (2-1), (2-2), (2-3), (2-4), (2-5), (3-1), (3-2), (3-3), (3-4), (4-1), and (4-2)

wherein:

$R_1$ is C1-C3 alkyl group or halo C1-C3 alkyl group, preferably methyl or trifluoromethyl;

R is an aryl group selected from: 2,4-dichlorophenyl, 2-chloro-4-methylphenyl, 2-chloro-4-trifluoromethyl, 2-chloro-4-methoxyphenyl, 2,4,5-trimethylphenyl, 2,4-dimethylphenyl, 2-methyl-4-methoxyphenyl, 2-methyl-4-chlorophenyl, 2-methyl-4-trifluoromethyl, 2,4-dimethoxyphenyl, 2-methoxy-4-trifluoromethylphenyl, 2-methoxy-4-chlorophenyl, 3-methoxy-4-chlorophenyl, 2,5-dimethoxy-4-chlorophenyl, 2-methoxy-4-isopropylphenyl, 2-methoxy-4-trifluoromethylphenyl, 2-methoxy-4-isopropylphenyl, 2-methoxy-4-methylphenyl, 2-trifluoromethyl-4-chlorophenyl, 2,4-trifluoromethylphenyl, 2-trifluoromethyl-4-methylphenyl, 2-trifluoromethyl-4-methoxyphenyl, 2-bromo-4-isopropylphenyl, 4-methyl-6-dimethylaminopyridin-3-yl, 3,5-dichloro-pyridin-2-yl, 2,6-bismethoxy-pyridin-3-yl and 3-chloro-5-tricluoromethyl-pyridin-2-yl.

Preferred compounds according to the invention are:

[7-(2,4-dichlorophenyl)-2-methyl-6,7-dihydro-5H-pyrrolo[2,3-d]pyrimidin-4-yl]-(1-ethyl-propy)amine (1-1-1);

[7-(2-bromo-4-isopropylphenyl)-2-methyl-6,7-dihydro-5H-pyrrolo[2,3-d]pyrimidin-4-yl]-(1-ethylpropyl)amine (1-1-2);

[7-(2,4-bis-trifluoromethylphenyl)-2-methyl-6,7-dihydro-5H-pyrrolo[2,3-d]pyrimidin-4-yl]-(1-propylbutyl)amine (1-1-3);

butyl-[7-(2,4-dichlorophenyl)-2-methyl-6,7-dihydro-5H-pyrrolo[2,3-d]-pyrimidin-4-yl]ethyl-amine (1-2-1);

[7-(2-bromo-4-isopropylphenyl)-2-methyl-6,7-dihydro-5H-pyrrolo[2,3-d]pyrimidin-4-yl]-butylethylamine (1-2-2);

butyl-[7-(2-chloro-4-trifluoromethylphenyl)-2-methyl-6,7-dihydro-5H-pyrrolo[2,3-d]pyrimidin-4-yl]ethylamine (1-2-3);

[7-(2,4-bis-trifluoromethylphenyl)-2-methyl-6,7-dihydro-5H-pyrrolo[2,3-d]pyrimidin-4-yl]-butylethylamine (1-2-4);

[7-(2-chloro-4-trifluoromethylphenyl)-2-methyl-6,7-dihydro-5H-pyrrolo[2,3-d]pyrimidin-4-yl]-cyclopropylmethylpropylamine (1-4-1);

[7-(2,4-bis-trifluoromethylphenyl)-2-methyl-6,7-dihydro-5H-pyrrolo[2,3-d]pyrimidin-4-yl]-cyclopropylmethylpropylamine (1-4-2);

[7-(2-bromo-4-isopropylphenyl)-2-methyl-6,7-dihydro-5H-pyrrolo[2,3-d]pyrimidin-4-yl]-cyclopropylmethylpropylamine (1-4-3);

cyclopropylmethyl [7-(2,4-dichlorophenyl)-2-methyl-6,7-dihydro-5H-pyrrolo[2,3-d]pyrimidin-4-yl]propylamine (1-4-4);

7-(2,4-dichlorophenyl)4-(2-ethyl-piperidin-1-yl)-2-methyl-6,7-dihydro-5H-pyrrolo[2,3-d]pyrimidine (1-6-3);

7-(2,4-dichlorophenyl)-4-[(2R,5R)-2,5-dimethylpyrrolidin-1-yl]-2-methyl-6,7-dihydro-5H-pyrrolo[2,3-d]pyrimidine (1-7-3);

7-(2,4-dichlorophenyl)-2-methyl-4-(3-thiazol-2-yl-pyrazol-1-yl)-6,7-dihydro-5H-pyrrolo[2,3-d]pyrimidine (1-10-1);

7-(2,4-bis-trifluoromethylphenyl)-2-methyl-4-(3-thiazol-2-yl-pyrazol-1-yl)-6,7-dihydro-5H-pyrrolo[2,3-d]pyrimidine (1-10-2);

7-(2-bromo-4-isopropylphenyl)-2-methyl-4-(3-trifluoromethyl-pyrazol-1-yl)-6,7-dihydro-5H-pyrrolo[2,3-d]pyrimidine (1-10-6);

7-(2,4-dichlorophenyl)4-(5-isopropyl-3-trifluoromethyl-pyrazol-1-yl)-2-methyl-6,7-dihydro-5H-pyrrolo[2,3-d]pyrimidine and 7-(2,4-dichlorophenyl)-4-(3-isopropyl-5-trifluoromethyl-pyrazol-1-yl)-2-methyl-6,7-dihydro-5H-pyrrolo[2,3-d]pyrimidine (1-10-7);

7-(2,4-dichlorophenyl)4-(3-ethyl-5-trifluoromethylpyrazol-1-yl)-2-methyl-6,7-dihydro -5H-pyrrolo[2,3-d]pyrimidine (1-10-9);

7-(2,4-dichlorophenyl)-4-(3,5-dimethylpyrazol-1-yl)-2-methyl-6,7-dihydro-5H-pyrrolo[2,3-d]pyrimidine (1-10-11);

7-(2,4-dichlorophenyl)4-(3-dimethoxymethyl-pyrazol-1-yl)-2-methyl-6,7-dihydro-5H-pyrrolo[2,3-d]pyrimidine (1-10-15);

7-(2,4-dichlorophenyl)-4-(3-ethyl-5-trifluoromethylpyrazol-1-yl)-2-methyl-6,7-dihydro -5H-pyrrolo[2,3-d]pyrimidine (1-10-16);

4-(4-bromo-3-methyl-pyrazol-1-yl)-7-(2,4-dichlorophenyl)-2-methyl-6,7-dihydro-5H-pyrrolo[2,3-d]pyrimidine (1-10-18);

4-(4-bromopyrazol-1-yl)-7-(2,4-dichlorophenyl)-2-methyl-6,7-dihydro-5H-pyrrolo[2,3-d]pyrimidine (1-10-19);

7-(2,4-dichlorophenyl)4-[3-(4-chlorophenyl)-pyrazol-1-yl]-2-methyl-6,7-dihydro-5H-pyrrolo[2,3-d]pyrimidine (1-10-23);

7-(2,4-dichlorophenyl)-4-[3-(2-nitrophenyl)-pyrazol-1-yl]-2-methyl-6,7-dihydro-5H-pyrrolo[2,3-d]pyrimidine (1-10-24);

7-(2,6-dimethoxy-pyridin-3-yl)-2-methyl-4-(3-thiazol-2-yl-pyrazol-1-yl)-6,7-dihydro-5H-pyrrolo[(2,3-d)]pyrimidine (1-10-30);

7-(2,4-bis-trifluoromethyl-phenyl)-2-methyl-4-(3-morpholyn-4-yl-pyrazol-1-yl)-6,7-dihydro-5H-pyrrolo[(2,3-d)]pyrimidine (1-10-31);

7-(2,4-bis-trifluoromethyl-phenyl)-2-methyl-4-(3-pyridin-3-yl-pyrazol-1-yl)-6,7-dihydro-5H-pyrrolo[(2,3-d)]pyrimidine (1-10-32);

7-(2,4-bis-trifluoromethyl-phenyl)-2-methyl-4-(3-pyrazin-2-yl-pyrazol-1-yl)-6,7-dihydro-5H-pyrrolo[(2,3-d)]pyrimidine (1-10-33);

7-(2,4-bis-trifluoromethyl-phenyl)-2-methyl-4-(3-oxalol-5-yl-pyrazol-1-yl)-6,7-dihydro -5H-pyrrolo[(2,3-d)]pyrimidine (1-10-40);

7-(2,4-dichlorophenyl-2-methyl-4-(3-trifluoromethyl-(1,2,4)triazol-1-yl)-6,7-dihydro -5H-pyrrolo(2,3-d)pyrimidine (1-11-2);

butyl-[7-(2,4-dichlorophenyl)-2-methyl-6,7-dihydro-5H-cyclopentapyrimidin-4-yl]-ethyl-amine (2-2-5);

cyclopropylmethyl[7-(2,4-dimethoxyphenyl)-2-methyl-6,7-dihydro-5H-cyclopentapyrimidin-4-yl]-propyl-amine (2-3-5);

cyclopropylmethyl[7-(2,4-dichlorophenyl)-2-methyl-6,7-dihydro-5H-cyclopentapyrimidin-4-yl]-propylamine (2-3-6);

7-(2,4-dichlorophenyl)4-[(2R,5R)-2,5-dimethylpyrrolidin-1-yl]-2-methyl-6,7-dihydro-5H-cyclopentapyrimidine (2-5-1);

7-(2,4-dichlorophenyl)4-[(2R,5R)-2,5-dimethylpyrrolidin-1-yl]-2-methyl-6,7-dihydro-5H-cyclopentapyrimidine (2-5-2);

[8-(2,4-bis-trifluoromethylphenyl)-2-methyl-5,6,7,8-tetrahydropyrido[2,3-d]pyrimidin-4-yl](1-propylbutyl)amine (3-1-1);

butyl-[8-(2,4-dichlorophenyl)-2-methyl-5,6,7,8-tetrahydropyrido[2,3-d]pyrimidin-4-yl]-ethylamine (3-1-2);

cyclopropylmethyl[8-(2,4-dichlorophenyl)-2-methyl-5,6,7,8-tetrahydropyrido[2,3-d]pyrimidin-4-yl]propylamine (3-1-3).

In general, the compounds of structure (I) may be made according to the organic synthesis techniques known to those skilled in this field, as well as by the representative methods set forth in the Examples.

Compounds of formula (I), and salts and solvates thereof, may be prepared by the general methods outlined hereinafter. In the following description, the groups R, $R_1$, $R_2$, $R_3$, $R_4$, $R_5$, $R_6$, $R_7$, $R_8$, $R_9$, $R_{10}$, and n have the meanings as previously defined for compounds of formula (I) unless otherwise stated.

Compounds of formula (I) may be prepared by reaction of a compound of formula (II), wherein L is a leaving group selected in a group consisting from halogens (preferably chlorine) or reactive residue of a sulphonic acid (e.g. mesylate, tosylate, triflate).

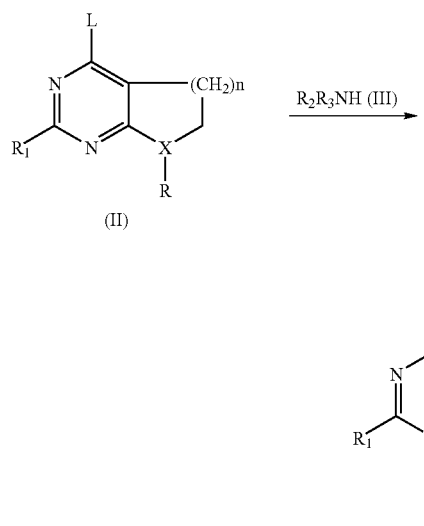

with the amino compound $NHR_2R_3$ (III). The reaction can be optionally carried out in an aprotic solvent such NN-dimethylformamide in the presence, if desired, of a strong base such as sodium hydride and with heating.

Alternatively, when $NR_2R_3$ represents a cycle, compounds (II) may react with hydrazine to give the corresponding hydrazino derivatives and then they may be cyclised to the desired final compound (I).

Compounds of formula (II), wherein X is nitrogen are equivalent to compounds of formula (IIa), may be prepared by cyclisation of a compound of formula (IV), wherein p is 1 or 2 and Ra is a suitable protecting group for the amino group. The activation of the hydroxy group is performed by conversion into a suitable leaving group, such as mesylate. The deprotection of the amino protecting group can be performed, for example, using an acid, such as trifluoroacetic acid, in an aprotic solvent, like dichloromethane.

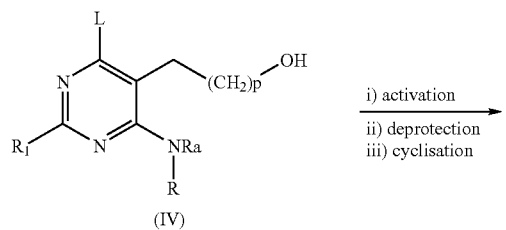

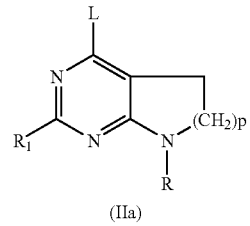

The cyclisation may take place in an aprotic solvent such as tetrahydrofuran and in the presence of a tertiary amine such as triethyl amine.

Compounds of formula (IV), wherein p is 1 are equivalent to compounds of formula (IVa), may be prepared by oxidation of a compound of formula (V) to the corresponding aldehyde of formula (VI), followed by reduction to alcohol.

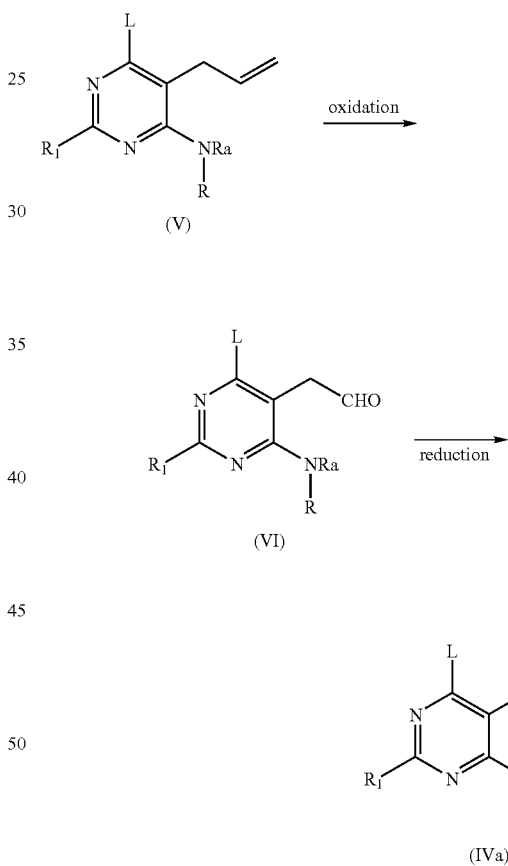

The oxidation is carried out, for example, with ozone at low temperature, e.g. −78° C., in a solvent such as dichloromethane.

The reduction takes places using for example sodium borohydride in a solvent such as methanol.

Compounds of formula (IV), wherein p is 2, may be prepared by reduction of an aldehyde of formula (VII) with a suitable reducing agent, such as diisobutylaluminumhydride in usual conditions (aprotic solvent such as dichloromethane at low temperature, e.g. 0° C.).

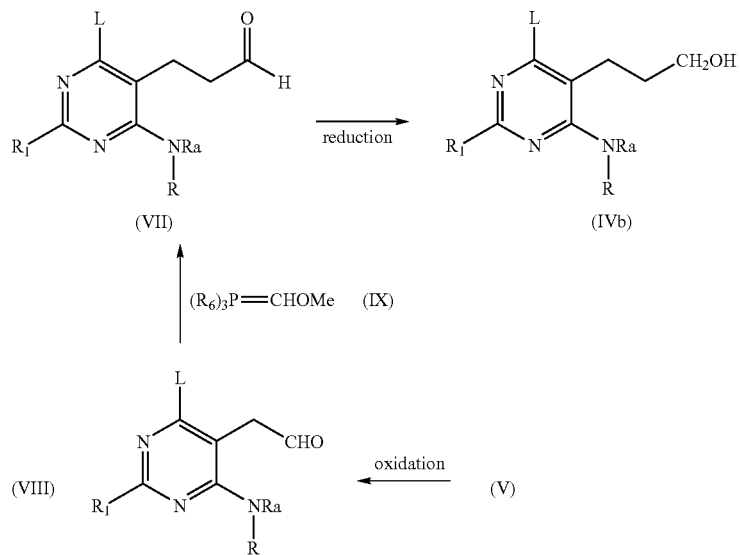

Compounds of formula (VII) may be prepared by Wittig reaction of a compound of formula (VIII) with a phosphorus ylide (IX), wherein $R_6$ is phenyl or a phenyl derivative, followed by hydrolysis with an acid (e.g. hydrogenchloride). The reaction is carried out in an aprotic solvent such as acetonitrile or an ether such as tetrahydrofuran.

Aldehydes (VIII) may be obtained by oxidation of a compound of formula (V).

The oxidation is carried out in the presence of ozone at low temperature, e.g. −78° C., in a solvent such as dichloromethane.

Alternatively compounds of formula (IVc) may be prepared by reaction of a compound of formula (IX) with amine (X), in which Rb is a suitable protecting group for the hydroxy group.

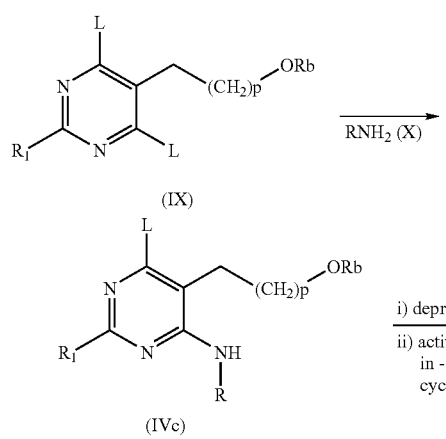

The reaction preferably takes place in an aprotic solvent such as dichlorometane or N,N-dimethyl formamide optionally in the presence of a tertiary amine (e.g. triethylamine).

Compounds (IVc) may be subjected to deprotection and then activation of the hydroxy group (e.g mesylate) as described before followed by in situ cyclisation Compounds of formula (IX) may be prepared by reduction of an ester of formula (XI), with a suitable reducing agent, such as diisobutylaluminumnhydride.

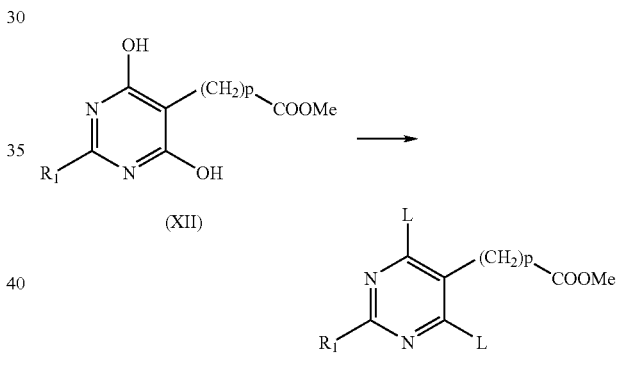

Compounds of formula (IX) may be prepared from compounds of formula (XII), by conversion of the hydroxy groups in suitable leaving groups. For example, the halogenation reaction may be carried out using conventional methods known in the art. Thus, for example, the reaction may be carried out by treatment with $PO(Hal)_3$, wherein Hal is preferably chlorine.

Compounds of formula (V), may be prepared by reaction of a compound of formula (XIII) with amine (X), followed by protection of the amino group.

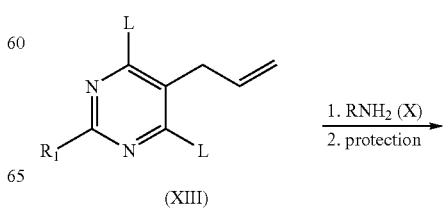

-continued

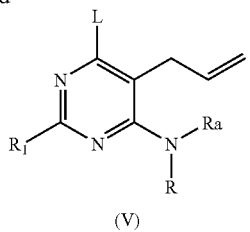

(V)

The reaction preferably takes place in an aprotic solvent such as tetrahydrofuran, dichlorometane or N,N-dimethylformamide in the presence of a strong base such sodium hydride and by heating.

Compounds of formula (II), wherein X is a carbon atom are equivalent to compounds of formula (IIb), may be prepared by conversion of the hydroxy group of compounds of formula (XIV) into a leaving group.

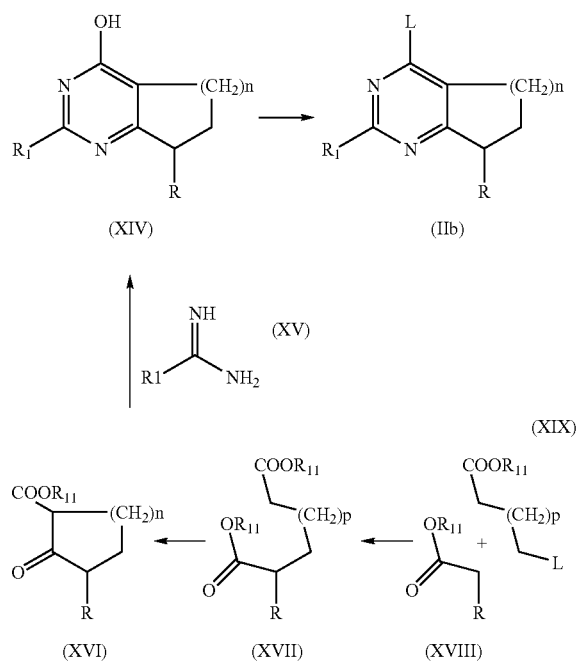

For example, the halogenation reaction may be carried out using conventional methods known in the art. Thus, e.g. the reaction may be carried out by treatment with $PO(Hal)_3$, wherein Hal is preferably chlorine.

Compounds of formula (XIV) may be prepared by cyclisation of a compound of formula (XVI) with a salt (e.g. hydrochloride) of acetamidine (XV).

The reaction is carried out in the presence of an alkaline organic base C1-C4 (e.g. sodium methoxide) in a solvent such as methyl alcohol.

Compounds of formula (XVI) may be prepared by cyclisation of a compound of formula (XVII), in which $R_{11}$ is a linear or branched C1-C4 alkyl and p is defined as above.

The cyclisation may be carried out in the presence of an organic alkaline C1-C4 alkoxyde (e.g sodium methoxide) in an aprotic solvent such as N,N-dimethylformamide or toluene and at temperature ranging from 20° to 100° C.

Compounds of formula (XVII) can be prepared by reaction of a compound of formula (XVIII) with a compound of formula (XIX), wherein L is preferably a bromine or iodine atom.

The reaction is carried out in aprotic solvent such as an ether e.g. tetrahydrofuran at low temperature, e.g. −78° C., and in the presence of a strong base such as Lithium diisopropylamide.

Alternatively, compounds of formula (XVIa), corresponding to compounds of formula (XVI) when n is 2, may be prepared according to the following scheme from cyclohexanone. It can be converted to its reactive enol ether (such as a triflate, as in Lai and McAllister; *Synth. Commun.*; 29; 3; 1999; p 409), then coupled with an organic metallic derivative of R (such as a boronic acid derivative, as in Suzuki, Akira; *J. Org. Chem.*; 58; 8; 1993; p 2201) to give the substituted cyclohexene, which can be epoxidised, using for example chloroperoxybenzoic acid, and converted to a carbonyl group under acidic conditions (using, for example, sulfuric acid, as in Crotai, P. et al; *Tetrahedron*; 29; 1973; p 155). The ketone thus obtained can be carboxymethylated, using a strong base (such as lithium diisopropyl amide) and an acylating agent (such as ethyl cyanoformate).

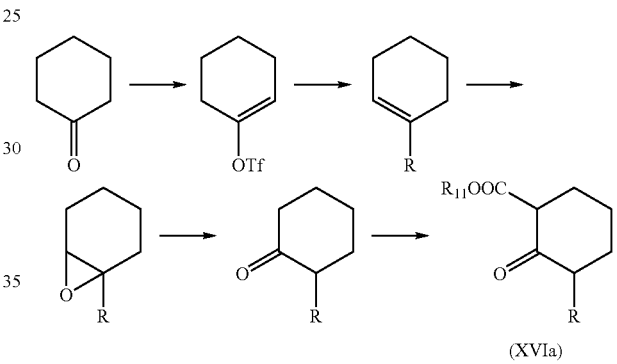

(XVIa)

In another alternative, compounds of formula (XVIb), corresponding to compounds of formula (XVI) when n is 1, may be prepared according to the following scheme from 2-chloro-cyclopentanone, by reaction with a suitable Grignard derivative of the group R and then carboxymethylated as described above.

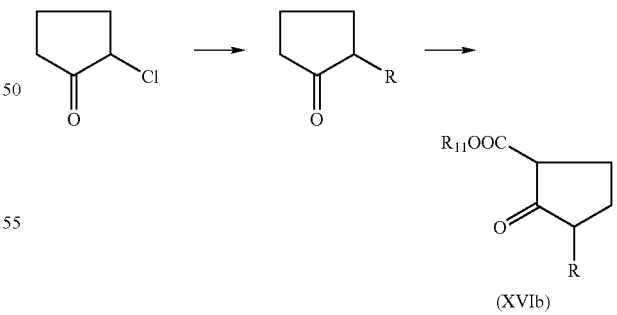

(XVIb)

Compounds of formula (XI), (XII), (XIII), (XVIII) and (XIX) are either known compounds or may be prepared by analogous methods to those described for known compounds.

Pharmaceutical acceptable salts may also be prepared from other salts, including other pharmaceutically acceptable salts, of the compound of formula (I) using conventional methods.

The compounds of formula (I) may readily be isolated in association with solvent molecules by crystallisation or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The subject invention also includes isotopically-labeled compounds, which are identical to those recited in formulas I and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^8F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula I and following of this invention can generally be prepared by carrying out the procedures disclosed in the Schemes and/or in the Examples below, by substituting a readily available isotopically labeled reagent for a non-isotopically labeled reagent.

The CRF receptor antagonists of the present invention demonstrate activity at the CRF receptor site including CRF 1 and CRF 2 receptors and may be used in the treatment of conditions mediated by CRF or CRF receptors.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (J. Neuroscience 7: 88,1987) and Battaglia et al. (Synapse 1: 572,1987).

The CRF receptors-binding assay was performed by using the homogeneous technique of scintillation proximity (SPA). The ligand binds to recombinant membrane preparation expressing the CRF receptors which in turn bind to wheatgerm agglutinin coated SPA beads. In the Experimental Part will be disclosed the details of the experiments.

With reference to CRF receptor binding affinities, CRF receptor antagonists of this invention have a Ki less than 10 µm. In a preferred embodiment of this invention, a CRF receptor antagonist has a Ki comprised in a range from 0.1 nM and 10 µm.

In a more preferred embodiment the value of Ki is less than 1 µm and more preferably less than 0.1 µm. As set forth in greater detail below, the Ki values of representative compounds of this invention were assayed by the methods set forth in Example 5.

Preferred compounds having a Ki of less than 1 µm are compound numbers 1-10-9, 1-10-11, 1-10-16, 1-10-19, 1-10-23, 1-10-24, 1-10-31, 1-10-32, 1-10-33, 1-10-40, 1-11-2, 2-2-5, 2-3-5, 2-3-6 and 2-5-2.

More preferred compounds having a Ki less than 0.1 µm are compound numbers 1-1-1, 1-1-2, 1-1-3, 1-2-1, 1-2-2, 1-2-3, 1-2-4, 1-4-1, 1-4-2, 1-4-3, 1-4-4, 1-6-3, 1-7-3, 1-10-1, 1-10-2, 1-10-6, 1-10-7, 1-10-15, 1-10-18, 1-10-30, 2-5-1, 3-1-1, 3-2-1 and 3-3-1.

Compounds of the invention may be useful in the treatment of central nervous system disorders where CRF receptors are involved. In particular in the treatment or prevention of major depressive disorders including bipolar depression, unipolar depression, single or recurrent major depressive episodes with or without psychotic features, catatonic features, melancholic features, a typical features or postpartum onset, the treatment of anxiety and the treatment of panic disorders. Other mood disorders encompassed within the term major depressive disorders include dysthymic disorder with early or late onset and with or without a typical features, neurotic depression, post traumatic stress disorders and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

Compounds of the invention are useful as analgesics. In particular they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch; and thalamic pain such as post stroke thalamic pain.

Compounds of the invention are also useful for the treatment of dysfunction of appetite and food intake and in circumstances such as anorexia, anorexia nervosa and bulimia.

Compounds of the invention are also useful in the treatment of sleep disorders including dysomnia, insomnia, sleep apnea, narcolepsy, and circadian ritmic disorders.

Compounds of the invention are also useful in the treatment or prevention of cognitive disorders. Cognitive disorders include dementia, amnestic disorders and cognitive disorders not otherwise specified.

Furthermore compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds), or in the treatment of tolerance to and dependence on opiates (e.g. cannabis, heroin, morphine) or benzodiazepines; in the treatment of cocaine, sedative ipnotic, amphetamine or amphetamine-related drugs (e.g. dextroamphetamine, methylamphetamine) addiction or a combination thereof.

Compounds of the invention are also useful as anti-inflammatory agents. In particular they are useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease (IBD) and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of allergic disorders, in particular allergic disorders of the skin such as urticaria, and allergic disorders of the airways such as rhinitis.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, waterbrash/regurgitation, heartburn, such as episodic heartburn, nocturnal heartburn, and meal-induced heartburn and dyspepsia.

Compounds of the invention are of particular use in the treatment of gastrointestinal disorders such as irritable bowel syndrome (IBS); skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Compounds of the invention are of particular use in the treatment of depressive states, in the treatment of anxiety and of panic disorders.

Depressive states include major depressive disorders including bipolar depression, unipolar depression, single or recurrent major depressive episodes with or without psychotic features, catatonic features, melancholic features, a typical features or postpartum onset, dysthymic disorder with early or late onset and with or without a typical features, neurotic depression and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type.

Compounds of the invention are useful for the treatment of neurotoxic injury which follows cerebral stroke, thromboembolic stroke, hemorrhagic stroke, cerebral ischemia, cerebral vasospam, hypoglycemia, hypoxia, anoxia, perinatal asphyxia cardiac arrest.

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by CRF.

In an alternative or further aspect there is provided a method for the treatment of a mammal, including man, in particular in the treatment of condition mediated by CRF, comprising administration of an effective amount of a compound of formula (I) or a pharmaceutically acceptable salt or a solvate thereof.

It will be appreciated that reference to treatment is intended to include prophylaxis as well as the alleviation of established symptoms.

Compounds of formula (I) may be administered as the raw chemical but the active ingredient is preferably presented as a pharmaceutical formulation.

Accordingly, the invention also provides a pharmaceutical composition which comprises at least one compound of formula (I) or a pharmaceutically acceptable salt thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus compounds of formula (I) may be formulated for oral, buccal, parenteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device.

A proposed dose of the compounds of the invention is 1 to about 1000 mg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

Thus for parenteral administration a daily dose will typically be in the range of 1 to about 100 mg, preferably 1 to 80 mg per day. For oral administration a daily dose will typically be within the range 1 to 300 mg e.g. 1 to 100 mg.

EXAMPLES

In the Intermediates and Examples unless otherwise stated:

Melting points (m.p.) were determined on a Gallenkamp m.p. apparatus and are uncorrected. All temperatures refers to ° C. Infrared spectra were measured on a FT-IR instrument. Proton Magnetic Resonance ($^1$H-NMR) spectra were recorded at 400 MHz, chemical shifts are reported in ppm downfield (d) from Me$_4$Si, used as internal standard, and are assigned as singlets (s), doublets (d), doublets of doublets (dd), triplets (t), quartets (q) or multiplets (m). Column chromathography was carried out over silica gel (Merck AG Darmstaadt, Germany). The following abbreviations are used in text: EtOAc=ethyl acetate, cHex=cyclohexane, CH$_2$Cl$_2$=dichloromethane, Et$_2$O=dietyl ether, DMF=N,N'-dimethylformamide, DIPEA=N,N-diisopropylethylamine MeOH=methanol, Et$_3$N=triethylamine, TFA=trifluoroacetic acid, THF=tetrahydrofuran, DIBAL-H=diisobutylaluminium hydride, DMAP=dimethylaminopyridine, LHMDS=lithiumhexamethyldisilazane; Tlc refers to thin layer chromatography on silica plates, and dried refers to a solution dried over anhydrous sodium sulphate; r.t. (RT) refers to room temperature.

Intermediate 1

5-Allyl-4,6-dihydroxy-2-methyl-pyrimidine

Sodium (2 g) was added portionwise to anh. MeOH (100 mL), at 0° C., under N$_2$. After consumption of metallic sodium, acetamidine hydrochloride (8.4 g) was added. After 10 min. of stirring the precipitated NaCl was filtered off. Diethyl-allyl-malonate (6 mL) was added to the solution of free acetamidine and the mixture was stirred at r.t. for 2 days. The reaction mixture was concentrated and then neutralized with concentrated hydrochloric acid, filtered to obtain the title compound (4.25 g) as a white solid.

NMR ($^1$H, DMSO-d$_6$): δ 11.61 (bs, 2H), 5.75 (m, 1H), 4.92 (m, 1H), 4.84 (m, 1H), 2.94 (d, 2H), 2.19 (s, 3H).

MS (m/z): 166 [M]$^+$.

Intermediate 2

5-Allyl-4,6-dichloro-2-methylpyrimidine

Intermediate 1 (6.0 g) was mixed with POCl$_3$ (70 mL) and heated at reflux for 3 hr. The resulting solution was cooled to r.t. and poured slowly into ice/water (600 mL) with vigorous stirring. The product was extracted with EtOAc (3×50 mL). The combined organic extracts were washed with saturated NaHCO$_3$ (60 mL) and brine (40 mL), dried over anh. Na$_2$SO$_4$, filtered and concentrated in vacuo. The crude oil was purified by flash chromatography (silica gel, cHex 100%) to give the title compound (4.78 g) as a light yellow oil.

NMR ($^1$H, CDCl$_3$): δ 5.85 (m, 1H), 5.15 (dq, 1H), 5.11 (dq, 1H), 3.61 (dt, 2H), 2.67 (s, 3H).

MS (m/z): 202 [M]$^+$ 0.2Cl; 167 [MH—Cl]$^+$, 1Cl.

Intermediate 3

(5-Allyl-6-chloro-2-methylpyrimidin-4-yl)-(2,4-dichlorophenyl)amine

A solution of 2,4-dichloroaniline (798 mg) in anh. THF (22 mL), under N$_2$, was treated with sodium hydride (95% in mineral oil, 393 mg) at 0° C. for 15 min before intermediate 2 (1 g) was added. The mixture was heated at reflux for 3 hr and quenched with water (20 mL). The product was extracted with ethyl acetate (2×20 mL), dried over anh. Na$_2$SO$_4$ and concentrated in vacuo. The crude product was purified by flash chromatography (silica gel, EtOAc/cHex 4:96) to give the title compound (725 mg) as a white solid.

NMR ($^1$H, CDCl$_3$): δ 8.52 (d, 1H), 7.40 (d, 1H), 7.27 (dd, 1H), 7.21 (bs, 1H), 5.90 (m, 1H), 5.26 (m, 2H), 3.58 (m, 2H), 2.57 (s, 3H).

MS (m/z): 327 [M]$^+$, 3Cl.

Intermediate 4

(5-Allyl-6-chloro-2-methylpyrimidin-4-yl)-(2,4-dichlorophenyl) carbamic acid tert-butyl ester To a solution of intermediate 3 (146 mg) in anh. CH$_2$Cl$_2$ (11 mL), under N$_2$, was added (Boc)$_2$O (194 mg) and DMAP (cat). The reaction mixture was stirred at r.t. for 18 hr. The solution was diluted with water (10 mL) and extracted with EtOAc (3×15 mL). The combined organic extracts were dried over anh. Na$_2$SO$_4$, filtered and concentrated to dryness in vacuo. Flash chromatography of the crude product (silica gel, cHex/EtOAc 95:5) gave the title compound (164 mg) as a colorless oil.

NMR ($^1$H, CDCl$_3$): δ 7.47 (d, 1H), 7.20 (dd, 1H), 7.17 (d, 1H), 5.75 (tq, 1H), 5.05(dd, 1H), 4.97 (dd, 1H), 3.52 (d, 2H), 2.58 (s, 3H), 1.44 (s, 9H).

IR (nujol, cm$^{-1}$): 1729.

MS (m/z): 428 [MH]$^+$, 3Cl; 372 [MH−tBu+H]$^+$, 328 [MH−Boc+H]$^+$

Intermediate 5

[6-Chloro-5-(2-hydroxyethyl)-2-methylpyrimidin-4-yl]-(2,4-dichlorophenyl)carbamic acid tert-butyl ester A solution of intermediate 4 (160 mg) in CH$_2$Cl$_2$ (9 mL) and CH$_3$OH (1 mL) was ozonized (5 g.h$^{-1}$) at −78° C. for 10 min. When all the allyl pyrimidine had disappeared (according to TLC), the reaction mixture was first flushed with oxygen and then with nitrogen for 20 min. To the cooled reaction mixture was added NaBH$_4$ (56 mg) and the temperature was allowed to warm up to r.t. The solution was stirred for 3 hr at r.t. It was then diluted with water (10 mL) and extracted with CH$_2$Cl$_2$ (3×10 mL). The combined organic extracts were dried over anh. Na$_2$SO$_4$, filtered and concentrated to dryness in vacuo. The crude product was purified by flash chromatography (silica gel, cHex/EtOAc 85/15) to give the title compound (120 mg) as a white solid.

NMR ($^1$H, CDCl$_3$): δ 7.49 (d, 1H), 7.37 (d, 1H), 7.23 (dd, 1H), 3.93 (q, 2H), 3.05 (t, 2H), 2.59 (s, 3H), 1.89 (bs, 1H), 1.45 (s, 9H).

IR (nujol, cm$^{-1}$): 3430, 1717.

MS (m/z): 432 [MH]$^+$, 3Cl; 454 [MH+Na]$^+$, 332 [MH−Boc+H]$^+$

Intermediate 6

Methanesulfonic acid 2-{4-tert-butoxycarbonyl-(2,4-dichlorophenyl)amino]-6-chloro-2-methylpyrimidin-5-yl}ethyl ester To a solution of intermediate 5 (337 mg) in anh. CH$_2$Cl$_2$ (15 mL), at r.t, under N$_2$, was added Et$_3$N (545 μl) and CH$_3$SO$_2$Cl (120 μl). The reaction mixture was stirred at r.t. for 18 hr. Water (15 mL) and EtOAc (155 mL) were added, the phases were separated and the aqueous layer was extracted with additional EtOAc (2×15 mL). The combined organic extracts were washed with H$_2$O (20 mL), dried over anh. Na$_2$SO$_4$, filtered and concentrated in vacuo. The crude product was purified by flash chromatography (silica gel, cHex/EtOAc 75:25) to give the title compound (327 mg) as a white foam.

NMR ($^1$H, CDCl$_3$): δ 7.49 (d, 1H), 7.34 (d, 1H), 7.26 (m, 1H), 4.52 (t, 2H), 3.24 (t, 2H), 2.98 (s, 3H), 2.58 (s, 3H), 1.45 (s, 9H).

MS (m/z): 510 [MH]$^+$, 3Cl; 532 [MH+Na]$^+$, 454 [MH−tBu+H]$^+$, 410 [MH−Boc+H]$^+$

Intermediate 7

Methanesulfonic acid 2-[4-chloro-6-(2,4-dichlorophenylamino)-2-methylpyrimidin-5-yl]-ethyl ester A solution of intermediate 6 (327 mg) in 20% TFA in CH$_2$Cl$_2$ (10 mL) was stirred at r.t. for 2 hr. The solvent was removed in vacuo and the residue was partitionned between EtOAc (10 mL) and sat. aq. NaHCO$_3$ (10 mL), and the layers were separated. The aqueous layer was extracted with EtOAc (3×10 mL), and the combined organic extracts were dried over anh. Na$_2$SO$_4$, filtered and concentrated to dryness in vacuo to deliver the title compound (224 mg) as white solid.

NMR ($^1$H, CDCl$_3$): δ 8.39 (d, 1H), 7.49 (d, 1H), 7.44 (bs, 1H), 7.34 (dd, 1H), 4.56 (t, 2H), 3.28 (t, 2H), 3.03 (s, 3H), 2.61 (s, 3H).

MS (m/z): 410 [MH]$^+$, 3Cl.

Intermediate 8

4-Chloro-7-(2,4-dichlorophenyl)-2-methyl-6,7-dihydro-5H-pyrrolo[2,3-d]pyrimidine To a solution of intermediate 7 (224 mg) in anh. THF (10 mL) was added, at r.t., under N$_2$, NaH (95% mineral oil, 20 mg). The reaction was stirred for 2 hr at r.t. The solution was diluted with water (10 mL) and extracted with ethyl acetate (2×15 mL). The combined organic extracts were dried over anh. Na$_2$SO$_4$, filtered and concentrated to dryness in vacuo. The crude product was purified by flash chromatography (silica gel, cHex/EtOAc 75:25) to give the title compound (158 mg) as a white solid.

NMR ($^1$H, CDCl$_3$): δ 7.51 (s, 1H), 7.33 (m, 2H), 4.04 (t, 2H), 3.21 (t, 2H), 2.44 (s, 3H).

MS (m/z): 313[MH]$^+$, 3Cl

Intermediate 9

(5-Allyl-6-chloro-2-methylpyrimidin-4-yl)-(2-bromo-4-isopropylphenyl)amine

A solution of 2-bromo-4-isopropyl-aniline (422 mg) in anh. THF (3 mL), under N$_2$, was treated with sodium hydride (80% in mineral oil, 90 mg) at 0° C. for 15 min before intermediate 2 (400 mg) was added. The mixture was heated to reflux for 3 hr and quenched with water (10 mL). The product was extracted with ethyl acetate (2×15 mL) and dried over anh. Na$_2$SO$_4$. The solids were filtered and the solvent evaporated in vacuo. The crude product was purified by flash chromatography (silica gel, EtOAc/cHex 1:99) to give the title compound (360 mg) as a clear oil.

NMR ($^1$H, CDCl$_3$): δ 8.37(d, 1H), 7.41 (d,1H), 7.19 (dd, 1H), 7.14 (bs, 1H), 5.92 (m, 1H), 5.27-5.23 (m, 2H), 3.57 (m, 2H), 2.87 (m, 1H), 2.56 (s, 3H), 1.24 (d, 6H).

MS (m/z): 380 [MH]$^+$, 1Cl, 1Br.

Intermediate 10

(5-Allyl-6-chloro-2-methylpyrimidin-4-yl)-(2-bromo-4-isopropylphenyl) carbamic acid tert-butyl ester To a solution of intermediate 9 (271 mg) in anh. CH$_2$Cl$_2$ (2 mL), under N$_2$, was added (Boc)$_2$O (218 mg) and DMAP (cat). The reaction was stirred at r.t. for 3 hr. The solution was diluted with water (10 mL) and extracted with CH$_2$Cl$_2$ (3×15 mL). The combined organic extracts were dried over anh. Na$_2$SO$_4$, filtered and concentrated to dryness in vacuo. Flash chromatography of the crude product (silica gel, cHex/EtOAc 95:5) gave the title compound (295 mg) as a colorless oil.

NMR ($^1$H, CDCl$_3$): δ 7.49 (d, 1H), 7.09 (m, 2H), 5.63 (m, 1H), 4.96 (dd, 2H), 3.50 (d, 2H), 2.87 (m, 1H), 2.60 (s, 3H), 1.43 (s, 9H), 1.23 (d, 6H).

IR (nujol, cm$^{-1}$): 1729.

MS (m/z): 482 [MH]$^+$, 1Cl, 1Br.

Intermediate 11

(2-Bromo-4-isopropylphenyl)-[6-chloro-5-(2-hydroxyethyl)-2-methylpyrimidin-4-yl]-carbamic acid tert!-butyl ester A solution of intermediate 10 (293 mg) in anh. CH$_2$Cl$_2$ (1.8 mL) and CH$_3$OH (0.2 mL) was ozonized (5 g.h$^{-1}$) at −78° C. for 30 min. When all the starting material had disappeared (according to TLC in cHex/EtOAc 7:3), the reaction mixture was first flushed with oxygen and then with nitrogen for 10 min. To the cooled reaction mixture was added NaBH$_4$ (90 mg) and the temperature was allowed to warm up to 22° C. The solution was stirred for 3 hr at r.t. The solution was diluted with water (10 mL) and extracted with CH$_2$Cl$_2$ (3×10 mL). The combined organic extracts were dried over anh. Na$_2$SO$_4$, filtered and concentrated to dryness in vacuo. The crude product was purified by flash chromatography (silica gel, cHex/EtOAc 85:15) to give the title compound (260 mg) as a clear oil.

NMR ($^1$H, CDCl$_3$): δ 7.49 (d, 1H), 7.25 (d, 1H), 7.12 (dd, 1H), 3.84 (m, 2H), 3.02 (t, 2H), 2.88 (m, 1H) 2.61 (s, 3H), 1.8 (bt, 1H), 1.45 (s, 9H)1.23 (d, 6H).

IR (nujol, cm$^{-1}$): 1725, 1708.

MS (m/z): 486 [MH]$^+$, 1Cl, 1Br.

Intermediate 12

Methanesulfonic acid 2-[4-(2-bromo-4-isopropylphenylamino)-6-chloro-2-methylpyrimidin-5-yl]ethyl ester To a solution of intermediate 11 (261 mg) in anh. CH$_2$Cl$_2$ (5 mL), at r.t., under N$_2$, was added Et$_3$N (380 μl) and CH$_3$SO$_2$Cl (84 μl). The reaction was stirred at r.t. for 18 hr. Water (15 mL) and CH$_2$Cl$_2$ (15 mL) were added, the phases were separated and the aqueous layer was extracted with additional CH$_2$Cl$_2$ (2×15 mL). The combined organic extracts were dried over anh. Na$_2$SO$_4$, filtered and concentrated in vacuo. The residue was dissolved in 20% TFA in CH$_2$Cl$_2$ (2 mL) and was stirred at r.t. for 2 hr. The solvent was removed in vacuo and the residue was taken up in EtOAc (10 mL) and saturated NaHCO$_3$ (10 mL), and the layers were separated. The aqueous layer was extracted with CH$_2$Cl$_2$ (3×10 mL), and the combined organic extracts were dried over anh. Na$_2$SO$_4$, filtrated and concentrated to dryness in vacuo to deliver the title compound (231 mg) as yellow solid.

NMR ($^1$H, CDCl$_3$): δ 8.24 (d, 1H), 7.45 (d, 1H), 7.32 (bs, 1H), 7.22 (dd, 1H), 4.52 (t, 2H), 3.25 (t, 2H), 2.99(s, 3H), 2.55 (s, 3H), 2.89 (m, 1H), 1.25 (d, 6H).

MS (m/z): 462 [MH]$^+$, 1Cl, 1Br.

Intermediate 13

7-(2-Bromo-4-isopropylphenyl)-4-chloro-2-methyl-6,7-dihydro-5H-pyrolo[2,3-d]pyrimidine To a solution of intermediate 12 (231 mg) in anh. THF (4 mL) was added, at r.t., under N$_2$, NaH (80% mineral oil, 23 mg). The reaction mixture was stirred for 2 hr at 60° C. The solution was diluted with water (10 mL) and extracted with EtOAc (2×15 mL). The combined organic extracts were dried over anh. Na$_2$SO$_4$, filtered and concentrated to dryness in vacuo. The crude product was purified by flash chromatography (silica gel, cHex/EtOAc 90:10) to give the title compound (145 mg) as a white solid.

NMR ($^1$H, CDCl$_3$): δ 7.52(d, 1H), 7.24 (m, 2H), 4.02 (t, 2H), 3.19 (t, 2H), 2.91 (m, 1H), 2.43 (s, 3H), 1.26 (d, 6H).

MS (m/z): 366[MH]$^+$, 1Cl, 1Br.

Intermediate 14

(5-Allyl-6-chloro-2-methylpyrimidin-4-yl)-(2,4-bis-trifluoromethylphenyl)amine

A solution of 2,4-bis-trifluoromethyl-aniline (563 mg) in anh. THF (4 mL), at r.t., under N$_2$, was treated with sodium hydride (80% in mineral oil, 111 mg) at 0° C. for 15 min. Intermediate 2 (500 mg) was then added, the mixture was heated to reflux for 3 hr and quenched with water (10 mL). The aqueous layer was extracted with EtOAc (3×15 mL). The combined organic extracts were dried over anh. Na$_2$SO$_4$, the solids were filtered and the solvent evaporated in vacuo. The crude product was purified by flash chromatography (silica gel, EtOAc/cHex 4:96) to give the title compound (260 mg) as a brown oil.

NMR ($^1$H, CDCl$_3$): δ 8.55 (d, 1H), 7.88 (bs, 1H), 7.83 (bd, 1H), 7.19 (bs, 1H), 5.92 (m, 1H), 5.27 (m, 1H), 5.17 (m, 1H), 3.56 (m, 2H), 2.58 (s, 3H).

MS (m/z): 396 [MH]$^+$.

Intermediate 15

(5-Allyl-6-chloro-2-methylpyrimidin-4-yl)-(2,4-bis-trifluoromethylphenyl)-carbamic acid tert-butyl ester To a solution of intermediate 14 (435 mg) in anh. CH$_2$Cl$_2$ (3 mL), under N$_2$, at r.t., was added (Boc)$_2$O (336 mg) and DMAP (cat). The reaction was stirred at r.t. for 40 hr. The solution was diluted with water (10 mL) and extracted with EtOAc (3×15 mL). The combined organic extracts were dried over anh. Na$_2$SO$_4$, the solids were filtered and the solvent was evaporated to dryness in vacuo. Flash chromatography of the crude product (silica gel, cHex/EtOAc 96:4) gave the title compound as a yellow oil (460 mg).

NMR ($^1$H, CDCl$_3$): δ 7.96 (s, 1H), 7.83 (d, 1H), 7.55 (d, 1H), 5.90 (m, 1H) 5.18 (dd, 1H), 5.13 (d, 1H), 3.56 (m, 2H), 2.50 (s, 3H), 1.41 (s, 9H).

IR (nujol, cm$^{-1}$): 1726.

MS (m/z): 496 [MH]$^+$; 440 [MH−tBu+H]$^+$; 396 [MH-BOC+H]$^+$.

Intermediate 16

(2,4-Bis-trifluoromethylphenyl)-[6-chloro-5-(2-hydroxyethyl)-2-methylpyrimidin-4-yl]carbamic acid tert-butyl ester A solution of intermediate 15 (460 mg) in anh. CH$_2$Cl$_2$ (9 mL) and CH$_3$OH (1 mL) was ozonized (5 g.h$^{-1}$) at −78° C. for 20 min. When all the starting material had disappeared (according to TLC in cHex/EtOAc 7:3), the reaction mixture was first flushed with oxygen and then with nitrogen for 5 min. To the cooled reaction mixture was added NaBH$_4$ (137 mg) and the temperature was allowed to warm up to 22° C. The solution was stirred for 1.5 hr at r.t. It was then diluted with water (10 mL) and extracted with CH$_2$Cl$_2$ (3×10 mL). The combined organic extracts were dried over anh. Na$_2$SO$_4$, the solids were filtered and the solvent evaporated to dryness in vacuo. The crude product was purified by flash chromatography (silica gel, cHex/EtOAc 9:1) to give the title compound as white solid (385 mg).

NMR ($^1$H, CDCl$_3$): δ 7.96 (bs, 1H), 7.86 (bd, 1H), 7.74 (d, 1H), 4.13-4.05 (m, 2H), 3.07 (td, 2H), 2.49 (s, 3H), 2.21 (bs, 1H), 1.41 (s, 9H).

IR (nujol, cm$^{-1}$): 1724, 1602.

MS (m/z): 500 [MH]$^+$; 444 [MH−tBu+H]$^+$; 400 [MH−Boc+H]$^+$.

Intermediate 17

Methanesulfonic acid 2-[4-(2,4-bis-trifluoromethylphenylamino)-6-chloro-2-methyl-pyrimidin-5-yl]ethyl ester To a solution of intermediate 16 (385 mg) in anh. CH$_2$Cl$_2$ (5 mL), at r.t, under N$_2$, were added Et$_3$N (540 µl) and CH$_3$SO$_2$Cl (120 µl). The reaction was stirred at r.t. for 18 hr. Water (15 mL) and CH$_2$Cl$_2$ (15 mL) were added and the phases were separated. The aqueous layer was extracted with CH$_2$Cl$_2$ (2×15 mL). The combined extracts were dried over anh. Na$_2$SO$_4$, the solids filtered and the solvent evaporated in vacuo.

A solution of the crude product in 20% TFA/CH$_2$Cl$_2$ (4 mL) was stirred at r.t. for 2 hr. The solvent was removed in vacuo and the residue was redissolved in EtOAc (10 mL) and saturated NaHCO$_3$ (10 mL). The phases were separated and the aqueous layer was extracted EtOAc (3×10 mL). The combined organic extracts were dried over anh. Na$_2$SO$_4$, the solids were filtered and the solvent evaporated to dryness in vacuo to deliver the title compound as a yellow solid (322 mg).

NMR ($^1$H, CDCl$_3$): δ 9.09 (bs, 1H), 8.12 (d, 1H), 8.09 (s, 1H), 7.74 (d, 1H), 4.36 (t, 2H), 3.23 (t, 2H), 3.15 (s, 3H), 2.19 (s, 3H).

IR(CDCl$_3$, cm$^{-1}$): 1346, 1177

MS (m/z): 478[MH]$^+$.

Intermediate 18

7-(2,4-Bis-trifluoromethylphenyl)-4-chloro-2-methyl-6,7-dihydro-5H-pyrrolor[2,3-d]-pyrimidine To a solution of intermediate 17 (320 mg) in anh. THF (8 mL) was added, at r.t., under N$_2$, NaH (80% mineral oil, 30 mg). The reaction mixture was stirred for 2 hr at 60° C. It was then diluted with water (10 mL) and extracted with EtOAc (2×15 mL). The combined organic extracts were dried over anh. Na$_2$SO$_4$, the solids were filtered and the solvent evaporated to dryness in vacuo. The crude product was purified by flash chromatography (silica gel, cHex/EtOAc 90:10) to give the title compound as a white solid (154 mg).

NMR ($^1$H, CDCl$_3$): δ 8.04 (s, 1H), 7.93 (s, 1H), 7.53 (d, 1H), 4.00 (t, 2H) 2.42 (s, 3H).

MS (m/z): 381[MH]$^+$, 1Cl.

Intermediate 19

(5-Allyl-6-chloro-2-methylpyrimidin-4-yl)-(2-chloro-4-trifluoromethylphenyl)amine A solution of 2-chloro-4-trifluoromethylaniline (480 mgl) in anh. THF (4 mL), under N$_2$, was treated with sodium hydride (80% in mineral oil, 111 mg) at 0° C. for 15 min before intermediate 2 (500 mg) was added. The mixture was heated to reflux for 3 hr and quenched with water (10 mL). The product was extracted with EtOAc (3×15 mL), dried over anh. Na$_2$SO$_4$ and concentrated in vacuo. The crude product was purified by flash chromatography (silica gel, EtOAc/cHex 5:95) to give the title compound (401 mg) as a white solid.

NMR ($^1$H, CDCl$_3$): δ 8.80 (d, 1H), 7.67 (d, 1H), 7.57 (dd, 1H), 7.45 (bs, 1H), 5.92 (m, 1H), 5.31-5.25 (m, 2H), 3.62 (m, 2H), 2.62 (s, 3H).

MS (m/z): 362 [MH]$^+$, 2Cl.

Intermediate 20

(5-Allyl-6-chloro-2-methylpyrimidin-4-yl)-(2-chloro-4-trifluoromethylphenyl)carbamic acid tert-butyl ester To a solution of intermediate 19 (400 mg) in anh. CH$_2$Cl$_2$ (3 mL), under N$_2$, was added (Boc)$_2$O (1.4 eq, 336 mg) and DMAP (cat). The reaction was stirred at r.t. for 3 hr. The solution was diluted with water (10 mL) and extracted with EtOAc (3×15 mL). The combined organic extracts were dried over anh. Na$_2$SO$_4$, filtered and concentrated to dryness in vacuo. Flash chromatography of the crude product (silica gel, cHex/EtOAc 95/5) gave the title compound (462 mg) as a colorless oil.

NMR ($^1$H, CDCl$_3$): δ 7.74 (d, 1H), 7.49 (dd, 1H), 7.36 (d, 1H), 5.76 (m, 1H), 5.05-4.93 (m, 2H), 3.53 (d, 2H), 2.60 (s, 3H), 1.46 (s, 9H).

IR (nujol, cm$^{-1}$): 1723.

MS (m/z): 462 [MH]$^+$ 2Cl; 406 [MH−tBu+H]$^+$; 362 [MH-BOC+H]$^+$.

Intermediate 21

[6-Chloro-5(2-hydroxyethyl)-2-methylpyrimidin-4-yl]-(2-chloro-4-trifluoromethylphenyl)-carbamic acid tert-butyl ester A solution of intermediate 20 (462 mg) in CH$_2$Cl$_2$ (9 mL) and CH$_3$OH (1 mL) was ozonized (5 g.h$^{-1}$) at −78° C. for 20 min. When all the allyl pyrimidine had disappeared (according to TLC in cHex/EtOAc 7:3), the reaction mixture was first flushed with oxygen and then with nitrogen for 5 min. To the cooled reaction mixture was added NaBH$_4$ (148 mg) and the temperature was allowed to warm up to 22° C. The solution was stirred for 1.5 hr at r.t. It was then diluted with water (10 mL) and extracted with CH$_2$Cl$_2$ (3×110 nL). The combined organic extracts were dried over anh.

Na₂SO₄, filtered and concentrated to dryness in vacuo. The crude product was purified by flash chromatography (silica gel, cHex/EtOAc 90:10) to give the title compound (344 mg) as a white solid.

NMR ($^1$H, CDCl$_3$): δ 7.75 (d, 1H), 7.57 (d, 1H), 7.51 (dd, 1H), 3.95 (m, 2H), 3.05 (t, 2H), 2.59 (s, 3H), 1.85 (bs, 1H), 1.46 (s, 9H).

IR (nujol, cm$^{-1}$): 1718, 1672.

MS (m/z): 466 [MH]$^+$; 410 [MH−tBu+H]$^+$; 366 [MH−Boc+H]$^+$

Intermediate 22

Methanesulfonic acid 2-[4-chloro-6-(2-chloro-4-trifluoromethylphenylamino)-2-methyl pyrimidin-5-yl]ethyl ester To a solution of intermediate 21 (344 mg) in anh. CH$_2$Cl$_2$ (5 mL), at r.t, under N$_2$, was added Et$_3$N (515 μl) and CH$_3$SO$_2$Cl (110 μl). The reaction was stirred at r.t. for 18 hr. Water (15 mL) and CH$_2$Cl$_2$ (15 mL) were then added, the phases were separated and the aqueous layer was extracted with additional CH$_2$Cl$_2$ (2×5 mL). The combined organic extracts were dried over anh. Na$_2$SO$_4$, filtered and concentrated in vacuo.

A solution of the obtained oil in 20% TFA in CH$_2$Cl$_2$ (4 mL) was stirred at r.t. for 2 hr. The solvent was removed in vacuo and the residue was redissolved in EtOAc (10 mL) and saturated NaHCO$_3$ (10 mL), and the layers were separated. The aqueous layer was extracted with EtOAc (3×10 mL), and the combined organic extracts were dried over anh. Na$_2$SO$_4$, filtered and concentrated to dryness in vacuo to deliver the title compound (310 mg) as a yellow solid.

NMR ($^1$H, CDCl$_3$): δ 8.68 (d, 1H), 7.70 (s, 1H), 7.65 (bs, 1H), 7.58 (d, 1H), 4.55 (t, 2H), 3.27 (t, 2H), 2.99 (s, 3H), 2.61 (s, 3H).

IR (CDCl$_3$, cm$^{-1}$): 1323, 1177.

MS (m/z): 444 [MH]$^+$.

Intermediate 23

4-Chloro-7-(2-chloro-4-trifluoromethylphenyl)-2-methyl-6,7-dihydro-5H-pyrrolo[2,3-d]pyrimidine To a solution of intermediate 22 (310 mg) in anh. THF (8 mL) was added, at r.t., under N$_2$, NaH (80% mineral oil, 32 mg). The reaction was stirred for 2 hr at 60° C. The solution was diluted with water (10 mL) and extracted with EtOAc (2×15 mL). The combined organic extracts were dried over anh. Na$_2$SO$_4$, filtered and concentrated in vacuo. The crude product was purified by flash chromatography (silica gel, cHex/EtOAc 90:10) to give the title compound (197 mg) as a white solid.

NMR ($^1$H, CDCl$_3$): δ 7.77 (m, 1H), 7.62-7.55 (m, 2H), 4.11 (t, 2H), 3.24 (t, 2H), 2.46 (s, 3H).

MS (m/z): 347 [MH]$^+$, 312 [M−Cl]$^+$.

Intermediate 24

[6-Chloro-2-methyl-5-(2-oxoethyl)-pyrimidin-4-yl]-(2,4-dichlorophenyl)carbamic acid-tert-butyl ester A solution of intermediate 4 (300 mg) in CH$_2$Cl$_2$ (10 mL) was ozonized (5 g.h$^{-1}$) at −78° C. for 10 min. When all the allyl pyrimidine had disappeared (TLC), the reaction mixture was first flushed with oxygen and then with nitrogen for 20 min. To the cooled reaction mixture was added (CH$_3$)$_2$S (256 μl) and the temperature was allowed to warm up to 22° C. The solution was stirred for 18 hr at r.t. The solvent was removed in vacuo and the crude product was purified by flash chromatography (silica gel, cHex/EtOAc 18.5:1.5) to give the title compound (250 mg) as a white solid.

NMR ($^1$H, CDCl$_3$): δ 9.59 (s, 1H), 7.77+7.57 (d+d, 1H), 7.47+7.37 (dd+dd, 1H), 7.47+7.41 (d+d, 1H), 3.83 (s, 2H), 2.46 (s, 3H), 1.33 (bs, 9H).

IR (nujol, cm$^{-1}$): 1729.

MS (m/z): 430 [MH]$^+$, 3Cl; 452 [MH+Na]$^+$, 330 [MH−Boc+H]$^+$

Intermediate 25

[6-Chloro-5-(3-methoxyallyl)-2-methylpyrimidin-4-yl]-(2,4-dichlorophenyl)carbamic acid tert-butyl ester To a stirred suspension of (methoxy-methyl) triphenylphosphonium chloride (198 mg) in 3 mL of dry THF was added, at 0° C., under N$_2$, n-BuLi 1.6M in hexane (2.8 eq) dropwise. The mixture was allowed to stir for 10 min before a solution of intermediate 24 (83 mg) in dry THF (1 mL) was added. The reaction mixture was allowed to warm slowly to r.t. and left stirring for 3 hr. The mixture was quenched with water (5 mL) and extracted with EtOAc (3×8 mL). The combined organic extracts were dried over anh. Na$_2$SO$_4$, filtered and concentrated to dryness in vacuo. The crude product was purified by flash chromatography (silica gel, cHex/EtOAc 9:1) to give the title compound (39 mg) as a white solid.

NMR ($^1$H, CDCl$_3$): δ 7.50-7.47 (s, 1H), 7.28-7.15 (dd/d, 1+1H), 6.37-5.98 (d, 1H, J$_{trans}$=13 Hz, J$_{cis}$=6 Hz), 4.58-4.34 (m, 1H, J$_{trans}$=13 Hz, J$_{cis}$=6 Hz), 3.55-3.37 (d, 2H), 3.60-3.44(s, 3H), 2.58-2.53 (s, 3H), 1.55 (s, 9H).

MS (m/z): 458 [MH]$^+$, 3Cl; 480[MH+Na]$^+$, 402 [MH−tBu+H]$^+$, 358 [MH−Boc+H]+

Intermediate 26

[6-Chloro-2-methyl-5-(3-oxopropyl)pyrimidin-4-yl-(2,4-dichlorophenyl)carbamic acid tert-butyl ester Intermediate 25 (39 mg) was stirred at r.t. with 4 mL of 4:1 THF-2N HCl for 78 hr. The mixture was then diluted with H$_2$O (4 mL) and extracted with EtOAc (4×5 mL). The combined organic extracts were dried over anh. Na$_2$SO$_4$, filtered and concentrated to dryness in vacuo. The crude product was purified by flash chromatography (silica gel, cHex/EtOAc 19:1) to give the title compound (26 mg) as a white solid.

NMR ($^1$H, CDCl$_3$): δ 9.83 (s, 1H), 7.45 (d, 1H), 7.3-7.2 (d/dd, 2H), 3.00 (m, 2H), 2.92 (m, 2H), 2.55 (s, 3H), 1.41 (s, 9H).

MS (m/z): 444[MH]$^+$, 3Cl; 466[MH+Na]$^+$, 344[MH−Boc+H]$^+$

Intermediate 27

[6-Chloro-5-(3-hydroxypropyl)-2-methylpyrimidin-4-yl]-(2,4-dichlorophenyl)carbamic acid tert-butyl ester To a solution of intermediate 26 (21 mg) in anh.CH$_3$OH (1 mL), at r.t., under N$_2$ was added NaBH$_4$ (4 eq). The reaction mixture was stirred for 1 hr. The solvent was removed in vacuo and the residue was redissolved in EtOAc (10 mL)/H$_2$O (10 mL), and the layers were separated. The aqueous layer was extracted with EtOAc (3×10 mL), and the combined organic extracts were dried over anh. Na$_2$SO$_4$, filtered, and concentrated in vacuo to afford the title compound (15 mg) as a white solid.

NMR ($^1$H, CDCl$_3$): δ 7.49 (m, 1H), 7.23 (m, 2H), 3.71 (m, 2H), 2.78 (m, 2H), 2.60 (s, 3H), 1.82 (m, 2H), 1.45 (s, 9H).

MS (m/z): 446 [MH]+, 3Cl; 468 [MH+Na]+, 346 [MH−Boc+H]+, 390 [MH−tBu+H]+

Intermediate 28

Methanesulfonic acid 3-{4-[tert-butoxycarbonyl(2,4-dichlorophenyl)amino]-6-chloro-2-methylpyrimidin-5-yl}propyl ester To a solution of intermediate 27 (13 mg) in anh. $CH_2Cl_2$ (1 ML), at r.t, under $N_2$, was added $Et_3N$ (20 µl) and $CH_3SO_2Cl$ (4 µl). The reaction was stirred at r.t. for 18 hr. The reaction mixture was diluted with water (5 mL) and extracted with EtOAc (3×5 mL). The combined organic extracts were dried over anh. $Na_2SO_4$, filtered and concentrated in vacuo. The crude product was purified by flash chromatography (silica gel, cHex/EtOAc 75/25) to give the title compound (25 mg) as a white solid.

NMR (1H, $CDCl_3$): δ 7.48 (t, 1H), 7.24 (m, 2H), 4.28 (t, 2H), 3.02 (s, 3H), 2.80 (m, 2H), 2.58 (s, 3H), 2.03 (m, 2H), 1.42 (s, 9H).

MS (m/z): 524 [MH]+, 3Cl; 546 [MH+Na]+, 468 [MH−tBu+H]+, 424 [MH−Boc+H]+.

Intermediate 29

Methanesulfonic acid 3-[4-chloro-6-(2,4-dichlorophenylamino)-2-methylpyrimidin-5-yl]-propyl ester A solution of intermediate 28 (50 mg) in TFA 20% $CH_2Cl_2$ (4 mL) was stirred at r.t. for 2 hr. The solvent was removed in vacuo and the residue was dissolved in EtOAc (10 mL) and saturated $NaHCO_3$ (10 mL), and the layers were separated. The aqueous layer was extracted with EtOAc (3×10 mL), and the combined organic extracts were dried over anh. $Na_2SO_4$, filtered and concentrated to dryness in vacuo to deliver the title compound (40 mg) as a white solid.

NMR ($^1H$, $CDCl_3$): δ 8.49 (d, 1H), 7.44 (d, 2H), 7.31 (dd, 2H), 7.22 (d, 1H), 4.39 (t, 2H), 3.05 (s, 3H), 2.93 (m, 2H), 2.56 (s, 3H), 2.13 (m, 2H).

MS (m/z): 424[MH]+, 3Cl

Intermediate 30

4-Chloro-8-(2,4-dichlorophenyl)-2-methyl-5,6,7,8-tetrahydropyrido[2,3d]pyrimidine To a solution of intermediate 29 (40 mg) in anh. THF (2 mL) was added, at r.t., under $N_2$, NaH (95%/mineral oil, 5 mg). The reaction mixture was stirred for 2 hr at r.t. The solution was diluted with water (8 mL) and extracted with EtOAc (2×8 mL). The combined organic extracts were dried over anh. $Na_2SO_4$, filtered and concentrated to dryness in vacuo. The crude product was purified by flash chromatography (silica gel, cHex/EtOAc 9:1) to give the title compound (25 mg) as a white solid.

NMR ($^1H$, $CDCl_3$): δ 7.51 (d, 1H), 7.32 (dd, 2H), 7.20 (d, 2H), 3.60 (m, 2H), 2.87 (m, 3H), 2.29 (s, 3H), 2.13 (m, 2H).

Intermediate 31

2-(2,4-dichlorophenyl)hexanedioic acid 6-ethyl ester 1-methyl ester

To a solution of i-$Pr_2NH$ (0.921 mL, 1.2 eq) in anh. THF (22 mL), at 0° C., under $N_2$, was added a 1.6 M solution of BuLi in hexane (3.42 mL, 1 eq) and the mixture was stirred at 0° C. for 10 min. It was then cooled to −78° C. and a solution of methyl 2,4-dichlorophenylacetate (1.2 g, 5.478 mmol) in anh. THF (3.3 mL) was added dropwise. The mixture was stirred at −78° C. for 45 min before the addition of a solution of ethyl 4-iodobutyrate (1.72 g, 1.3 eq) in anh. THF (2 mL). The cooling bath was then removed and the mixture was stirred at r.t. for 4 hr. The solvents were evaporated under reduced pressure. The residue was dissolved in $CH_2Cl_2$, washed with water (2×25 mL) and brine (1×25 mL) and dried over anh. $Na_2SO_4$. The solids were filtered and the solvent evaporated. The crude product was purified by flash chromatography (silica gel, cHex/EtOAc 9:1). Mixed fractions were repurified with the same eluent. The title compound was obtained as a pale yellow oil (1.36 g, 4.088 mmol, 75%).

NMR ($^1H$, $CDCl_3$): δ 7.63 (d, 1H), 7.44 (dd, 1H), 7.40 (d, 1H), 4.05 (dd, 1H), 4.01 (q, 2H), 3.59 (s, 3H), 2.28 (dt, 2H), 2.01 (m, 1H), 1.74 (m, 1H), 1.47 (m, 1H), 1.35 (m, 1H), 1.14 (t, 3H).

IR (film, $cm^{-1}$): 1736.

MS (m/z): 332 [M]+, 300 [M-$CH_3OH$]+.

Intermediate 32

3-(2,4-Dichlorophenyl)-2-oxo-cyclopentanecarboxylic acid methyl ester

Sodium (376 mg, 4 eq) was added portionwise, under $N_2$, to anh. MeOH (5 mL). After consumption of metallic sodium, MeOH was evaporated under a nitrogen flux. Anh. toluene (30 mL) was then added to the residue, followed by a solution of intermediate 31 (1.36 g, 4.088 mmol) in anh. toluene (30 mL). The mixture was heated at 90° C. for 45 min. The reaction mixture was acidified with glacial AcOH, diluted with EtOAc and washed with water (2×20 mL) and with diluted aqueous $NaHCO_3$ (2×20 mL) and dried over anh. $Na_2SO_4$. The solids were filtered and the solvent evaporated. The title compound was obtained as a pale yellow oil (1 g, 3.48 mmol, 85%), as a mixture of two diastereoisomers in a 7:3 ratio and was used in the following step without further purification.

NMR (1H, $CDCl_3$): δ 7.38 (m, 1H), 7.19 (m, 1H), 7.06, 7.01, (2d, 1H), 3.93-3.85, 3.78 (m+dd, 1H), 3.79, 3.76 (2s, 3H), 3.49-3.44, 3.40 (m+dd, 1H), 2.60-1.90 (m, 4H).

IR (film, $cm^{-1}$): 1755, 1732.

MS (m/z): 286 [M]+, 226, 219, 172.

Intermediate 33

4-Hydroxyl-7-(2,4-dichlorophenyl)-2-methyl-6,7-dihydro-5H-cyclopentapyrimidine

Sodium (240 mg, 3 eq) was added portionwise to anh. MeOH (6 mL) under $N_2$. After consumption of metallic sodium acetamidine hydrochloride (1.04 g, 3 eq) was added. After 10 min of stirring the precipitated NaCl was filtered off and washed with anh. MeOH (2 mL). The solution of free acetamidine was added to neat intermediate 32 (1 g, 3.483 mmol) and the mixture was stirred at r.t. for 2 days and then at 70° C. for 7 hr. The solvent was evaporated and the crude product was purified by flash chromatography (silica gel, gradient: $CH_2Cl_2$/MeOH 98:2 to 95:5). The pure title compound was obtained as a white solid (455 mg, 1.54 mmol, 44%).

NMR ($^1H$, DMSO-$d_6$): δ 12.31 (s, 1H), 7.60 (d, 1H), 7.34 (dd, 1H), 7.04 (d, 1H), 4.54 (t, 1H), 2.75-2.60 (2m, 2H), 2.58-2.50 (m, 1H), 2.20 (s, 3H), 1.80-1.72 (m, 1H).

MS (m/z): 295 [MH]+.

Intermediate 34

4-Chloro-7-(2,4-dichlorophenyl)-2-methyl-6,7-dihydro-5H-cyclopentapyrimidine

Intermediate 33 (453 mg, 1.535 mmol) was suspended in POCl$_3$ (16 mL) and the mixture was refluxed for 2.5 hr. The excess POCl$_3$ was then evaporated and the residue was dissolved in CH$_2$Cl$_2$. A few drops of conc. NH$_4$OH were added and the mixture was diluted with water and CH$_2$Cl$_2$. The phases were separated and the aqueous layer was extracted with CH$_2$Cl$_2$ (3×20 mL). The combined organic layers were washed with water and brine (2×20 mL) and dried over anh. Na$_2$SO$_4$. The solids were filtered and the solvent evaporated. The crude title compound was obtained as a brown oil (378 mg, 1.2 mmol, 79%) and was used in the next step without further purification.

NMR ($^1$H, CDCl$_3$): δ 7.44 (d, 1H), 7.19 (dd, 1H), 6.82 (d, 1H), 4.83 (t, 1H), 3.05 m, 2H), 2.79 (m, 1H), 2.68 (s, 3H), 2.00 (m, 1H).

MS (m/z): 313 [MH]$^+$.

Intermediate 35

2,4-Dichloro-1-cyclohex-1-enyl benzene

To a solution of n-butyl lithium 1.6M in hexanes (13.8 mL, 1.4 eq) in anh. THF (40 mL) at −78° C., under N$_2$, was added dropwise HN(iPr)$_2$ (3.32 mL, 1.5 eq). After stirring for 15 min, a solution of cyclohexanone (1.6 mL, 15.45 mmol) in anh. THF (4 mL) was added. After stirring for 15 min the enolate solution was warmed to room temperature and stirred for 2 h. It was then cooled to −78° C. and a solution of N-phenyl triflimide (6.1 g, 17 mmol, 1.1 eq) in anh. THF (20 mL) was added to the enolate at −78° C. The reaction mixture was warmed to 0° C. and stirred for 4 h. The resulting solution was poured into water, the volume was reduced under vacuum and the residue was taken up in EtOAc and washed with H$_2$O (3×25 mL). The organic phase was dried over anh. Na$_2$SO$_4$, the solids were filtered and the solvent evaporated. The triflate was used as such in the following step.

A mixture of the crude triflate obtained above (3 g), 2,4-dichloro-benzeneboronic acid (3.2 g, 1.1 eq), 1,1'-bis(diphenylphosphino-ferrocene)PdCl$_2$ (315 mg, 0.025 eq) and K$_2$CO$_3$ (4.2 g, 2 eq), in toluene/acetone/water (26/26/6,5 mL) was heated at 80° C. for 3 h. The mixture was then treated with 1N NaOH (15 mL) and H$_2$O$_2$ 30% (10 mL) for 20 min at r.t. to reduce the residual borane. The product was extracted with toluene, washed with brine and dried over anh. Na$_2$SO$_4$. The solids were filtered, the solvent was evaporated and the residue was purified by flash chromatography (silica gel, 100% cHex). The title compound was obtained as a clear oil (2.18 g, 9.58 mmol, 62%)

NMR ($^1$H, DMSO): δ 7.6 (d, 1H), 7.4 (dd, 1H), 7.27 (d, 1H), 5.69 (sett, 1H), 2.24 (m, 2H), 2.16 (m, 2H), 1.72 (m, 2H), 1.69 (m, 2H).

MS (m/z): 226 [M]$^+$ 2Cl.

Intermediate 36

1-(2,4-Dichlorophenyl)-7-oxa-bicyclor[4.1.0]heptane

A solution of m-CPBA (2.25 g, 3 eq) in EtOAc (6 mL) was added dropwise to a stirred 40 solution of intermediate 35 (1 g, 4.4 mmol) in EtOAc (6 mL) at 0° C., under N$_2$. The reaction mixture was stirred at 0° C. for 1 h and at r.t. for 12 h. When the reaction was complete (by t.l.c.) the reaction mixture was washed with 1N NaOH (3×10 mL) and H$_2$O (2×10 mL). It was then dried over anh. Na$_2$SO$_4$, the solids were filtered and the solvent evaporated. The title compound was obtained as a clear oil (940 mg, 3.87 mmols, 89%).

NMR ($^1$H, DMSO): δ 7.60 (m, 1H), 7.39 (m, 2H), 3.09 (t, 1H), 1.93 (m, 4H), 1.3

MS (m/z): 242 [M]$^+$ 2Cl.

Intermediate 37

2-(2,4-Dichlorophenyl)-cyclohexanone

A solution of intermediate 36 (940 mg, 3.8 mmols) in EtOH (5 mL) was treated with conc. H$_2$SO$_4$ (1 mL) dissolved in H$_2$O (1 mL) and EtOH (5 mL). The solution was refluxed for 24 h and the ETOH was evaporated The residue was dissolved in EtOAc, washed with sat.aq. NaHCO$_3$ and H$_2$O. It was then dried over anh. Na$_2$SO$_4$, the solids were filtered and the solvent evaporated. The crude oil was purified by flash chromatography (silica gel, cHex/EtOAc 95:5). The title compound was obtained as a clear solid (345 mg, 1.42 mmol, 37%)

NMR ($^1$H, CDCl$_3$): δ 7.40 (d, 1H), 7.25 (dd, 1H), 7.15 (d, 1H), 4.06 (dd, 1H), 2.55 (m, 2H), 2.20 (m, 2H), 2.0-1.7 (m, 2H).

IR (CDCl$_3$, cm$^{-1}$): 2926, 2854, 1713.

MS (m/z): 242 [M]$^+$ 2Cl.

Intermediate 38

3-(2,4-Dichlorophenyl)-2-oxo-cyclohexanecarboxylic acid ethyl ester

To a suspension of NaH 80%/oil (48 mg, 1.1 eq) in anh. THF (2 mL), at 0° C., under N$_2$, was added intermediate 37 (350 mg, 1.44 mmol) dissolved in anh. THF (2.5 mL). After stirring for 15 min, to this solution was added dropwise a solution of LDA 0.5M/THF (3.2 mL, 1.1 eq). After 15 min the solution was cooled to −78° C. and ethyl cyanoformate (0.16 mL, 1.1 eq) was added dropwise. The reaction mixture was stirred at −78° C. for 20' and was then poured into water and ice and extracted with CH$_2$Cl$_2$ (3×10 mL). The combined organic extracts were dried over anh. Na$_2$SO$_4$, the solids were filtered and the solvent evaporated. The crude oil was purified by flash chromatography (silica gel, cHex/EtOAc 95:5). The title compound was obtained as a clear oil (150 mg, 0.48 mmol, 33%) as a mixture of O-keto-ester and its enolic form in a 65:35 ratio.

NMR ($^1$H, DMSO): δ 12.18 (s, 1H), 7.55 (d, 1H), 7.53 (d, 2H), 7.4-7.36 (dd, 2H), 7.32 (d+t, 2H), 7.23 (d, 1H), 4.23 (m, 2H), 4.11. (n, 2H), 4.03 (ta, 1H), 3.84 (ta, 1H), 2.4-1.8 (m, 12H), 1.27 (t+t, 6H).

IR (film, cm$^{-1}$): 3417, 1653, 1614.

MS (m/z): 314 [MH]$^+$ 2Cl.

Intermediate 39

8-(2,4-Dichlorophenyl)-2-methyl-5,6,7,8-tetrahydro-quinazolin-4-ol

Sodium (20 mg, 1.84 eq) was added portionwise, under N$_2$, to anh. MeOH (2 mL). After consumption of metallic sodium, acetamidine hydrochloride (88 mg, 1.84 eq) was added to 40 the solution. After 10 min the solid NaCl was filtered off and to the clear solution was added intermediate 38 (150 mg, 0.48 mmol) dissolved in anh. MeOH (2 m]L). The reaction mixture was stirred at r.t. for 96 h and the solvent was then evaporated. The residue was purified by flash chromatography (silica gel, CH$_2$Cl$_2$/MeOH 95:5). The title compound was obtained as a white solid (92 mg, 0.30 mmol, 62%).

NMR (¹H, CDCl₃): δ 11.2 (broad, 1H), 7.42 (d, 1H), 7.13 (dd, 1H), 6.72 (d, 1H), 4.34 (t, 1H), 2.65 (m, 1H), 2.56 (m, 1H), 2.34 (s, 3H), 2.07 (m, 1H), 1.92 (m, 1H), 1.72 (m, 1H), 1.65 (m, 1H).

MS (m/z): 309 [MH]⁺ 2Cl

Intermediate 40

4-Chloro-8-(2,4-dichlorophenyl)-2-methyl-5,6,7,8-tetrahydroquinazoline

Intermediate 39 (95 mg, 0.29 mmol) was dissolved in POCl₃ (3 mL) and the solution was refluxed for 3 h. The POCl₃ was evaporated, the residue was dissolved in CH₂Cl₂ and poured into ice and conc. NH₄OH. The organic phase was separated and dried over anh. Na₂SO₄. The solids were filtered and the solvent evaporated. The crude product was purified by flash chromatography (silica gel, cHex/EtOAc 8:2) to obtain the title compound as a white solid (88 mg, 0.27 mmol, 93%).

NMR (¹H, CDCl₃): δ 7.42 (d, 1H), 7.13 (dd, 1H), 6.58 (d, 1H), 4.54 (t, 1H), 2.83 (m, 2H), 2.56 (s, 3H), 2.14 (m, 1H), 2.00 (m, 1H), 1.84 (m, 2H).

MS (m/z): 327 [MH]⁺ 3Cl

Intermediate 41

2-(2,4-Dimethoxyphenyl)cyclopentanone

A solution of 1-bromo-2,4-dimethoxybenzene (345 μL, 1.2 eq.) in dry THF (0.5 mL) was added dropwise, under N₂, to a suspension of Mg turnings (64 mg, 1.3 eq.) in dry THF (0.7 mL) and in presence of a catalitic amount of I₂. The reaction mixture was stirred at reflux for 1 hr and then cooled down to 0° C. To this mixture was added dropwise a solution of 2-chlorocyclopentanone (0.2 mL, 2 mmol) in anh. THF (0.5 mL) and the reaction mixture was heated to reflux for 2 hr. The mixture was allowed to cool at r.t., it was diluted with Et₂O and slowly mixed with ice and 1M HCl. The organic layer was then separated, washed twice with brine and dried over anh. Na₂SO₄. The solids were filtered and the solvent evaporated. The crude red oil was purified by flash chromatography (silica gel, cHex/EtOAc 8:2) to give the title compound (297 mg, 67%) as a yellow oil.

NMR (¹H, CDCl₃): δ 6.97 (d, 1H), 6.44 (m, 2H), 3.78 (s, 3H), 3.74 (s, 3H), 3.30 (dd, 1H), 2.4-2.3 (m, 3H), 2.13-2.04 (m, 2H), 1.86 (m, 1H).

IR (film, cm⁻¹): 1738.

MS (m/z): 220 [M]⁺.

Intermediate 42

3-(2,4-Dimethoxyphenyl)-2-oxocyclopentanecarboxylic acid methyl ester

To a solution of freshly distilled diisopropylamine (148 μL, 1.2 eq.) in anh. THF (3.5 mL), at 0° C., under N₂, was added 1.6M n-BuLi in hexane (660 μL, 1.12 eq) and the resulting mixture was stirred for 10 min and then cooled down at −78° C. A solution of intermediate 41 (195 mg, 0.88 mmol) in anh. THF (1 mL) was added dropwise and the reaction was stirred for 15 min. Methyl chloroformate (75 μL, 1.eq.) was then added to the enolate solution and the reaction flask was stirred for 15 min. The cold reaction mixture was poured into 0.5N HCl (10 mL) and diethyl ether (10 mL). The phases were separated and the organic layer was washed with saturated NaHCO₃, saturated NaCl and it was then dried over anh. Na₂SO₄. The solids were filtered and the solvent evaporated. The crude oil was purified by flash chromatography (silica gel, cHex/Et₂O 7:3) and the title compound was obtained as a yellow oil (66 mg, 27%)

NMR (¹H, CDCl₃): δ 6.97 (d, 1H), 6.44-6.42 (m, 2H), 3.8-3.69 (m, 9H), 3.41 (m, 2H), 2.31 (m, 1H), 2.08 (m, 1H).

IR (film, cm⁻¹): 1755, 1728.

MS (m/z): 278 [M]⁺.

Intermediate 43

7-(2,4-Dimethoxyphenyl)-2-methyl-6,7-dihydro-5H-cyclopentapyrimidin-4-ol

Acetamidine hydrochloride (50 mg, 2.3 eq.) was added to a solution of freshly prepared MeONa (37 mg, 2.3 eq.) in anh. MeOH (1 mL). The resulting suspension was filtered and added to a flask containing intermediate 42 (65 mg, 0.23 mmol) in anh. MeOH (1 mL). The reaction mixture was stirred for 1 day and then a second portion of the free acetamidine was prepared as described above and added to the reaction flask. After stirring for 2 days, the solution was concentrated in vacuo and the crude oil was purified by flash chromatography (silica gel, 100% EtOAc). The title compound was obtained as a white solid (35 mg, 53%)

NMR (¹H, CDCl₃): δ 10.44 (bs, 1H), 6.79 (d, 1H), 6.46 (d, 1H), 6.41 (dd, 1H), 4.53 (t, 1H). 3.78 (s, 6H), 2.88 (m, 1H), 2.78 (m, 1H), 2.55 (m, 1H), 2.41 (s, 3H), 1.90 (m, 1H)

MS (m/z): 287 [MH]⁺.

Intermediate 44

4-Chloro-7-(2,4-dimethoxyphenyl)-2-methyl-6,7-dihydro-5H-cyclopentapyrimidine

A solution of intermediate 43 (21 mg, 0.07 mmol) in POCl₃ (1 mL) was heated at 100° C. for 3 hr and then concentrated in vacuo. The crude oil was diluted with EtOAc and washed with conc. NH₄OH. It was then dried over anh. Na₂SO₄, the solids were filtered and the solvent was evaporated to give the title compound (20.6 mg, 90%) as an orange oil, which was used as such in the next step.

NMR (¹H, CDCl₃): δ 6.82 (d, 1H), 6.40 (m, 2H), 4.6 (dd, 1H), 3.8 (s, 3H), 3.7 (s, 3H) 3.1-2.85 (m, 2H), 2.65 (s, 3H), 2.60 (m, 1H), 2.05 (m, 1H).

Intermediate 45

(4,6-Dichloro-2-methyl-pyrimidin-5-yl)acetic acid methyl ester

Sodium (1.74 g, 3 eq) was added portionwise to anh. MeOH (60 mL), at 0° C., under N₂. After consumption of metallic sodium, acetamidine hydrochloride (7.06 g, 3 eq) was added. After 20 min. of stirring the precipitated NaCl was filtered off. A solution of 2-ethoxycarbonylsuccinic acid diethyl ester (6.04 g, 24.5 mmol) in anhydrous CH₃OH (20 mL) was added to the solution of free acetamidine and the mixture was stirred at r.t. for 2 days. The reaction mixture was concentrated to dryness in vacuo and the yellow foam (8.69 g) obtained was then mixed with POCl₃ (6 eq) and CH₃CN (10 Vol.) and heated at reflux for 18 hours. The resulting solution was cooled to r.t. and poured slowly into ice/water and conc. NH₄OH with vigorous stirring. The product was extracted with EtOAc (3×). The combined organic extracts were washed with brine, dried over anh. Na₂SO₄, filtered and concentrated in vacuo.

The crude oil was purified by flash chromatography (silica gel, cHex/EtOAc 8:2). The title compound was obtained as a yellow solid (98% in two steps)

NMR (¹H, CDCl₃): δ 5.85 (m, 1H), 5.15 (dq, 1H), 5.11 (dq, 1H), 3.61 (dt, 2H), 2.67 (s, 3H).

MS (m/z): 202 [M]⁺ (2Cl).

Intermediate 46

(4,6-Dichloro-2-methylpyrimidin-5-yl)acetaldehyde

To a solution of intermediate 45 (300 mg, 1.276 mmol) in anh. CH₂Cl₂ (6 mL), at −78° C., under N₂, was added DIBAl-H (1M solution in hexane, 1.8 eq, 2.3 mL). After the addition was complete the reaction mixture was stirred at −78° C. for 1 hr and at −55° C. for 2 hr. The reaction mixture was poured into a solution of HCl 0.5N in ice and extracted with CH₂Cl₂ (3×). The combined organic extracts were dried over anh. Na₂SO₄, the solids were filtered and the solvent evaporated. The crude product was purified by flash chromatography (silica gel, cHex/EtOAc 8:2) to give the title compound as a colourless oil (160 mg, 62%).

NMR (¹H, CDCl₃): δ 9.78 (s, 1H), 4.09 (s, 2H), 2.70 (s, 3H).

MS (m/z): 204 [M]⁺ (2Cl).

Intermediate 47

4,6-Dichloro-5-(3-methoxyallyl)-2-methylpyrimidine

To a stirred suspension of (methoxy-methyl) triphenylphosphonium chloride (675 mg, 2 eq.) in anh. THF (6 mL) was added, at 0° C., under N₂, n-BuLi 1.6M in hexane (2 eq., 1.22 mL) dropwise. The mixture was allowed to stir for 30 min before a solution of intermediate 46 (200 mg, 0.985 mmol) in anh. THF (1 mL) was added at −78° C. The reaction mixture was allowed to warm slowly to r.t. and left stirring for 3 hr. The mixture was quenched with water and extracted with EtOAc (3×). The combined organic extracts were dried over anh. Na₂SO₄, the solids were filtered and the solvent evaporated. The crude product was purified by flash chromatography (silica gel, cHex/EtOAc 9:1) to give the title compound as a white solid (85 mg, 40%).

NMR (¹H, CDCl₃): δ 6.55 (bd, 1H), 4.75 (m, 1H), 3.51 e 3.47(s e dd, 5H), 2.66 (s, 3H).

MS (m/z): 233 [MH]⁺ (2Cl).

Intermediate 48

3-(4,6-dichloro-2-methyl-pyrimidin-5-yl)propionaldehyde

Intermediate 47 (125 mg, 0.345 mmol) was stirred at r.t. with 12 mL of a 1:3 mixture of THF-2N HCl for 15 hr. The mixture was then diluted with H₂O and extracted with EtOAc (3×). The combined organic extracts were dried over anh. Na₂SO₄, the solids were filtered and the solvent evaporated. The crude product was purified by flash chromatography (silica gel, cHex/EtOAc 8:2) to give the title compound as a white solid (75 mg, 99%).

NMR (¹H, CDCl₃): δ 9.87 (s, 1H), 3.18 (m, 2H), 2.78-2.67 (m-s, 5H).

MS (m/z): 218 [M]⁺ (2Cl).

Intermediate 49

3-(4,6-Dichloro-2-methylpyrimidin-5-yl)propan-1-ol

To a solution of intermediate 48 (75 mg, 0345 mmol) in anh. CH₃OH (6 mL) was added NaBH₄ (52 mg, 4 eq) at 0° C. The reaction was stirred for 1 hr. The solvent was removed in vacuo and the residue was taken up in EtOAc/H₂O, and the layers were separated. The aqueous layer was extracted with EtOAc (3×), and the combined organic extracts were dried over anh. Na₂SO₄. The solids were filtered and the solvent evaporated to afford the title compound as a white solid. (75 mg, 99%)

NMR (¹H, CDCl₃): δ 4.59 (t, 1H), 3.46 (q, 2H), 2.80 (dd, 2H), 2.54 (s, 3H), 1.82 (m, 2H).

MS (m/z): 202 [M−18]⁺ (2Cl).

Intermediate 50

Methanesulfonic acid 3-(4,6-dichloro-2-methylpyrimidin-5-yl)propyl ester

To a solution of intermediate 49 (104 mg, 0.473 mmol) in anh. CH₂Cl₂ (10 mL), at r.t, under N₂, was added Et₃N (4 eq., 262 µl) and CH₃SO₂Cl (2.5 eq., 91 µl). The reaction was stirred at r.t. for 3 hr. The reaction mixture was diluted with water and extracted with CH₂Cl₂ (3×). The combined organic extracts were dried over anh. Na₂SO₄, the solids were filtered and the solvent evaporated. The crude product was purified by flash chromatography (silica gel, cHex/EtOAc 8:2) to give the title compound as a white solid (134 mg, 95%).

NMR (¹H, CDCl₃): δ 4.31 (t, 2H), 3.02 (s, 3H), 2.95 (m, 2H), 2.62 (s, 3H), 2.03 (m, 2H).

MS (m/z): 299 [MH]⁺ (2Cl).

Intermediate 51

4-Chloro-8-(2,4-bis-trifluoromethylphenyl)-2-methyl-5,6,7,8-tetrahydropyrido-[2,3d]pyrimidine To a solution of 2,4-bis-trifluoromethyl-aniline (134 mg, 0.448 mmol) in anh. DMF (18 mL) was added, at 0° C., under N₂, NaH (80% mineral oil, 2 eq, 1.6 mg). The reaction was stirred for 30 min at r.t. and then, at 0° C., was added a solution of intermediate 50 in anh. DMF. It was stirred at room temperature for 1 hr. The solution was diluted with water and extracted with EtOAc (3×). The combined organic extracts were dried over anh. Na₂SO₄, the solids were filtered and the solvent evaporated. The crude product was purified by flash chromatography (silica gel, Toluene/EtOAc 9:1) to give the title compound as a white solid (95 mg, 54%)

NMR (¹H, CDCl₃): δ 8.03 (s, 1H), 7.91 (dd, 1H), 7.42 (d, 1H), 3.62 (t, 2H), 2.92 (m, 1H), 2.83 (m, 1H), 2.26 (s, 3H), 2.14 (m, 2H).

MS (m/z): 396 [MH]⁺ (1Cl)

Intermediate 52

2-(4,6-Dichloro-2-methyl-pyrimidin-5-yl)-ethanol

To a solution of intermediate 45 (4.0 g, 0.017 mol) in anh. THF (60 mL), at −78° C., under N₂, was added DIBAl-H 1M/THF (52.5 mL, 3 eq) dropwise. After the addition was complete, the reaction mixture was stirred at −30° C. for 3 hr. A Rochelle salt solution was then added at 0° C. and the phases were separated. The aqueous layer was extracted with EtOAc (2×50 mL) and the combined organic extracts were dried over anh. Na₂SO₄. The solids were filtered and the solvent evaporated. The title compound was obtained as a clear oil (3.1 gr, 89%) and was used in the next step without further purification.

NMR (¹H, CDCl₃): δ 4.90 (t, 2H), 3.15 (t, 2H), 2.64 (s, 3H), 1.70 (bs, 1H).

MS (m/z): 207 [MH]⁺

Intermediate 53

5-[2-tert-Butyl-dimethyl-silanoxy)-ethyl]4,6-dichloro-2-methyl-pyrimidine

To a solution of intermediate 52 (3.1 g, 0.015 mol) in anh. DMF (100 mL), at 0° C., under N₂, were added imidazole (17 g, 17 eq), t-butyldimethylsilyl chloride (6.35 gr, 2.8 eq) and DMAP (catalytic amount). The solution was stirred at r.t. for 18 hr. EtOAc (100 mL) and sat.aq. NH₄Cl (50 mL) were added and the phases were separated. The organic layer was washed with sat.aq. NaCl (2×100 mL) and dried over anh. Na₂SO₄. The solids were filtered and the solvent evaporated. The crude compound was purified by flash chromatography (silica gel, cHex/EtOAC 9:1) to give the title compound as a clear oil (4.6 g, 95%).

NMR (¹H, CDCl₃): δ 3.86 (t, 2H), 3.12 (t, 2H), 2.66 (s, 3H), 0.85 (s, 9H), 0.01 (s, 6H).

MS (m/z): 321 [MH]⁺

Intermediate 54

(2,4-Bis-trifluoromethyl-phenyl)-{5-[2-(tert-butyl-dimethyl-silanoxy)-ethyl]-6-chloro-2-methyl-pyrimidin-4-yl}-amine To a solution of 2,4-bis-trifluoromethyl-aniline (984 µL, 1 eq) in anh. DMF (15 mL), at 0° C., under N₂, was added NaH 80%/oil (400 mg, 2.2 eq). The reaction mixture was stirred at 0° C. for 30 min and was then added to a solution of intermediate 53 (2 g, 6 mmol) in anh. DMF (15 mL) at r.t., under N₂. The reaction mixture was stirred at r.t. for 30 min. The excess NaH was carefully destroyed with sat.aq. NaCl and the reaction mixture was diluted with EtOAc. The phases were separated, the organic layer was washed with sat.aq. NaCl (2×30 mL) and dried over anh. Na₂SO₄. The solids were filtered and the solvent evaporated. The crude compound was purified by flash chromatography (silica gel, cHex/EtOAc 95:5→90:10).

The title compound was obtained as a clear oil (1.84 g, 56%).

NMR (¹H, CDCl₃): δ 8.61 (d, 1H), 8.04 (bs, 1H), 7.86 (s, 1H), 7.79 (d, 1H), 4.95 (t, 2H), 3.95 (t, 2H), 2.53 (s, 3H), 0.73 (s, 9H), −0.90 (s, 6H).

MS (m/z): 514 [MH]⁺

Intermediate 55

2-[4-(2,4-Bis-trifluoromethyl-phenylamino)-6-chloro-2-methyl-pyrimidin-5-yl]-ethanol To a solution of intermediate 54 (1.84 g, 3.58 mmols) in anh. DMF (30 mL), at r.t., under N₂, was added Et₃N.3HF (2.4 mL, 3 eq). The reaction mixture was stirred at r.t. for 18 hr. It was then diluted with cold sat.aq. NaCl (50 mL) and extracted with EtOAc (3×50 mL). The combined organic extracts were dried over anh. Na₂SO₄. The solids were filtered and the solvent evaporated. The title compound was obtained as a clear oil (1.4 gr, 98%) and was used in the next step without further purification.

NMR (¹H, CDCl₃): δ 8.59 (bs, 1H), 8.22 (d, 1H), 7.84 (s, 1H), 7.75 (d, 1H), 4.06 (t, 2H), 3.01 (t, 2H), 2.50 (s, 3H)

MS (m/z): 400 [MH]⁺

EXAMPLE 1

Synthesis of Representative Compounds of Structure (1a-1)

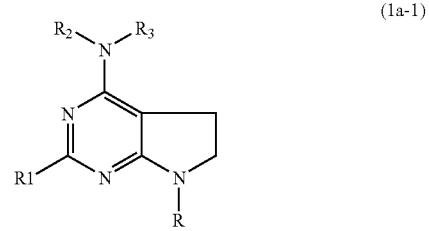

Synthesis of Representative Compounds of Structure (1-1)

[7-(2,4-Dichlorophenyl)-2-methyl-6,7-dihydro-5H-pyrrolo[2,3-d]pyrimidin-4-yl]-(1-ethyl-propyl)amine (1-1-1)

A mixture of intermediate 8 (15 mg) and 1-ethylaminopropane (0.3 mL) was heated at 140° C. (screw cap vial) for 18 hr. It was then cooled down to r.t. and the amine was evaporated. The residue was partitionned between CH₂Cl₂/2.5 M NaOH and the phases were separated. The aqueous layer was extracted with CH₂Cl₂ (2×) and the combined organic extracts were dried over anh. Na₂SO₄. The solids were filtered and the solvent evaporated. The residue was purified by flash chromatography (silic a gel, 15% EtOAc/toluene) to give the title compound (9 mg) as a yellow oil.

The compounds 1-1-4, 1-1-5, 1-1-7, 1-1-8, 1-1-9, 1-1-10, 1-1-11 and 1-1-12, whose analytical data are reported in the following Table 1, were prepared analogously starting from the appropriate amine.

[7-(2-Bromo-4-isopropylphenyl)-2-methyl-6,7-dihydro-5H-pyrrolo[2,3-d]pyrimidin-4-yl]-(1-ethylpropyl)amine (1-1-2)

A mixture of intermediate 13 (21 mg) and 1 ethylaminopropane (300 µl) was heated at 160° C. (screw cap vial) for 48 hr. The reaction mixture was cooled down to r.t. and diluted with water and CH₂Cl₂. The phases were separated and the organic layer was dried and concentrated. The crude oil was purified by flash chromatography (silica gel, cHex/EtOAc 95:5) to give the title compound as a white solid (8 mg).

[7-(2,4-Bis-trifluoromethylphenyl)-2-methyl-6,7-dihydro-5H-pyrrolo[2,3-d]pyrimidin-4-yl]-(1-propylbutyl)amine (1-1-3)

A mixture of intermediate 18 (20 mgl) and 4-heptylamine (150 µL) was heated at 130° C. (screw cap vial) for 8 hr. The reaction mixture was directly purified by flash chromatography (silica gel, cHex/EtOAc 8:2) to give the title compound as a yellow waxy solid (10 mg) All the analytical data are set forth in the following Table 1.

TABLE 1

| Cpd. No. | R | $R_1$ | $R_2$— | $R_3$— | Analytical Data |
|---|---|---|---|---|---|
| 1-1-1 | 2,4-dichlorophenyl | CH$_3$ | (2-ethylbutyl) | H | NMR ($^1$H, CDCl$_3$): δ 7.43(d, 1H), 7.38 (d, 1H), 7.25(dd, 1H), 4.02(s, 1H), 3.93(m, 1H), 3.93(t, 2H), 2.97(t, 2H), 2.33(s, 3H), 1.65(m, 2H), 1.5(m, 2H), 0.94(t, 6H). IR(CDCl$_3$, cm$^{-1}$): 3429. MS (m/z): 365 [MH]$^+$. |
| 1-1-2 | 2-bromo-4-isopropylphenyl | CH$_3$ | (2-ethylbutyl) | H | NMR ($^1$H, CDCl$_3$): δ. 7.43(d, 1H), 7.24 (d, 1H), 7.15(dd, 1H), 4.00(bs, 1H), 3.90(m, 1H), 3.89(t, 2H), 2.94(t, 2H), 2.84(m, 1H), 2.29(s, 3H), 1.65-1.4(m, 4H), 1.21(d, 6H), 0.91(t, 6H). MS (m/z): 417[MH]$^+$, 1Br. |
| 1-1-3 | 2,4-trifluoromethylphenyl | CH$_3$ | (2-propylpentyl) | H | NMR ($^1$H, CDCl$_3$): δ 7.97(bd, 1H), 7.82(bdd, 1H), 7.58(d, 1H), 4.13(bs, 1H), 4.00(bs, 1H), 3.89(t, 2H), 2.98 (m, 2H), 2.32(s, 3H), 1.6-1.3(m, 8H), 0.95(t, 6H). MS (m/z): 461 [MH]$^+$. |
| 1-1-4 | 2,4-dichlorophenyl | CH$_3$ | (4-methoxy-2-methylbutyl) | H | NMR ($^1$H, CDCl$_3$): δ 7.43(d, 1H), 7.37 (d, 1H), 7.25(dd, 1H), 4.43-4.32(m, 2H), 3.94(t, 2H), 3.44(d, 2H), 3.39(s, 3H), 2.94(t, 2H), 2.35(s, 3H), 1.26(d, 3H). MS (m/z): 367 [MH]$^+$ (2Cl). |
| 1-1-5 | 2,4-dichlorophenyl | CH$_3$ | (benzyl-methoxymethyl) | H | NMR ($^1$H, CDCl$_3$): δ 7.44(d, 1H), 7.37 (d, 1H), 7.35-7.20(m, 6H), 4.53(bm, 1H), 4.45(bm, 1H), 3.94(t, 2H), 3.40 (m, 5H), 3.01(dd, 1H), 2.91(m, 3H), 2.39(s, 3H). MS (m/z): 443 [MH]$^+$ (2Cl). |
| 1-1-6 | 2,4-dichlorophenyl | CH$_3$ | (trifluoromethyl-imino) | H | NMR ($^1$H, CDCl$_3$): δ (DMSO) 9.60-8.40(broad, 2H), 7.74(s, 1H), 7.50(m, 2H), 3.92(t, 2H), 3.04(t, 2H), 2.28(s, 3H). MS (m/z): 390 [MH]$^+$. |
| 1-1-7 | 2,4-dichlorophenyl | CH$_3$ | (norbornyl) | H | NMR ($^1$H, CDCl$_3$): δ 7.40(bd, 1H), 7.33(d, 1H), 7.22(dd, 1H), 4.23(bd, 1H), 3.89(t, 2H), 3.75(m, 1H), 3.02(t, 2H), 2.30(s, 3H), 2.28(d, 1H), 2.23(d, 1H), 1.80(m, 1H), 1.20(m, 1H), 1.60-0.80(m, 6H). MS (m/z): 389 [MH]$^+$ (2Cl). |
| 1-1-8 | 2,4-dichlorophenyl | CH$_3$ | (cyclopropylmethyl) | H | NMR ($^1$H, CDCl$_3$): δ 7.43(d, 1H), 7.36 (d, 1H), 7.25(dd, 1H), 4.38(bs, 1H), 3.94(t, 2H), 3.34(t, 2H), 3.01(t, 2H), 2.36(s, 3H), 1.07(m, 1H), 0.56(q, 2H), 0.27(q, 2H). MS (m/z): 349 [MH]$^+$ (2Cl). |
| 1-1-9 | 2,4-dichlorophenyl | CH$_3$ | (2-methylcyclohexyl) | H | NMR ($^1$H, CDCl$_3$): δ 7.43(d, 1H), 7.38 (d, 1H), 7.24(dd, 1H), 3.92(t, 2H), 4.1-3.6(m, 1H), 2.99(m, 2H), 2.34(s, 3H), 2.1-1.95(m, 1H), 1.85-1.1(m, 10H), 1.00-0.94(2d, 3H). MS (m/z): 391 [MH]$^+$ (2Cl). |
| 1-1-10 | 2,4-dichlorophenyl | CH$_3$ | (1-cyclohexylethyl) | H | NMR ($^1$H, CDCl$_3$): δ 7.44(d, 1H), 7.39 (d, 1H), 7.26(dd, 1H), 4.10(m, 1H), 4.00(m, 1H), 3.94(t, 2H), 2.97(t, 2H), 2.34(s, 3H), 1.80-1.00(m, 11H), 1.17 (d, 3H). MS (m/z): 405 [MH]$^+$ (2Cl). |

TABLE 1-continued

| Cpd. No. | R | $R_1$ | $R_2$— | $R_3$— | Analytical Data |
|---|---|---|---|---|---|
| 1-1-11 | 2,4-dichlorophenyl | $CH_3$ | cyclobutyl-CH< | H | NMR ($^1$H, CDCl$_3$): δ 7.44(d, 1H), 7.37 (d, 1H), 7.25(dd, 1H), 4.49(m, 2H), 3.94(t, 2H), 3.01(t, 2H), 2.35(s, 3H), 2.40(m, 2H), 1.91(m, 2H), 1.75(m, 2H). MS (m/z): 349 [MH]$^+$ (2Cl). |
| 1-1-12 | 2,4-dichlorophenyl | $CH_3$ | cyclopentyl-CH< | H | NMR ($^1$H, CDCl$_3$): δ 7.44(d, 1H), 7.38 (d, 1H), 7.26(dd, 1H), 4.34(m, 2H), 3.94(t, 2H), 3.03(t, 2H), 2.35(s, 3H), 2.05(m, 2H), 1.8-1.4(m, 6H). MS (m/z): 363 [MH]$^+$ (2Cl). |

Synthesis of Representative Compounds of Structure (1-2)

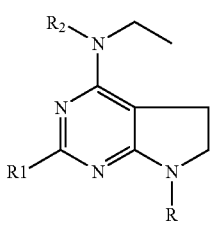

(1-2)

Butyl-[7-(2,4-dichlorophenyl)-2-methyl-6,7-dihydro-5H-pyrrolo[2,3-d]pyrimidin-4-yl]ethyl-amine (1-2-1)

A mixture of intermediate 8 (11.8 mg) and n-butyl-ethylamine (300 μl) was heated in a sealed vial at 160° C. for 18 hr. The crude oil was directly purified by flash chromatography (silica gel, cHex/EtOAc 19:1) to give the title compound (10 mg) as a light yellow oil.

The compounds 1-2-6, 1-3-1, 1-3-2 and 1-3-3, whose analytical data are reported in the following Table 1-2, were prepared analogously starting from the appropriate amine.

[7-(2-Bromo-4-isopropylphenyl)-2-methyl-6,7-dihydro-5H-pyrrolo[2,3-d]pyrimidin-4-yl]-butylethylamine (1-2-2)

A mixture of intermediate 13 (20 mg) and n-butyl-ethylamine (300 μl) was heated in a sealed vial at 160° C. for 18 hr. The reaction mixture was cooled down to r.t. and diluted with water and CH$_2$Cl$_2$. The phases were separated and the organic layer was dried and concentrated. The crude oil was purified by flash chromatography (silica gel, cHex/EtOAc 95:5) to give the title compound as a yellow oil.

Butyl-[7-(2-chloro-4-trifluoromethylphenyl)-2-methyl-6,7-dihydro-5H-pyrrolo[2,3-d]pyrimidin-4-yl]ethylamine (1-2-3)

A mixture of intermediate 23 (21 mg) and of n-butyl-ethylamine (300 μl) were heated in a sealed vial at 160° C. for 18 hr. The reaction mixture was cooled down to r.t. and diluted with water and CH$_2$Cl$_2$. The phases were separated and the organic layer was dried and concentrated. The crude oil was purified by flash chromatography (silica gel, cHex/EtOAc 95:5) to give the title compound as a white solid (20 mg).

[7-(2,4-Bis-trifluoromethylphenyl)-2-methyl-6,7-dihydro-5H-pyrrolo[2,3-d]pyrimidin-4-yl]-butylethylamine (1-2-4)

A mixture of intermediate 18 (21 mg) and n-butyl-ethylamine (300 μl) was heated in a sealed vial at 160° C. for 18 hr The reaction mixture was cooled down to r.t. and diluted with water and CH$_2$Cl$_2$. The phases were separated and the organic layer was dried and concentrated. The crude oil was purified by flash chromatography (silica gel, cHex/EtOAc 95:5) to give the title compound as a yellow oil (14 mg).

Butyl-[7-(2,4-dichlorophenyl)-2-trifluoromethyl-6,7-dihydro-5H-pyrrolo[2,3-d]pyrimidin-4-yl]ethylamine (1-2-5)

The sequence for the preparation of example 1-2-5 is similar to the preparation of example 1-2-1 (intermediate 1 to intermediate 8) except that 2,2,2-trifluoroacetamidine hydrochloride was used instead of acetamidine hydrochloride in the first step (intermediate 1).

All the analytical data are set forth in the following Table 1-2.

TABLE 1-2

| Cpd. No. | R | $R_1$ | $R_2$— | $R_3$— | Analytical Data |
|---|---|---|---|---|---|
| 1-2-1 | 2,4-dichlorophenyl | $CH_3$ | n-butyl | Et | NMR ($^1$H, CDCl$_3$): δ 7.43(d, 1H), 7.37 (d, 1H), 7.25(dd, 1H), 3.84(t, 2H), 3.56(q, 2H), 3.48(dd, 2H), 3.25(t, 2H), 2.32(s, 3H), 1.59(m, 2H), 1.36 (m, 2H), 1.19(t, 3H), 0.97(t, 3H). MS (m/z): 379 [MH]$^+$, 2Cl |

TABLE 1-2-continued

| Cpd. No. | R | R₁ | R₂— | R₃— | Analytical Data |
|---|---|---|---|---|---|
| 1-2-2 | 2-bromo-4-iso-propylphenyl | CH₃ | (n-butyl) | Et | NMR (¹H, CDCl₃): δ 7.47(d, 1H), 7.28 (d, 1H), 7.19(dd, 1H), 3.83(t, 2H), 3.55(q, 2H), 3.48(m, 2H), 3.24(t, 2H), 2.89(m, 1H), 2.31(s, 3H), 1.58 (m, 2H), 1.36(m, 2H), 1.25(d, 6H), 1.18(t, 3H), 0.97(t, 3H). MS (m/z): 431 [MH]⁺, 1Cl, 1Br. |
| 1-2-3 | 2-chloro-4-trifluoromethyl-phenyl | CH₃ | (n-butyl) | Et | NMR (¹H, CDCl₃): δ 7.68(d, 1H), 7.61 (d, 1H), 7.51(dd, 1H), 3.92(t, 2H), 3.57(q, 2H), 3.49(t, 2H), 3.27(t, 2H), 2.33(s, 3H), 1.61(m, 2H), 1.37(m, 2H), 1.19(t, 3H), 0.98(t, 3H). MS (m/z): 413 [MH]⁺. |
| 1-2-4 | 2,4-bis-trifluoro-methylphenyl | CH₃ | (n-butyl) | Et | NMR (¹H, CDCl₃): δ 7.95(bs, 1H), 7.81(dd, 1H), 7.53(d, 1H), 3.78(t, 2H), 3.56(q, 2H), 3.48(m, 2H), 3.25 (t, 2H), 2.29(s, 3H), 1.60(m, 2H), 1.36 (m, 2H), 1.19(t, 3H), 0.97(t, 3H). MS (m/z): 447 [MH]⁺. |
| 1-2-5 | 2,4-dichloro-phenyl | CF₃ | (n-butyl) | Et | NMR (¹H, CDCl₃): δ 7.45(d, 1H), 7.35 (d, 1H), 7.28(dd, 1H), 3.94(t, 2H), 3.57(q, 2H), 3.50(t, 2H), 3.33(t, 2H), 1.62(m, 2H), 1.37(m, 2H), 1.22(t, 3H), 0.98(t, 3H). MS (m/z): 433 [MH]⁺ (2Cl; 100%). |
| 1-2-6 | 2,4-dichloro-phenyl | CH₃ | (pyridin-4-ylmethyl) | Et | MS (m/z): 414 [MH]⁺ (2Cl) |

Synthesis of Representative Compounds of Structure (1-3)

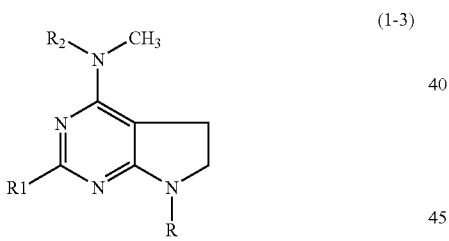

(1-3)

Representative compounds of this invention were prepared by the procedure set forth above for compounds of general formula (1-2).

All the analytical data are set forth in the following Table 1-3.

TABLE 1-3

| Cpd. No. | R | R₁ | R₂— | R₃— | Analytical Data |
|---|---|---|---|---|---|
| 1-3-1 | 2,4-dichloro-phenyl | CH₃ | (2-methylallyl) | Me | NMR (¹H,): δ. 7.43(d, 1H), 7.37(d, 1H), 7.25(dd, 1H), 4.91(s, 1H), 4.85 (s, 1H), 4.07(s, 2H), 3.81(t, 2H), 3.55(q, 2H), 3.24(t, 2H), 2.33(s, 3 H); 1.74(s, 3H), 1.17(t, 3H). MS (m/z): 377 [MNH₄]⁺. 2 Cl |
| 1-3-2 | 2,4-dichloro-phenyl | CH₃ | (dimethyl acetal) | Me | MS (m/z): 397 [MH]⁺ (2Cl) |

TABLE 1-3-continued

| Cpd. No. | R | $R_1$ | $R_2$— | $R_3$— | Analytical Data |
|---|---|---|---|---|---|
| 1-3-3 | 2,4-dichloro-phenyl | $CH_3$ | 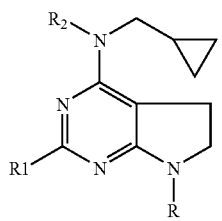 | | Me MS (m/z): 351 [MH]$^+$ (2Cl) |

Synthesis of Representative Compounds of Structure (1-4)

(1-4)

[7-(2-Chloro-4-trifluoromethyl-phenyl)-2-methyl-6,7-dihydro-5H-pyrrolo[2,3-d]pyrimidin-4-yl]cyclopropylmethyl-propylamine (1-4-1)

A mixture of intermediate 23 (20.6 mg) and of N-propyl cyclopropane methyl amine (300 µl) were heated in a sealed vial at 160° C. for 18 hr. The reaction mixture was cooled down to r.t. and diluted with water and $CH_2Cl_2$. The phases were separated and the organic layer was dried and concentrated. The crude oil was purified by flash chromatography (silica gel, cHex/EtOAc 95:5) to give the title compound as a white solid (21 mg)

[7-(2,4-Bis-trifluoromethylphenyl)-2-methyl-6,7-dihydro-5H-pyrrolo[2,3-d]pyrimidin-4-yl]-cyclopropylmethylpropylamine (1-4-2)

A mixture of intermediate 18 (20.4 mg) and of N-propyl cyclopropane methyl amine (300 µl) was heated in a sealed vial at 160° C. for 18 hr. The reaction mixture was cooled down to r.t. and diluted with water and $CH_2Cl_2$. The phases were separated and the organic layer was dried and concentrated. The crude oil was purified by flash chromatography (silica gel, cHex/EtOAc 95:5) to give the title compound as a yellow oil (11 mg).

[7-(2-Bromo-4-isopropylphenyl)-2-methyl-6,7-dihydro-5H-pyrrolo[2,3-d]pyrimidin-4-yl]-cyclopropylmethylpropylamine (1-4-3)

A mixture of intermediate 13 (22 mg) and N-propyl cyclopropane-methylamine (300 µl) was heated in a sealed vial at 160° C. for 18 hr. The reaction mixture was cooled down to r.t. and diluted with water and $CH_2Cl_2$. The phases were separated and the organic layer was dried and concentrated. The crude oil was purified by flash chromatography (silica gel, cHex/EtOAc 95:5) to give the title compound as a yellow oil (17 mg).

Cyclopropylmethyl-[7-(2,4-dichlorophenyl)-2-methyl-6,7-dihydro-5H-pyrrolo[2,3-d]pyrimidin-4-yl]propylamine (1-4-4)

A mixture of intermediate 8 (12 mg) and N-propyl cyclopropane methyl amine (300 µl) was heated in a sealed vial at 160° C. for 18 hours. The crude oil was directly purified by flash chromatography (silica gel, cHex/EtOAc 8:2) to give the title compound as a light yellow oil (11 mg).

All the analytical data are set forth in the following Table 1-4.

TABLE 1-4

| Cpd. No. | R | $R_1$ | $R_2$— | $R_3$— | Analytical Data |
|---|---|---|---|---|---|
| 1-4-1 | 2-chloro-4-trifluoromethyl-phenyl | $CH_3$ | | | NMR ($^1$H, CDCl$_3$): δ 7.68(d, 1H), 7.61 (d, 1H), 7.52(dd, 1H), 3.93(t, 2H), 3.52(t, 2H), 3.47(d, 2H), 3.30(t, 2H), 2.33(s, 3H), 1.66(m, 2H), 1.07(m, 1H), 0.93(t, 3H), 0.55-0.29(m, 4H). MS (m/z): 425 [MH]$^+$. |
| 1-4-2 | 2,4-bistrifluoro-methylphenyl | $CH_3$ | | | NMR ($^1$H, CDCl$_3$): δ 7.95(d, 1H), 7.81 (dd, 1H), 7.54(d, 1H), 3.78(t, 2H), 3.50(m, 2H), 3.46(d, 2H), 3.29(t, 2H), 2.28(s, 3H), 1.63(m, 2H), 1.05 (m, 1H), 0.93(t, 3H), 0.53(m, 2H), 0.29(q, 2H). MS (m/z): 459 [MH]$^+$. |

TABLE 1-4-continued

| Cpd. No. | R | $R_1$ | $R_2$— | $R_3$— | Analytical Data |
|---|---|---|---|---|---|
| 1-4-3 | 2-bromo-4-isopropylphenyl | $CH_3$ | ~~~~ | ▷ | NMR ($^1$H, CDCl$_3$): δ 7.46(d, 1H), 7.28 (d, 1H), 7.18(dd, 1H), 3.84(t, 2H), 3.51(m, 2H), 3.46(m, 2H), 3.27(t, 2H), 2.89(m, 1H), 2.31(s, 3H), 1.66 (m, 2H), 1.25(d, 6H), 1.09(m, 1H), 0.93(t, 3H), 0.53(m, 2H), 0.28(q, 2H). MS (m/z): 431 [MH]$^+$, 1Cl, 1Br. |
| 1-4-4 | 2,4-dichlorophenyl | $CH_3$ | ~~~~ | ▷ | NMR($^1$H, CDCl$_3$): δ 7.43(d, 1H), 7.37(d, 1H), 7.25(dd, 1H), 3.84(t, 2H), 3.50(dd, 2H), 3.46(d, 2H), 3.28 (t, 2H), 2.31(s, 3H), 1.65(m, 2H), 1.07 (m, 1H), 0.93(t, 3H), 0.53(m, 2H), 0.29(m, 2H). MS (m/z): 391 [MH]$^+$ (2Cl) |
| 1-4-5 | 3,4-dimethoxyphenyl | $CH_3$ | ~~~~ | ▷ | NMR ($^1$H, CDCl$_3$): δ 6.80(d, 1H), 6.70 (s, 1H), 6.60(d, 1H), 4.10, (dd, 1H), 3.85(s, 6H), 3.45(m, 2H), 3.15(m, 1H), 3.05(m, 1H), 2.2.50(m, 1H), 2.45 (s, 3H), 1.95(m, 1H), 1.65(m, 2H), 1.05(m, 1H), 0.80-0.95(m, 5H), 0.55 (m, 2H), 0.30(m, 2H). MS (m/z): 382 [MH]$^+$. |

Synthesis of Representative Compounds of Structure (1-5)

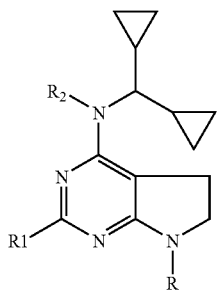

(1-5)

Representative compounds of this invention were prepared by the procedure set forth above for compounds of general formula (1-2).

All the analytical data are set forth in the following Table 1-5.

Synthesis of Representative Compounds of Structure (1-6)

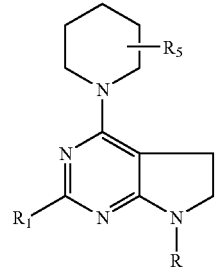

(1-6)

7-(2,4-Dichlorophenyl)-4-(2-ethylpiperidin-1-yl)-2-methyl-6,7-dihydro-5H-pyrrolo[2,3-d]pyrimidine (1-6-3)

A mixture of intermediate 8 (10 mg) and 2-ethylpiperidine (120 μL) was heated in a sealed vial at 160° C. for 7 hr. The crude oil was directly purified by flash chromatography (silica gel, cHex/EtOAc 4:1) to give the title compound (8.7 mg) as a yellow oil.

The compounds 1-6-1, 1-6-2, 1-6-4 and 1-6-5, whose analytical data are reported in the following Table 1-6, were prepared analogously starting from the appropriate amine.

TABLE 1-5

| Cpd. No. | R | $R_1$ | $R_2$— | $R_3$— | Analytical Data |
|---|---|---|---|---|---|
| 1-5-1 | 2,4-dichlorophenyl | $CH_3$ | ~~~~ | ▷▷ | NMR ($^1$H, CDCl$_3$): δ 7.41(d, 1H), 7.37 (d, 1H), 7.23(dd, 1H), 3.80(t, 2H), 3.63(m, 1H), 3.45(t, 2H), 3.15(t, 2H), 2.24(s, 3H), 1.75(m, 2H), 1.06(m, 2H), 0.93(t, 3M), 0.70-0.30(m, 8H). MS (m/z): 431 [MH]$^+$ (2Cl) |

All the analytical data are set forth in the following Table 1-6.

TABLE 1-6

| Cpd. No. | R | $R_1$ | $R_2$—$R_3$— | Analytical Data |
|---|---|---|---|---|
| 1-6-1 | 2,4-dichlorophenyl | CH₃ | (3,5-dimethylpiperidinyl) | NMR (¹H, CDCl₃): δ 7.43(d, 1H), 7.35(d, 1H), 7.24(dd, 1H), 4.41(m, 2H), 3.84(t, 2H), 3.24(t, 2H), 2.32(s, 3H), 2.30(m, 2H), 1.85(m, 1H), 1.66 (m, 2H), 0.91(d, 6H), 0.80(m, 1H). MS (m/z): 391 [MH]⁺. |
| 1-6-2 | 2,4-dichlorophenyl | CH₃ | (2-methylpiperidinyl) | NMR (¹H,): δ 7.42(d, 1H), 7.35(d, 1H), 7.23(dd, 1H), 4.71(m, 1H), 4.33 (bd, 1H), 3.83(t, 2H), 3.24(m, 2H), 3.02(dt, 1H), 2.32(s, 3H), 1.78-1.49 (m, 6H), 1.21(d, 3H). MS (m/z): 377 [MH]⁺. |
| 1-6-3 | 2,4-dichlorophenyl | CH₃ | (2-ethylpiperidinyl) | NMR (¹H, CDCl₃): δ 7.42(d, 1H), 7.36 (d, 1H), 7.24(dd, 1H), 4.44(m, 1H), 4.38(m, 1H), 3.83(m, 2H), 3.22(t, 2H), 2.97(m, 1H), 2.31(s, 3H), 1.73 (m, 2H), 1.80-1.10(m, 6H), 0.88(t, 3H). MS (m/z): 391 [MH]⁺. |
| 1-6-4 | 2,4-dichlorophenyl | CH₃ | (2,6-dimethylmorpholinyl) | NMR (¹H, CDCl₃): δ 7.44(d, 1H), 7.35(d, 1H), 7.25(dd, 1H), 4.25(d, 2H), 3.87(t, 2H), 3.69(m, 2H), 3.25 (t, 2H), 2.64(d, 2H), 2.33(s, 3H), 1.24 (d, 6H). MS (m/z): 393 [MH]⁺. |
| 1-6-5 | 2,4-dichlorophenyl | CH₃ | (thiomorpholinyl) | MS (m/z): 381 [MH]⁺ (2Cl) |

Synthesis of Representative Compounds of Structure (1-7)

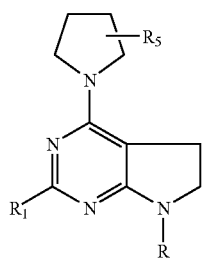

(1-7)

7-(2,4-Dichlorophenyl)-4-[(2R, 5R)-2,5-dimethylpyrrolidin-1-yl]-2-methyl-6,7-dihydro-5H-pyrrolo[2,3-d]pyrimidine (1-7-3)

A mixture of intermediate 8 (11.8 mgl) and (2R,5R)-(−)-trans-2,5-dimethyl-pyrrolidine (150 μl) was heated in a sealed vial at 160° C. for 18 hr. The crude oil was directly purified by flash chromatography (silica gel, cHex/EtOAc 19:1) to give the title compound (7 mg) as a white solid.

The compounds 1-7-1, 1-7-2, 1-7-4 and 1-7-5, whose analytical data are reported in the following Table 1-7, were prepared analogously starting from the appropriate amine.

All the analytical data are set forth in the following Table 1-7.

TABLE 1-7

| Cpd. No. | R | $R_1$ | $R_2$—$R_3$— | Analytical Data |
|---|---|---|---|---|
| 1-7-1 | 2,4-dichlorophenyl | CH₃ | (pyrrolidinyl) | NMR (¹H, CDCl₃): δ 7.42(d, 1H), 7.36(d, 1H), 7.24(dd, 1H), 3.83(t, 2H), 3.66(t, 4H), 3.35(t, 2H), 2.33(s, 3H), 1.92(m, 4H). MS (m/z): 349 [MH]⁺ (2Cl) |

TABLE 1-7-continued

| Cpd. No. | R | $R_1$ | $R_2$—$R_3$— | Analytical Data |
|---|---|---|---|---|
| 1-7-2 | 2,4-dichloro-phenyl | $CH_3$ | (2-methylpyrrolidinyl) | NMR ($^1$H, CDCl$_3$): δ 7.42(d, 1H), (d, 1H), 7.24(dd, 1H), 4.39(m, 1H), 3.88(m, 2H), 3.76(m, 1H), 3.60 (m, 1H), 3.30(m, 2H), 2.32(s, 3H), 2.06(m, 2H), 1.90(m, 1H), 1.65(m, 1H), 1.21(d, 3H). MS (m/z): 363 [MH]$^+$ (2Cl). |
| 1-7-3 | 2,4-dichloro-phenyl | $CH_3$ | (2,5-dimethylpyrrolidinyl) | NMR ($^1$H, CDCl$_3$): δ 7.41(d, 1H), 7.39 (d, 1H), 7.24(dd, 1H), 4.4(m, 2H), 3.9-3.8(m, 2H), 3.16(m, 2H), 2.32(s, 3H), 2.18(m, 2H), 1.6(m, 2H), 1.13 (d, 6H). MS (m/z): 377 [MH]$^+$, 2Cl |
| 1-7-4 | 2,4-dichloro-phenyl | $CH_3$ | (2,5-bis(methoxymethyl)pyrrolidinyl) | MS (m/z): 437 [MH]$^+$ (2Cl). |
| 1-7-5 | 2,4-dichloro-phenyl | $CH_3$ | (2-(carbamoylmethyl)pyrrolidinyl) | NMR ($^1$H, CDCl$_3$): δ 7.44(d, 1H), 7.34(d, 1H), 7.26(dd, 1H), 7.12(bs, 1H), 5.29(bs, 1H), 4.62(bm, 1H), 3.86(t, 2H), 3.81(m, 1H), 3.60(m, 1H), 3.36(m, 2H), 2.81(dd, 1H), 2.32 (s, 3H), 2.24(dd, 1H), 2.01(m, 4H). MS (m/z): 406 [MH]$^+$ (2Cl). |

Synthesis of Representative Compounds of Structure (1-8)

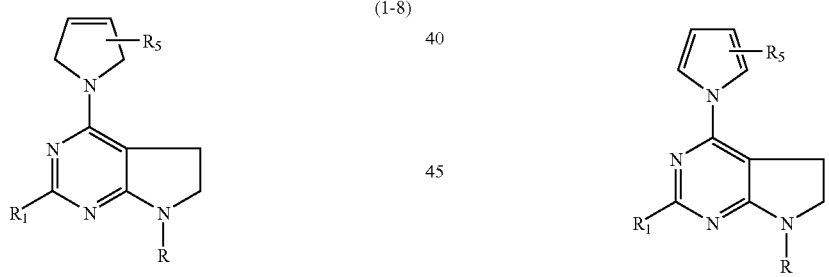

Representative compounds of this invention were prepared by the procedure set forth above for compounds of general formula (1-7).

All the analytical data are set forth in the following Table 1-8.

Synthesis of Representative Compounds of Structure (1-9)

Representative compounds of this invention were prepared by the procedure set forth in the examples below (example 1-10-1) using the appropriate pyrrole or indole derivative.

TABLE 1-8

| Cpd. No. | R | $R_1$ | $R_2$—$R_3$— | Analytical Data |
|---|---|---|---|---|
| 1-8-1 | 2,4-dichloro-phenyl | $CH_3$ | (2,5-dimethyl-2,5-dihydropyrrolyl) | NMR ($^1$H, CDCl$_3$): δ 7.43(d, 1H), 7.38(d, 1H), 7.25(dd, 1H), 5.80(s, 2H), 4.94(q, 2H), 3.84(t, 2H), 3.32(t, 2H), 2.33(s, 3H), 1.42(d, 6H). MS (m/z): 375 [MH]$^+$ (2Cl). |

All the analytical data are set forth in the following Table 1-9.

TABLE 1-9

| Cpd. No. | R | $R_1$ | $R_2$—$R_3$— | Analytical Data |
|---|---|---|---|---|
| 1-9-1 | 2,4-dichloro-phenyl | CH$_3$ | 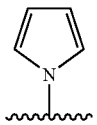 | NMR ($^1$H, CDCl$_3$): δ 7.54(t, 2H), 7.50 (d, 1H), 7.38(d, 1H), 7.32(d, 1H), 6.37(t, 2H), 4.04(t, 2H), 3.44(t, 2H), 2.46(s, 3H). MS (m/z): 345 [MH]$^+$ (2Cl). |
| 1-9-2 | 2,4-dichloro-phenyl | CH$_3$ | 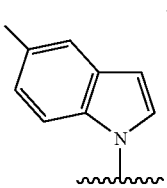 | NMR ($^1$H, CDCl$_3$): δ 8.24(d, 1H), 7.61(d, 1H), 7.53(d, 1H), 7.52(d, 1H), 7.41(d, 1H), 7.35(dd, 1H), 7.26 (dd, 1H), 6.67(d, 1H), 4.06(t, 2H), 3.37(t, 2H), 2.55(s, 3H). MS (m/z): 429 [MH]$^+$ (3Cl). |
| 1-9-3 | 2,4-dichloro-phenyl | CH$_3$ | 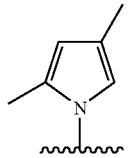 | NMR ($^1$H, CDCl$_3$): δ 7.49(d, 1H), 7.39(d, 1H), 7.32(dd, 1H), 6.62(s, 1H), 5.87(s, 1H), 3.99(t, 2H), 3.27(t, 2H), 2.44(s, 3H), 2.40(s, 3H), 2.07(s, 3H). MS (m/z): 373 [MH]$^+$ (2Cl). |

Synthesis of Representative Compounds of Structure (1-10)

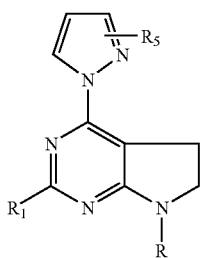

(1-10)

7-(2,4-dichlorophenyl)-2-methyl-4-(3-thiazol-2-yl-pyrazol-1-yl)-6,7-dihydro-5H-pyrrolo[2,3-d]pyrimidine (1-10-1)

2-(1H-pyrazol-3-yl)-thiazole (22 mg) was added to a suspension of NaH 80%/oil (4 mg) in anh. DMF (300 μL). After stirring for 30 min, intermediate 8 (15 mg) was added at r.t. and the resulting mixture was heated at 110° C. for 3 hr. The reaction was then concentrated in vacuo and the residue was diluted with H$_2$O and extracted with CH$_2$Cl$_2$ (3×5 mL). The combined organic extracts were dried over anh. Na$_2$SO$_4$, the solids were filtered and the solvent evaporated. The title compound was obtained after chromatographic purification (silica gel, cHex/EtOAc 4:1) as a white solid (16.5 mg).

The compounds 1-1-6, 1-9-1, 1-9-2, 1-9-3, 1-10-4, 1-10-5, 1-10-12, 1-10-13, 1-10-20, 1-10-21, 1-10-24, 1-10-25, 1-10-26 and 3-2-1, whose analytical data are reported in the following Table 1-10 or in the corresponding tables, were prepared analogously starting from the appropriate amine, pyrrole or pyrazole derivative.

7-(2,4-bis-trifluoromethyl-phenyl)-2-methyl-4-(3-Thiazol-2-yl-pyrazol-1-yl)-6,7-dihydro-5H-pyrrolo[2,3-d]pyrimidine (1-10-2)

To a suspension of NaH 80%/oil (3.54 mmol, 3.0 eq) in dry DMF (13 mL) at r.t., under N$_2$, was added 2-(1H-pyrazol-3-yl)-thiazole (538 mg, 3.54 mmol, 3 eq). The reaction mixture was stirred at r.t. for 30 min. Intermediate 18 (450 mg, 1.18 mmol) was added and the reaction mixture was heated at 100° C. (screw cap vial) for 4 h. It was cooled down and poured into EtOAc. The organic layer was washed with sat. aq. NaCl (3×) and dried over anh. Na$_2$SO$_4$. The solids were filtered and the solvent evaporated. The crude product was purified by flash chromatography (silica gel, Toluene/EtOAc 9:1) to give the title compound as white solid (535 mg, 99%).

The compounds 1-10-31, 1-10-32, 1-10-33, 1-10-37 and 1-10-40, whose analytical data are reported in the following Table 1-10, were prepared analogously using respectively 4-(1H-pyrazol-3-yl)-morpholine (*J. Org. Chem.*, 1984, 269-276), 3-(1H-pyrazol-3-yl)-pyridine (*Bioorg. Med. Chem. Lett.*, 2000, 1211-1214), 2-(1H-pyrazol-3-yl)-pyrazine (*Tet. Lett.*, 1999, 4779-4782), 3-(1H-imidazol-2-yl)-1H-pyrazole (*J. Het. Chem.*, 1989, 893) and 5-(1H-pyrazol-3-yl)-oxazole (*Tet. Lett.*, 1972, 2369-2372) instead of 2-(1H-pyrazol-3-yl)-thiazole.

The compounds 1-10-35 and 1-10-38, whose analytical data are reported in the following Table 1-10, were prepared analogously using 1H-pyrazole-3-carboxylic acid ethyl ester instead of 2-(1H-pyrazol-3-yl)-thiazole. The ester group was then transformed into the corresponding N-methyltriazole and oxadiazole following procedures known in the literature (*J. Het. Chem.*, 1986, 1391).

Compound 1-10-36, whose analytical data are reported in the following Table 1-10, was prepare by methylation of compound 1-10-37 using NaH as a base and methyl iodide as a methylating agent.

The compounds 1-10-29, 1-10-34 and 1-10-39, whose analytical data are reported in the following Table 1-10, were prepared analogously using respectively 2-amino-3,5-dichloropyridine, 2-amino-3-chloro-5-trifluoromethylpyridine and 3-amino-2-trifluoromethylpyridine instead of 2,4-bis-trifluoromethyl-aniline in the preparation of intermediate 54.

Compound 1-10-30, whose analytical data are reported in the following Table 1-10, was prepared analogously using 2,6-dimethoxy-3-aminopyridine in THF with EtONa as a base instead of 2,4-bis-trifluoromethyl-aniline in DMF with NaH as a base in the preparation of intermediate 54.

7-(2,4-Dichlorophenyl)-2-methyl-4-(3-trifluoromethylpyrazol-1-yl)-6,7-dihydro-5H-pyrrolo[2,3-d]pyrimidine (1-10-5)

To a suspension of NaH 80%/oil (6 mg) in anh. DMF, at r.t., under $N_2$, was added 3-(trifluoromethyl)pyrazole (20 mg). The reaction mixture was stirred at r.t. until gas evolution ceased (20 min). Intermediate 8 (15 mg) was then added and the reaction mixutre was heated at 100° C. (screw cap vial) for 4 hr. It was then cooled down to r.t. and poured into EtOAc. The organic layer was washed with sat.aq. NaCl (3×5 mL) and dried over anh. $Na_2SO_4$. The solids were filtered and the solvent evaporated. The crude product was purified by flash chromatography (silica gel, cHex/EtOAc 95:5) to give the title compound as a yellow solid (0.011 g).

7-(2-Bromo-4-isopropylphenyl)-2-methyl-4-(3-trifluoromethylpyrazol-1-yl)-6,7-dihydro-5H-pyrrolo[2,3-d]4-pyrimidine (1-10-6)

3-(Trifluoromethyl)pyrazole (22.7 mg) was added to a suspension of NaH (80% in mineral oil, 5 mg) in anh. DMF (0.5 mL) at 0° C. After 10 min, 20 mg of intermediate 13 (20 mg) were added and the solution was heated in a sealed vial at 100° C. for 4 hr. The reaction mixture was poured into water and extracted with EtOAc (3×5 mL). The combined organic extracts were dried over anh. $Na_2SO_4$. The solids were filtered, the solvent was evaporated and the crude oil was purified by flash chromatography (silica gel, cHex/EtOAc 95:5) to give the title compound as a clear oil (12 mg).

7-(2,4-Dichlorophenyl)-4-(5-isopropyl-3-trifluoromethylpyrazol-1-yl)-2-methyl-6,7-dihydro-5H-pyrrolo[2,3-d]pyrimidine and 7-(2,4-Dichlorophenyl)-4-(3-isopropyl-5-trifluoromethyl-pyrazol-1-yl)-2-methyl-6,7-dihydro-5H-pyrrolo[2,3-d]pyrimidine (1-10-7)

To a solution of intermediate 8 (22 mg) in anh. MeOH (0.7 mL), at r.t., under $N_2$, was added hydrazine monohydrate (34 µL). The reaction mixture was heated at 130° C. in a sealed vial for 18 hr. It was then cooled down to r.t. and the the solvent was evaporated to dryness in vacuo. The oil obtained was dissolved into anh. EtOH (0.7 mL) and 1,1,1-trifluoromethyl-5-methylhexanedione (26 mg) was added. The reaction mixture was heated at 110° C. in a sealed vial for 18 hr. The solvent was evaporated and the crude product was purified by flash chromatography (silica gel, cHex/EtOAc 95:5) to give the title compound (14 mg) as a mixutre of regioisomers: 5-isopropyl-3-trifluoromethyl-pyrazole (60%) and 3-isopropyl-5-trifluoromethyl-pyrazole (40%).

4-(4-Bromo-5-methyl-3-trifluoromethylpyrazol-1-yl)-7-(2,4-dichlorophenyl-2-methyl-6,7-dihydro-5H-pyrrolo[2,3-d]pyrimidine (1-10-8)

4-Bromo-5-methyl-3-trifluoromethyl-1H-pyrazole (48 mg) was added to a suspension of NaH 80%/oil (4 mg) in anh. DMF (300 µL). After stirring for 30 min, intermediate 8 (15 mg) was added at r.t. and the resulting mixture was heated at 110° C. for 3 hr. The reaction was then concentrated in vacuo and the residue was diluted with $H_2O$ and extracted $CH_2Cl_2$ (3×5 mL). The combined organic extracts were dried over anh. $Na_2SO_4$, the solids were filtered and the solvent evaporated. The title compound was obtained after chromatographic purification (silica gel, cHex/EtOAc 95:5) as a white solid (12 mg).

7-(2,4-dichlorophenyl)4-(3-ethyl-5-trifluoromethylpyrazol-1-yl)-2-methyl-6,7-dihydro-5-H-pyrrolo[2,3-d]pyrimidine (1-10-9)

A solution of intermediate 8 (21 mg) and hydrazine monohydrate (65 µL) in anh. MeOH (300 µL) was heated at 130° C. for 6 hr. The mixture was then concentrated in vacuo and the residue was dissolved in EtOH (300 µL). 1,1,1-trifluoro-2,4-hexanedione (32 mg) was added and the solution was stirred at 120° C. for 18 hr. The solvent was evaporated and the residue was purified by flash chromatography (silica gel, cHex/EtOAc 96:4). The title compound was obtained as a colorless oil (5 mg).

7-(2,4-Dichlorophenyl)-2-methyl-4-(3-methylpyrazol-1-yl)-6,7-dihydro-5H-pyrrolo[2,3-d]pyrimidine (1-10-10)

To a suspension of NaH 80%/oil (5.5 mg, 3 eq) in anh. DMF (0.3 mL), at r.t., under $N_2$, was added 3-methyl-pyrazole (16 mg, 3 eq) and the reaction mixture was stirred at r.t. for 30 min. Intermediate 8 (20 mg, 0.064 mmol) was added and the reaction mixute was stirred at 100° C. (screw cap vial) for 6 hr. The solvent was evaporated and the risidue taken up in $H_2O$ and extracted with $CH_2Cl_2$ (3×). The combined organic extracts were dried over anh. $Na_2SO_4$, the solids were filtered and the solvent evaporated. The crude product was purified by flash chromatography (silica gel, cHex/EtOAc 9:1) to give the title compound as a white solid (17.5 mg, 76%) along with a small quantity of its 5-methyl-pyrazole isomer (example 1-10-12, 1 mg, 6%)

7-(2,4-Dichlorophenyl)-4-(3,5-dimethylpyrazol-1-yl)-2-methyl-6,7-dihydro-5H-pyrrolo[2,3-d]pyrimidine (1-10-11)

To a suspension of NaH 80%/oil (5 mg, 3 eq) in anh DMF (0.5 mL), at r.t., under $N_2$, was added 3,5-dimethylpyrazole (14 mg, 3 eq) and the reaction mixture was stirred for 20 min at r.t. Intermediate 8 (15 mg, 0.048 mmol) was then added and the reaction mixture was heated at 100° C. (screw cap vial) for 18 hr. It was then cooled down to r.t. and poured into EtOAc/sat.aq. NaCl. The phases were separated and the organic layer was washed with sat.aq. NaCl (2×) and dried over anh. $Na_2SO_4$. The solids were filtered and the solvent evaporated. The residue was purified by flash chromatography (silica gel, cHex/EtOAc 9:1) to give the title compound as a white solid (9 mg).

7-(2,4-Dichlorophenyl)-4-(3-ethoxy-5-methylpyrazol-1-yl)-2-methyl-6,7-dihydro-5H-pyrrolo[2,3-d]pyrimidine (1-10-14)

To a suspension of NaH 80%/oil (5 mg, 3 eq) in anh. DMF (0.5 mL), at r.t., under $N_2$, was added 3-ethoxy-5-methyl-pyrazole (18 mg, 3 eq) and the reaction mixture was stirred at r.t. until gas evolution ceased (20 min). Intermediate 8 (15 mg, 0.048 mol) was then added and the reaction mixture was stirred at 100° C. (screw cap vial) for 4 hr. It was then cooled down to r.t. and partitioned between EtOAc/sat.aq. NaCl. The phases were separated and the organic layer was washed with sat.aq. NaCl (2×). It was dried over anh. $Na_2SO_4$, the solids were filtered and the solvent evaporated. The crude product was purified by flash chromatography (silica gel, cHex/EtOAc 8:2) to give the title compound as a yellow solid (6 mg)

7-(2,4-Dichlorophenyl)-4-(3-dimethoxymethylpyrazol-1-yl)-2-methyl-6,7-dihydro-5H-pyrrolo[2,3-d]pyrimidine (1-10-15)

To a suspension of NaH 80%/oil (4 mg, 3 eq) in anh. DMF (0.3 mL), at r.t., under $N_2$, was added pyrazol-3-carboxaldehyde dimethyl acetal (20.5 mg, 3 eq) and the reaction mixture was stirred at r.t. for 30 min. Intermediate 8 (15 mg, 0.048 mmol) was added and the reaction mixute was stirred at 100° C. (screw cap vial) for 3 hr. The solvent was evaporated and the residue taken up in $H_2O$ and extracted with $CH_2Cl_2$ (3×). The combined organic extracts were dried over anh. $Na_2SO_4$, the solids were filtered and the solvent evaporated. The crude product was purified by flash chromatography (silica gel, cHex/EtOAc 8:2) to give the title compound as a white solid (16 mg, 80%).

7-(2,4-dichlorophenyl)-4-(3-ethyl-5-trifluoromethylpyrazol-1-yl)-2-methyl-6,7-dihydro-5H-pyrrolo[2,3-d]pyrimidine (1-10-16)

A solution of intermediate 8 (21 mg, 0.067 mmol) and hydrazine monohydrate (65 μL, 1.34 mmol) in anh MeOH (300 μL) was heated at 130° C. (screw cap vial) for 6 hr. The mixture was then concentrated in vacuo and 1,1,1-trifluoro-2,4-hexanedione (32 mg, 0.113 mmol) was added to the crude product dissolved in 300 μL of EtOH. The solution was stirred overnight at 120° C. and, after evaporation of the solvent, was purified by flash chromatography (silica gel, cHex/EtOAc 96:4). The title compound was obtained as a clear oil (5 mg)

7-(2,4-Dichlorophenyl)-2-methyl-4-(5-methyl-3-trifluoromethylpyrazol-1-yl)-6,7-dihydro-5H-pyrrolo[2,3-d[pyrimidine (1-10-17)

To a suspension of NaH 80%/oil (6 mg) in anh. DMF, at r.t., under $N_2$, was added 3-methyl-5-(trifluoromethyl)pyrazole (22 mg). The reaction mixture was stirred at r.t. until gas evalution ceased (20 min). Intermediate 8 (15 mg) was then added and the reaction mixutre was heated at 100° C. (screw cap vial) for 18 hr. It was then cooled down to r.t. and poured into EtOAc. The organic layer was washed with sat.aq. NaCl (3×5 mL) and dried over anh. $Na_2SO_4$. The solids were filtered and the solvent evaporated. The crude product was purified by flash chromatography (silica gel, cHex/EtOAc 95:5) to give the title compound (0.013 g) as a yellow solid.

4-(4-Bromo-3-methylpyrazol-1-yl)-7-(2,4-dichlorophenyl)-2-methyl-6,7-dihydro-5H-pyrrolo[2,3-d]pyrimidine (1-10-18)

To a suspension of NaH 80%/oil (6 mg) in anh. DMF, at r.t., under $N_2$, was added 3-methyl-4-bromopyrazole (23 mg). The reaction mixture was stirred at r.t. until gas evalution ceased (20 min). Intermediate 8 (15 mg) was then added and the reaction mixutre was heated at 100° C. (screw cap vial) for 4 hr. It was then cooled down to r.t. and poured into EtOAc. The organic layer was washed with sat.aq. NaCl (3×5 mL) and dried over anh. $Na_2SO_4$. The solids were filtered and the solvent evaporated. The crude product was purified by flash chromatography (silica gel, cHex/EtOAc 95:5) to give the title compound as a yellow solid (0.018 g).

4-(4-Bromo-pyrazol-1-yl)-7-(2,4-Dichlorophenyl)-2-methyl-6,7-dihydro-5H-pyrrolo[2,3-d]pyrimidine (1-10-19)

3-Bromopyrazole (21 mg) was added to a suspension of NaH 80%/oil (4 mg) in anh. DMF (300 μL). After stirring for 30 min at r.t., intermediate 8 (15 mg) was added at and the resulting mixture was heated at 110° C. for 3 hr. The reaction was then concentrated in vacuo and the residue was diluted with $H_2O$ and extracted with $CH_2Cl_2$ (3×5 mL). The combined organic extracts were dried over anh. $Na_2SO_4$, the solids were filtered and the solvent evaporated. The tilte compound was obtained as a white solid (3.5 mg) after two chromatographic purifications (silica gel, EtOAc/cHex 95:5).

7-(2,4-Dichlorophenyl)-4-[3-(4-fluorophenyl)pyrazol-1-yl]-2-methyl-6,7-dihydro-5H-pyrrolo[2,3-d]pyrimidine (1-10-22)

3-(3-fluoro phenyl) pyrazole (3 eq, 0.19 mmol) was added to a suspension of NaH 80%/oil (6 mg, 3 eq) in anh. DMF (0.5 mL) at 0° C. After 10 min intermediate 8 (20 mg, 0.064 mmol) was added and the solution was heated in a sealed vial at 100° C. for 3 hr. The reaction mixture was diluted with water and extracted with EtOAc (3×). The combined organic extracts were dried over anh. $Na_2SO_4$, the solids were filtered and the solvent evaporated. The crude oil was purified by flash chromatography (silica gel, cHex/EtOAc 90:10). The title compound was obtained as a white solid (79%)

7-(2,4-Dichlorophenyl)-4-[3-(4-chlorophenyl)pyrazol-1-yl]-2-methyl-6,7-dihydro-5H-pyrrolo[2,3d]-pyrimidine (1-10-23)

3-(3-chloro phenyl) pyrazole (3 eq, 0.19 mmol) was added to a solution of NaH 80%/oil (6 mg, 3 eq) in anh. DMF (0.5 mL) at 0° C. After 10 min, intermediate 8 (20 mg, 0.064 mmol) was added and the solution was heated in a sealed vial at 100° C. for 3 hr. The reaction mixture was diluted with water and extracted with EtOAc (3×). The combined organic extracts were dried over anh. $Na_2SO_4$, the solids were filtered and the solvent evaporated. The crude oil was purified by flash chromatography (silica gel, cHex/EtOAc 90:10). The title compound was obtained as a white solid (60%).

1-7-(2,4-Dichlorophenyl)-2-methyl-6,7-dihydro-5H-pyrrolo[2,3-d]pyrimidin-4-yl]-1H-pyrazole-3-carbonitrile (1-10-27)

To a suspension of NaH 80%/oil (4 mg, 3 eq) in anh. DMF (0.3 mL), at r.t., under $N_2$, was added 3-cyano-pyrazole (14 mg, 3 eq) and the reaction mixture was stirred at r.t. for 30 min. Intermediate 8 (15 mg, 0.048 mmol) was added and the reaction mixture was stirred at 100° C. (screw cap vial) for 4 hr. The solvent was evaporated and the residue taken up in $H_2O$ and extracted with $CH_2Cl_2$ (3×). The combined organic extracts were dried over anh. $Na_2SO_4$, the solids were filtered and the solvent evaporated. The crude product was purified by flash chromatography (silica gel, cHex/EtOAc 8:2) to give the title compound as a white solid (11 mg, 62%).

N-{5-Cyclopropyl-2-7-(2,4-dichlorophenyl)-2-methyl-7H-pyrrolo[2,3d]pyrimidin-4-yl]-2H-pyrazole-3-yl}-acetamide (1-10-28)

To a suspension of NaH 95% (3.7 mg) in anh. DMF (0.5 mL) was added N-(5-cyclopropyl-2H-pyrazol-3-yl)-acetamide (24 mg) and the mixture was stirred for 20 min at r.t. Intermediate 8 (15 mg) was then added and the solution was heated in a sealed vial from 70° C. to 140° C. for 23 hr. It was then partitioned between $H_2O$ and EtOAc. The organic layer was washed with brine, dried with anh. $Na_2SO_4$ and the solvent was removed under reduced pressure. The crude compound was purified by flash chromatography (silica gel, cHex/EtOAc 2:8) to give the title compound as a white solid (14 mg).

All the analytical data are set forth in the following Table 1-10.

TABLE 1-10

| Cpd. No. | R | $R_1$ | $R_2$—$R_3$— | Analytical Data |
|---|---|---|---|---|
| 1-10-1 | 2,4-dichlorophenyl | CH$_3$ | 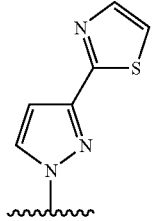 | NMR ($^1$H, CDCl$_3$): δ 8.74(d, 1H), 7.91(d, 1H), 7.53(d, 1H), 7.40(d, 1H), 7.37(d, 1H), 7.34(dd, 1H), 7.07(d, 1H), 4.11(t, 2H), 3.77(t, 2H), 2.53(s, 3H). MS (m/z): 429 [MH]$^+$. |
| 1-10-2 | 2,4-bis-trifluoro-methylphenyl | CH$_3$ | 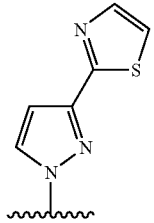 | NMR ($^1$H, CDCl$_3$): δ 8.69(d, 1H), 8.06(bs, 1H), 7.93(bd, 1H), 7.91(d, 1H), 7.59(d, 1H), 7.37(d, 1H), 7.05(d, 1H), 4.06(t, 2H), 3.79(t, 2H). MS (m/z): 497 [MH]$^+$. |
| 1-10-3 | 2,4-dichlorophenyl | CH$_3$ | 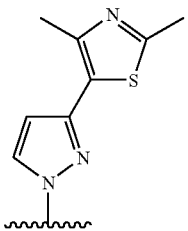 | NMR ($^1$H, CDCl$_3$): δ 8.63(d, 1H), 7.50(d, 1H), 7.38(d, 1H), 7.32(dd, 1H), 6.59(d, 1H), 4.05(t, 2H), 3.69(t, 2H), 2.69(s, 3H), 2.67(s, 3H), 2.46(s, 3H). MS (m/z): 457 [MH]$^+$ (2Cl). |
| 1-10-4 | 2,4-dichlorophenyl | CH$_3$ | 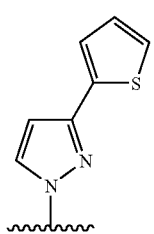 | NMR ($^1$H, CDCl$_3$): δ 9.62(d, 1H), 7.52(d, 1H), 7.43(dd, 1H), 7.40(d, 1H), 7.33(d, 1H), 7.31(dd, 1H), 7.10(dd, 1H), 6.68(d, 1H), 4.07(t, 2H), 3.75(t, 2H), 2.48(s, MS (m/z): 428 [MH$^+$ (2Cl). |
| 1-10-5 | 2,4-dichlorophenyl | CH$_3$ | 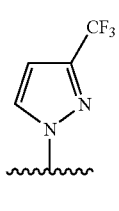 | NMR ($^1$H,): δ 8.65(m, 1H), 7.51(d, 1H), 7.38(d, 1H), 7.33(dd, 1H), 6.68(m, 1H), 4.04(t, 2H), 3.65(t, 2H), 2.46(s, 3H). IR( ,cm$^{-1}$): 1570, 1626. MS (m/z): 414 [MH$^+$. |
| 1-10-6 | 2-bromo-4-iso-propylphenyl | CH$_3$ | 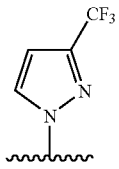 | NMR ($^1$H, CDCl$_3$): δ 8.67(d, 1H), 7.54(d, 1H), 7.30(d, 1H), 7.25(dd, 1H), 6.69(d, 1H), 4.05(t, 2H), 3.65(t, 2H), 2.93(m, 1H), 2.47(s, 3H), 1.28(d, 6H). MS (m/z): 466 [MH]$^+$, 1Br. |

TABLE 1-10-continued

| Cpd. No. | R | R$_1$ | R$_2$—R$_3$— | Analytical Data |
|---|---|---|---|---|
| 1-10-7 | 2,4-dichlorophenyl | CH$_3$ | 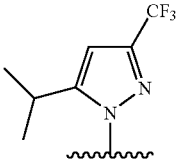 | Isomer1 (5-isoprapyl-3-trifluoromethyl): δ 7.52(d, 1H), 7.37(d, 1H), 7.34(dd, 1H), 6.47(s, 1H), 4.03(t, 2H), 4.00(m, 1H), 3.53(t, 2H), 2.45(s, 3H), 1.33(d, 3H), 1.31(d, 3H).<br>Isomer2 (3-isopropyl-5-trifluoromethyl): δ 7.51(d, 1H), 7.39(d, 1H), 7.31(dd, 1H), 6.69(s, 1H), 4.02(t, 2H), 3.51(t, 2H), 3.03 (m, 1H), 2.45(s, 3H), 1.33(d, 3H), 1.31(d, 3H).<br>MS (m/z): 456 [MH]$^+$. |
| 1-10-8 | 2,4-dichlorophenyl | CH$_3$ | 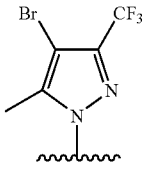 | NMR ($^1$H, CDCl$_3$): δ 7.52(d, 1H), 7.36(d, 1H), 7.33(dd, 1H), 4.03(t, 2H), 3.52(t, 2H), 2.72(s, 3H), 2.45(s, 3H).<br>MS (m/z): 506 [MH]$^+$. |
| 1-10-9 | 2,4-dichlorophenyl | CH$_3$ | 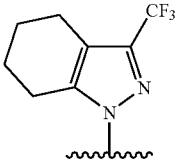 | NMR ($^1$H, CDCl$_3$): δ 7.51(d, 1H), 7.39(d, 1H), 7.32(dd, 1H), 6.68(s, 1H), 4.03(t, 2H), 3.53(t, 2H), 2.73(q, 2H), 2.45(s, 3H), 1.31(t, 3H).<br>MS (m/z): 442 [MH]$^+$. |
| 1-10-10 | 2,4-dicbloropbenyl | CH$_3$ | 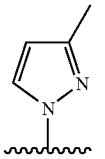 | NMR ($^1$H, CDCl$_3$): δ 8.49(d, 1H), 7.50(d, 1H), 7.39(d, 1H), 7.31(dd, 1H), 6.23(d, 1H), 4.02(t, 2H), 3.64(t, 2H), 2.46(s, 3H), 2.37(s, 3H).<br>MS (m/z): 360 [MH]$^+$ (2Cl). |
| 1-10-11 | 2,4-dichlorophenyl | CH$_3$ | 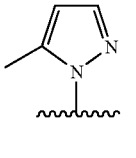 | NMR ($^1$H, CDCl$_3$): δ 7.59(d, 1H), 7.51(d, 1H), 7.38(d, 1H), 7.32(dd, 1H), 6.17(bd, 1H), 4.01(t, 2H), 3.55(t, 2H), 2.70(s, 2.46(s, 3H).<br>MS (m/z): 360 [MH]$^+$ (2Cl). |
| 1-10-12 | 2,4-dichlorophenyl | CH$_3$ | 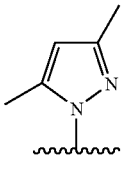 | NMR ($^1$H, CDCl$_3$): δ 7.49(d, 1H), 7.37(d, 1H), 7.30(dd, 1H), 5.96(s, 1H), 3.99(t, 2H), 3.54(t, 2H), 2.64(s, 3H), 2.44(s, 3H), 2.27(s, 3H).<br>MS (m/z): 374 [MH]$^+$ 2 Cl. |
| 1-10-13 | 2,4-dichlorophenyl | CH$_3$ | 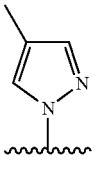 | NMR ($^1$H, CDCl$_3$): δ 8.38(m, 1H), 7.58 (bs, 1H), 7.50 (d, 1H), 7.39(d, 1H), 7.32 (dd, 1H), 4.02(t, 2H), 3.62(t, 2H), 2.46(s, MS (m/z): 360 [MH]$^+$ (2Cl). |
| 1-10-14 | 2,4-dichlorophenyl | CH$_3$ | 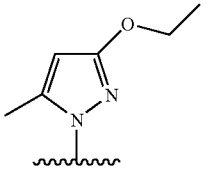 | NMR ($^1$H, CDCl$_3$): δ 7.48(d, 1H), 7.37(d, 1H), 7.29(dd, 1H), 5.63(s, 1H), 4.26(q, 2H), 3.96(t, 2H), 3.57(t, 2H), 2.66(s, 3H), 2.41(s, 3H), 1.40(t, 3H).<br>MS (m/z): 404 [MH]$^+$ (2Cl). |

TABLE 1-10-continued

| Cpd. No. | R | R₁ | R₂—R₃— | Analytical Data |
|---|---|---|---|---|
| 1-10-15 | 2,4-dichlorophenyl | CH₃ | (3-dimethoxymethyl-pyrazol-1-yl) | NMR (¹H, CDCl₃): δ 8.56(d, 1H), 7.50(d, 1H), 7.37(d, 1H), 7.31(dd, 1H), 6.51(d, 1H), 5.50(s, 1H), 4.02(t, 2H), 3.65(t, 2H), 3.43(s, 6H), 2.46(s, 3H).<br>MS (m/z): 420 [MH]⁺ (2Cl). |
| 1-10-16 | 2,4-dichlorophenyl | CH₃ | (3-ethyl-5-trifluoromethyl-pyrazol-1-yl) | NMR (¹H, CDCl₃): δ 7.51(d, 1H), 7.39(d, 1H), 7.32(dd, 1H), 6.68(s, 1H), 4.03(t, 2H), 3.53(t, 2H), 2.73(q, 2H), 2.45(s, 3H), 1.31(t, 3H).<br>MS (m/z): 442 [MH]⁺. |
| 1-10-17 | 2,4-dichlorophenyl | CH₃ | (3-trifluoromethyl-5-methyl-pyrazol-1-yl) | NMR (¹H,): δ 7.52(d, 1H), 7.37(d, 1H), 7.33(dd, 1H), 6.43(s, 1H), 4.03(t, 2H), 3.55(t, 2H), 2.72(s, 3H), 2.46(s, 3H).<br>MS (m/z): 428 [MH]⁺. |
| 1-10-18 | 2,4-dichlorophenyl | CH₃ | (4-bromo-3-methyl-pyrazol-1-yl) | NMR (¹H,): δ 8.55(s, 1H), 7.50(d, 1H), 7.37(d, 1H), 7.31(dd, 1H), 4.01(t, 2H), 3.59(t, 2H), 2.43(s, 3H), 2.31(s, 3H).<br>MS (m/z): 440 [MH]⁺. |
| 1-10-19 | 2,4-dichlorophenyl | CH₃ | (4-bromo-pyrazol-1-yl) | NMR (¹H, CDCl₃): δ 8.63(s, 1H), 7.68(s, 1H), 7.50(d, 1H), 7.37(d, 1H), 7.32(dd, 1H), 4.03(t, 2H), 3.59(t, 2H), 2.44(s, 3H).<br>MS (m/z): 424 [MH]⁺. |
| 1-10-20 | 2,4-dichlorophenyl | CH₃ | (4-nitro-3-chloro-pyrazol-1-yl) | NMR (¹H, CDCl₃): δ 8.70(s, 1H), 7.5(d, 1H), 7.3-7.2(m, 2H), 4.00(t, 2H), 3.60(t, 2H), 2.40(s, 3H).<br>MS (m/z): 425 [MH]⁺ (3Cl). |
| 1-10-21 | 2,4-dichlorophenyl | CH₃ | (4-nitro-3-bromo-pyrazol-1-yl) | NMR (¹H, CDCl₃): δ 8.8, (s, 1H), 7.5(d, 1H), 7.3-7.2(m, 2H), 4.05(t, 2H), 3.10(t, 2H), 2.5(s, 3H).<br>MS (m/z): 468 [MH]⁺ (1Cl, 1Br). |
| 1-10-22 | 2,4-dichlorophenyl | CH₃ | (3-(4-fluorophenyl)-pyrazol-1-yl) | NMR (¹H, CDCl₃): δ 8.64(d, 1H), 7.88 (dd, 2H), 7.51(d, 1H), 7.39(d, 1H), 7.32 (dd, 1H), 7.13(t, 2H), 6.72(d, 1H), 4.07(t, 2H), 3.77(t, 2H), 2.48(s, 3H).<br>MS (m/z): 440 [MH]⁺ (2Cl). |

TABLE 1-10-continued

| Cpd. No. | R | R₁ | R₂—R₃— | Analytical Data |
|---|---|---|---|---|
| 1-10-23 | 2,4-dichlorophenyl | CH₃ | (4-chlorophenyl-pyrazolyl) | NMR (¹H, CDCl₃): δ 8.64(d, 1H), 7.84(d, 2H), 7.51(d, 1H), 7.40(m, 3H), 7.32(dd, 1H), 6.75(d, 1H), 4.07(t, 2H), 3.76(t, 2H), 2.48(s, 3H). MS (m/z): 456 [MH]⁺ (3Cl). |
| 1-10-24 | 2,4-dichlorophenyl | CH₃ | (2-nitrophenyl-pyrazolyl) | NMR (¹H, CDCl₃): δ 8.67(d, 1H), 7.77 (dd, 1H), 7.68(dd, 1H), 7.62(dt, 1H), 7.50 (d, 1H), 7.37(d, 1H), 7.31(dd, 1H), 6.69 (d, 1H), 4.05(t, 2H), 3.57(t, 2H), 2.46(s, 3H). MS (m/z): 467 [MH]⁺ (1Cl). |
| 1-10-25 | 2,4-dichlorophenyl | CH₃ | (5-nitro-2-methoxyphenyl-pyrazolyl) | NMR (¹H, CDCl₃): δ 9.00(d, 1H), 8.67(d, 1H), 8.24(dd, 1H), 7.51(d, 1H), 7.40(d, 1H), 7.33(dd, 1H), 7.07(d, 1H), 7.05(d, 1H), 4.10(t, 2H), 4.07(s, 3H), 3.80(t, 1H), 2.48(s, 3H). MS (m/z): 497 [MH]⁺ (2Cl). |
| 1-10-26 | 2,4-dichlorophenyl | CH₃ | (4-pyridyl-pyrazolyl) | NMR (¹H, CDCl₃): δ 8.87(d, 1H), 8.77(d, 2H), 8.31(d, 2H), 7.55(d, 1H), 7.40(d, 1H), 7.36(dd, 1H), 7.06(d, 1H), 4.14(t, 2H), 3.78(t, 2H), 2.52(s, 3H). MS (m/z): 423 [MH]⁺ (2Cl). |
| 1-10-27 | 2,4-dichlorophenyl | CH₃ | (3-cyano-pyrazolyl) | NMR (¹H, CDCl₃): δ 8.74(d, 1H), 7.53 (dd, 1H), 7.4-7.3(m, 2H), 6.83(d, 1H) 4.09 (t, 2H), 3.66(t, 2H), 2.49(s, 3H). MS (m/z): 371 [MH]⁺ (2Cl). |
| 1-10-28 | 2,4-dichlorophenyl | CH₃ | (5-cyclopropyl-3-acetamido-pyrazolyl) | NMR (¹H, CDCl₃): δ 7.62(bs, 1H), 7.50(d, 1H), 7.39(d, 1H), 7.32(dd, 1H), 6.46(s, 1H), 3.99(t, 2H), 3.47(t, 2H), 2.83(m, 1H), 2.45(s, 3H), 2.17(s, 3H), 1.03-0.8 (m, 4H). IR (CDCl₃, cm⁻¹): 3432, 1691. MS (m/z): 443 [MH]⁺. |

TABLE 1-10-continued

| Cpd. No. | R | $R_1$ | $R_2\text{---}R_3\text{---}$ | Analytical Data |
|---|---|---|---|---|
| 1-10-29 | 2-(3,5-dichloro-pyridine) | $CH_3$ | (thiazole-pyrazole) | NMR ($^1$H, CDCl$_3$): δ 8.69(d, 1H), 8.36(d, 1H), 7.91(d, 1H), 7.85(d, 1H), 7.38(d, 1H), 7.05(d, 1H), 4.27(t, 2H), 3.75(t, 2H), 2.56(s, 3H). MS (m/z): 430 [M]$^+$. |
| 1-10-30 | 3-(2,6-bismethoxy-pyridine) | $CH_3$ | (thiazole-pyrazole) | NMR ($^1$H, CDCl$_3$): δ 8.70(ba, 1H), 7.88(d, 1H), 7.63(d, 1H), 7.36(d, 1H), 7.04(d, 1H), 6.39(d, 1H), 4.04(1, 2H), 3.96(t, 3H), 3.94(t, 3H), 3.69(t, 2H), 2.51(s, 3H). MS (m/z): 422 [MH]$^+$. |
| 1-10-31 | 2,4-bis-trifluoro-methylphenyl | $CH_3$ | (morpholine-pyrazole) | NMR ($^1$H, CDCl$_3$): δ 8.46(d, 1H), 8.02(bs, 1H), 7.9(bd, 1H), 7.56(d, 1H), 5.96(d, 1H), 3.98(t, 2H), 3.87(t, 4H), 3.67(t, 2H), 3.30(t, 4H), 2.41(s, 3H). MS (m/z): 500 [MH]$^+$. |
| 1-10-32 | 2,4-bis-trifluoro-methylphenyl | $CH_3$ | (pyridine-pyrazole) | NMR ($^1$H, CDCl$_3$): δ 9.17(bs, 1H), 8.70(d, 1H), 8.62(d, 1H), 8.20(d, 1H), 8.06(bs, 1H), 7.93(d, 1H), 7.59(d, 1H), 7.41(dd, 1H), 6.84(d, 1H), 4.06(t, 2H), 3.82(t, 2H), 2.47(s, 3H). MS (m/z): 491 [MH]$^+$. |
| 1-10-33 | 2,4-bis-trifluoro-methylphenyl | $CH_3$ | (pyrazine-pyrazole) | NMR ($^1$H, CDCl$_3$): δ 9.36(d, 1H), 8.73(d, 1H), 8.61(dd, 1H), 8.54(d, 1H), 8.06(sa, 1H), 7.94(d, 1H), 7.59(d, 1H), 7.16(d, 1H), 4.07(t, 2H), 3.82(t, 2H), 2.47(s, 3H). MS (m/z): 492 [MH]$^+$. |
| 1-10-34 | 2-(3-chloro-5-trifluoromethyl-pyridine) | $CH_3$ | (thiazole-pyrazole) | NMR ($^1$H, DMSO-d$_6$): δ 8.70(d, 1H), 8.63 (d, 1H), 8.04(d, 1H), 7.91(d, 1H), 7.38(d, 1H), 7.06(d, 1H), 4.35(t, 2H), 3.76(t, 2H), 2.55(s, 3H). MS (m/z): 464 [MH]$^+$. |

TABLE 1-10-continued

| Cpd. No. | R | R₁ | R₂—R₃— | Analytical Data |
|---|---|---|---|---|
| 1-10-35 | 2,4-bis-trifluoromethylphenyl | CH₃ | (4-methyl-4H-1,2,4-triazol-3-yl attached to pyrazole) | NMR (¹H, CDCl₃): δ 8.76(d, 1H) 8.43(s, 1H), 8.06(s, 1H), 7.94(d, 1H), 7.58(d, 1H), 7.26(d, 1H), 4.16(s, 3H), 4.05(t, 2H), 3.69(t, 2H), 2.47(s, 3H).<br>MS (m/z): 495 [MH]⁺. |
| 1-10-36 | 2,4-bis-trifluoromethylphenyl | CH₃ | (1-methylimidazol-2-yl attached to pyrazole) | NMR (¹H, CDCl₃): δ 8.72(d, 1H), 8.06(d, 1H), 7.94(dd, 3H), 7.58(d, 1H), 7.5 (broad, 1H), 7.30(bs, 1H), 7.05(bs, 1H), 4.19(s, 3H), 4.04(t, 2H), 3.70(t, 2H), 2.46 (s, 3H).<br>MS (m/z): 494 [MH]⁺, 238, 414. |
| 1-10-37 | 2,4-bis-trifluoromethylphenyl | CH₃ | (imidazol-2-yl attached to pyrazole) | NMR (¹H, CDCl₃): δ 8.63(d, 1H), 8.05(d, 1H), 7.92(dd, 1H), 7.57(d, 1H), 7.22(s, 2H), 7.21(bs, 1H), 4.03(t, 2H), 3.74(t, 2H), 2.44(s, 3H).<br>MS (m/z): 480 [MH]⁺, 414 |
| 1-10-38 | 2,4-bis-trifluoromethylphenyl | CH₃ | (1,3,4-oxadiazol-2-yl attached to pyrazole) | NMR (¹H,CDCl₃): δ 8.76(d, 1H) 8.50(s, 1H), 8.04(s, 1H), 7.93(d, 3H), 7.57(d, 1H), 7.12(d, 1H), 4.05(t, 2H), 3.77(t, 2H), 2.45(s, 3H).<br>MS (m/z): 482 [MH]⁺. |
| 1-10-39 | 3-(2-trifluoromethylpyridine) | CH₃ | (thiazol-2-yl attached to pyrazole) | NMR (¹H, CDCl₃): 8.97(s, 1H), 8.79(d, 1H), 8.70(d, 1H), 7.91(d, 1H), 7.62(s, 1H), 7.31(d, 1H), 7.00(d, 1H), 4.16(t, 2H), 3.78(t, 2H), 2.52(s, 3H).<br>MS (m/z): 430 [MH]⁺. |
| 1-10-40 | 2,4-bis-trifluoromethylphenyl | CH₃ | (oxazol-5-yl attached to pyrazole) | NMR (¹H, Acetone-d₆): δ 8.76(d, 1H) 8.28 (s, 1H), 8.20(m, 2H), 7.95(d, 1H), 7.61(s, 1H), 6.91(d, 1H), 4.17(t, 2H), 3.67(t, 2H), 3.75(t, 2H), 2.35(s, 3H).<br>MS (m/z): 481 [MH]⁺. |

Synthesis of Representative Compounds of Structure (1-11)

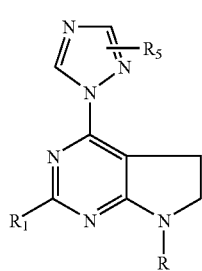

(1-11)

7-(2,4-Dichlorophenyl-2-methyl-4-(3-trifluoromethyl(1,2,4)triazol-1-yl)-6,7-dihydro-5H-pyrrolo-2,3-d)pyrimidine (1-11-2)

A solution of intermediate 8 (30 mg, 0.095 mmol) and hydrazine hydrate (0.095 mmol) in methanol (950 µl) was heated at 130° C. (screw cap vial) for 18 hr. The mixture was then evaporated to dryness and the crude product obtained together with formyltrifluoroacetylimide (43 mg, 0.3 mmol) in N-methylpyrrolidone (200 µl) were heated at 100° C. (screw cap vial) for 5 hr. The mixture was then diluted with cold brine and extracted with EtOAc (3×). The combined organic extracts were dried over anh. $Na_2SO_4$, then filtered and the solvent evaporated in vacuo. The crude compound was purified by flash chromatography (silica gel, EtOAc/cHex 9:1) to give the title compound as a white solid (99%).

The compound 1-11-1, whose analytical data are reported in the following Table 1-11, was prepared analogously using diacetamide instead of formyltrifluoroacetylimide.

All the analytical data are set forth in the following Table 1-11.

TABLE 1-11

| Cpd. No. | R | $R_1$ | $R_2$–$R_3$— | Analytical Data |
|---|---|---|---|---|
| 1-11-1 | 2,4-dichlorophenyl | $CH_3$ | (structure) | NMR($^1$H, $CDCl_3$): δ7.51(d, 1H), 7.37(d, 1H), 7.33(dd, 1H), 4.02(t, 2H), 3.54(t, 2H), 2.84(s, 3H), 2.46(s, 3H), 2.40(s, 3H). MS(m/z): 375[MH]$^+$. |
| 1-11-2 | 2,4-dichlorophenyl | $CH_3$ | (structure, $CF_3$) | NMR($^1$H, $CDCl_3$): 8.13δ(s, 1H), 7.54δ(d, 1H), 7.38δ(d, 1H), 7.35δ(dd, 1H), 4.08δ(t, 2H), 3.48δ(t, 2H), 2.47δ(s, 3H). MS(m/z): 415[MH]$^+$(2Cl). |

Synthesis of Representative Compounds of Structure (1-12)

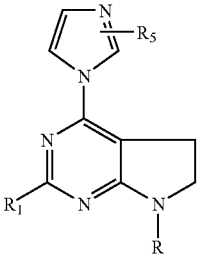

(1-12)

7-(2,4-Dichlorophenyl)-2-methyl-4-(2-methyl-imidazol-1-yl)-6,7-dihydro-5H-pyrrolo[2,3-d]pyrimidine (1-12-3)

To a suspension of NaH 80%/oil (3 mg, 2 eq) in anh DMF (0.5 mL), at r.t., under $N_2$, was added 2-methyl-imidazole (8 mg, 2 eq) and the reaction mixture was stirred for 20 min at r.t. Intermediate 8 (15 mg, 0.048 mmol) was then added and the reaction mixture was heated at 80° C. (screw cap vial) for 90 min. It was then cooled down to r.t. and poured into EtOAc/sat.aq. NaCl. The phases were separated and the organic layer was washed with sat.aq. NaCl (2×) and dried over anh. $Na_2SO_4$. The solids were filtered and the solvent evaporated. The residue was purified by flash chromatography (silica gel, 8% MeOH/EtOAc) to give 6 mg of the title compound as a white solid (0.017 mmol, 35%)

The compounds 1-12-1, 1-12-2, 1-12-4, 1-12-5, 1-12-6 and 1-12-7, whose analytical data are reported in the following Table 1-12, were prepared analogously starting from the appropriate imidazole.

1-[7-(2,4-Dichlorophenyl)-2-methyl-6,7-dihydro-5H-pyrrolo[2,3-d]pyrimidin-4-yl]-1H-imidazole-4-carboxylic acid phenylamide (1-12-8)

To a suspension of NaH 95% (3.7 mg) in anh. DMF (0.5 mL) was added 1H-imidazole-4-carboxylic acid phenylamide (27 mg) and the mixture was stirred for 20 min at r.t. Intermediate 8 (15 mg) was then added and the solution was heated in a sealed vial from 70 to 120° C. for 6 hr. It was then partitioned between $H_2O$ and EtOAc. The organic layer was washed with brine, dried with anh. $Na_2SO_4$ and the solvent was removed under reduced pressure. The crude compound was purified by flash chromatography (silica gel, cHex/EtOAc 1:9) to give the title compound (9.8 mg) as a yellow solid.

All the analytical data are set forth in the following Table 1-12.

TABLE 1-12

| Cpd. No. | R | $R_1$ | $R_2$–$R_3$— | Analytical Data |
|---|---|---|---|---|
| 1-12-1 | 2,4-dichlorophenyl | $CH_3$ | (structure) | NMR($^1$H, $CDCl_3$): δ7.51(dd, 1H), 7.37(dd, 1H), 7.32(dd, 1H), 7.07(d, 1H), 7.04(d, 1H), 4.01(t, 2H), 3.16(t, 2H), 2.90(q, 2H), 2.45(s, 3H), 1.32(t, 3H). MS(m/z): 374[MH]$^+$(2Cl). |

TABLE 1-12-continued

| Cpd. No. | R | $R_1$ | $R_2$–$R_3$— | Analytical Data |
|---|---|---|---|---|
| 1-12-2 | 2,4-dichloro-phenyl | CH$_3$ | 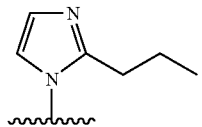 | NMR($^1$H, CDCl$_3$): δ7.50(d, 1H), 7.36(d, 1H), 7.31(dd, 1H), 7.07(d, 1H), 7.04(d, 1H), 4.02(t, 2H), 3.16(t, 2H), 2.88(dd, 2H), 2.46(s, 3H), 1.75 (m, 2H), 0.93(t, 3H). MS(m/z): 388[MH]$^+$(2Cl). |
| 1-12-3 | 2,4-dichloro-phenyl | CH$_3$ | 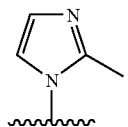 | NMR($^1$H, CDCl$_3$): δ7.52(d, 1H), 7.38 (d, 1H), 7.34(dd, 1H), 7.11(d, 1H), 7.03(d, 1H), 4.04(t, 2H), 3.21(t, 2H), 2.58(s, 3H), 2.47(s, 3H). MS(m/z): 360[MH]$^+$2Cl. |
| 1-12-4 | 2,4-dichloro-phenyl | CH$_3$ | 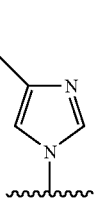 | NMR($^1$H, CDCl$_3$): δ8.31(s, 1H), 7.52 (d, 1H), 7.50(s, 1H), 7.37(d, 1H), 7.33(dd, 1H), 4.09(t, 2H), 3.73(t, 2H), 3.42(t, 2H), 3.40(s, 3H), 2.94(t, 2H), 2.46(s, 3H). MS(m/z): 404[MH]$^+$(2Cl). |
| 1-12-5 | 2,4-dichloro-phenyl | CH$_3$ | 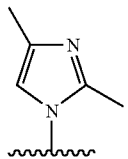 | NMR($^1$H, CDCl$_3$): δ7.53(d, 1H), 7.38 (d, 1H), 7.34(dd, 1H), 6.83(s, 1H), 4.04(t, 2H), 3.22(t, 2H), 2.56(s, 3H), 2.47(s, 3H), 2.23(s, 3H). MS(m/z): 374[MH]$^+$. |
| 1-12-6 | 2,4-dichloro-phenyl | CH$_3$ | 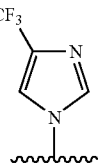 | NMR($^1$H, CDCl$_3$): δ8.34(s, 1H), 8.05 (s, 1H), 7.54(s, 1H), 7.36(m, 2H), 4.13 (t, 2H), 3.45(t, 2H), 2.47(s, 3H). MS(m/z): 415[MH]$^+$(2Cl) |
| 1-12-7 | 2,4-dichloro-phenyl | CH$_3$ | 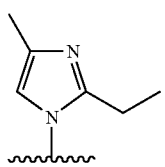 | NMR($^1$H, CDCl$_3$): δ7.52(d, 1H), 7.38(d, 1H), 7.33(dd, 1H), 6.79(s, 1H), 4.03(t, 2H), 3.19(t, 2H), 2.90(q, 2H), 2.46(s, 3H), 2.24(s, 3H)1.31(t, 3H). MS(m/z): 388[MH]$^+$. |

TABLE 1-12-continued

| Cpd. No. | R | $R_1$ | $R_2$-$R_3$— | Analytical Data |
|---|---|---|---|---|
| 1-12-8 | 2,4-dichloro-phenyl | CH$_3$ | (structure) | NMR($^1$H, CDCl$_3$): δ9.02(bs, 1H), 8.48(d, 1H), 8.26(d, 1H), 7.74(d, 2H), 7.54(d, 1H), 7.38(t, 2H), 7.36(d, 1H), 7.25(d, 1H), 7.14(t, 1H), 4.13(t, 2H), 3.48(t, 2H), 2.48(s, 3H). IR(CDCl$_3$, cm$^{-1}$): 3389, 1674. MS(m/z): 465[MH]$^+$. |

EXAMPLE 2

Synthesis of Representative Compounds of Structure (Ia-2)

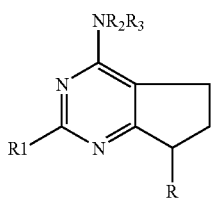

(Ia-2)

Synthesis of Representative Compounds of Structure (2-1)

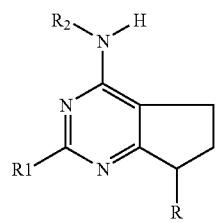

(2-1)

Representative compounds of this invention were prepared by the procedure set forth above for the compounds of general formula (2-2).

All the analytical data are set forth in the following Table 2-1.

Synthesis of Representative Compounds of Structure (2-2)

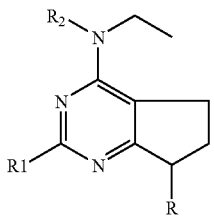

(2-2)

Butyl-[7-(2,4-dichlorophenyl)-2-methyl-6,7-dihydro-5H-cyclopentapyrimidin-4-yl]-ethyl-amine (2-2-5)

Intermediate 34 (12 mg, 0.04 mmol) was dissolved in 300 μl of butylethylamine and heated at 160° C. (screw cap vial) for 18 hr. The reaction mixture was diluted with water and extracted with CH$_2$Cl$_2$ (3×). The combined organic extracts were dried over anh. Na$_2$SO$_4$, the solids were filtered and the solvent evaporated. The crude oil was purified by flash chromatography (silica gel, cHex/EtOAc 85:15) to give the title compound (6 mg, 40%) as a yellow oil.

The compounds 2-1-1, 2-2-1, 2-2-2, 2-2-3, 2-2-4, 2-2-6 and 2-2-7, whose analytical data are reported in the following Table 2-2, were prepared analogously starting from the appropriate amine.

In particular a differently substituted Grignard reagent, (intermediate 41), phenyl acetic ester (intermediate 31) or phenyl boronic acid (intermediate 35) was used:

compound 2-2-1: methyl 2,4-difluorophenylacetate (commercially available);

compound 2-2-2: 2-bromo-5-fluorotoluene (commercially available);

TABLE 2-1

| Cpd. No. | R | $R_1$ | $R_2$— | $R_3$— | Analytical Data |
|---|---|---|---|---|---|
| 2-1-1 | 2,4-dichloro-phenyl | CH$_3$ | (cyclopropylmethyl) | H | NMR($^1$H, CDCl$_3$): δ7.38(d, 1H), 7.12 (dd, 1H), 6.76(d, 1H), 4.64(m, 1H), 4.51(br t, 1H), 3.40(m, 2H), 2.80(m, 2H), 2.66(m, 1H), 2.50(s, 3H), 1.84 (m, 1H), 1.10(m, 1H), 0.58(m, 2H), 0.30(m, 2H). MS(m/z): 348[MH]$^+$. | compound 2-2-3: 2-bromo-5-methyltoluene (commercially available);

compound 2-2-4: 1-bromo-2,4-dimethoxybenzene (commercially available);

compound 2-2-7: 1-bromo-3,4-dimethoxybenzene (commercially available).

All the analytical data are set forth in the following Table 2-2.

TABLE 2-2

| Cpd. No. | R | $R_1$ | $R_2$— | $R_3$— | Analytical Data |
|---|---|---|---|---|---|
| 2-2-1 | 2,4-bistrifluoromethylphenyl | $CH_3$ | 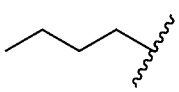 | Et | NMR($^1$H, $CDCl_3$): δ6.88(m, 1H), 6.77(m, 2H), 4.40(t, 1H), 3.6(m, 2H), 3.5(m, 2H), 3.03(m, 2H), 2.52(m, 1H), 2.42(s, 3H), 1.86(m, 1H), 1.60 (m, 2H), 1.35(m, 2H), 1.19(t, 3H), 0.95(t, 3H). MS(m/z): 346[MH]$^+$. |
| 2-2-2 | 2-methyl-4-fluorophenyl | $CH_3$ | 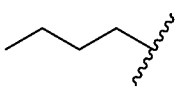 | Et | NMR($^1$H, $CDCl_3$): δ6.88(dd, 1H), 6.75(td, 1H), 6.64(dd, 1H), 4.32(m, 1H), 3.64(m, 2H), 3.54(m, 2H), 3.02 (m, 2H), 2.52(m, 1H), 2.45(s, 3H), 2.39(s, 3H), 1.78(m, 1H), 1.65(m, 2H), 1.36(m, 2H), 1.20(t, 3H), 0.96(t, 3H). MS(m/z): 342[MH]$^+$. |
| 2-2-3 | 2,4-isopropylphenyl | $CH_3$ | 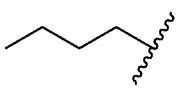 | Et | NMR($^1$H, $CDCl_3$): δ6.98(d, 1H), 6.86 (dd, 1H), 6.56(d, 1H), 4.32(m, 1H), 3.70–3.44(m, 2H+2H), 3.02(m, 2H), 2.50(m, 1H), 2.42(s, 3H), 2.35(s, 3H), 2.25(s, 3H), 1.8(m, 1H), 1.6(m, 2H), 1.35(m, 2H), 1.19(t, 3H), 0.96(t, 3H). MS(m/z): 338[MH]$^+$(100%). |
| 2-2-4 | 2,4-dimethoxyphenyl | $CH_3$ | 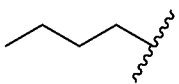 | Et | NMR($^1$H, $CDCl_3$): δ6.67(d, 1H), 6.46(d, 1H), 6.38(dd, 1H), 4.44(dd, 1H), 3.79(s, 3H), 3.78(s, 3H), 3.67-3.44(m, 4H), 3.00(m, 2H), 2.45(m, 1H), 2.44(s, 3H), 1.83(m, 1H), 1.6(m, 2H), 1.36(m, 2H), 1.20(t, 3H), 0.97(t, 3H). MS(m/z): 370[MH]$^+$. |
| 2-2-5 | 2,4-dichlorophenyl | $CH_3$ | 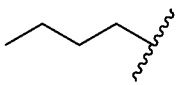 | Et | NMR($^1$H, $CDCl_3$): δ7.39(d, 1H), 7.12 (dd, 1H), 6.76(d, 1H), 4.56(m, 1H), 3.58(m, 4H), 3.02(m, 2H), 2.60(m, 1H), 2.45(s, 3H), 1.79(m, 1H), 1.62 (m, 2H), 1.37(m, 2H), 1.21(t, 3H), 0.98(t, 3H). MS(m/z): 378[MH]$^+$(2Cl) |
| 2-2-6 | 2,4-dichlorophenyl | $CH_3$ |  | Et | NMR($^1$H, CDCl3): δ7.37(d, 1H), 7.15(dd, 1H), 6.84(d, 1H), 4.98(s, 1H), 4.97(bm, 2H), 4.74(s, 1H), 4.15 (bm, 2H), 3.72(bm, 2H), 3.09(m, 2H), 2.68(bs, 3H), 2.56(bm, 1H), 2.04(bm, 1H), 1.75(s, 3H), 1.26(t, 3H). MS(m/z): 376[MH]$^+$(2Cl). |
| 2-2-7 | 3,4-dimethoxyphenyl | $CH_3$ | 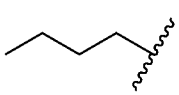 | Et | MS(m/z): 370[MH]$^+$ |

Synthesis of Representative Compounds of Structure (2-3)

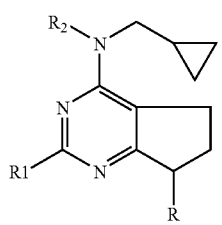

(2-3)

Cyclopropylmethyl-[7-(2,4-dimethoxy-phenyl)-2-methyl-6,7-dihydro-5H-cyclopentapyrimidin-4-yl]-propyl-amine (2-3-5)

Intermediate 44 (16 mg, 0.053 mmol) and cyclopropylmethyl-propylamine (75 μL, 10 eq) in DMSO (1 mL) were heated at 100° C. (screw cap vial) for 18 hr. The reaction mixture was taken up in EtOAc and washed with sat.aq. NaCl (2×). The organic layer was dried over anh. $Na_2SO_4$, the solids were filtered and the solvent evaporated. The crude product was purified by flash chromatography (silica gel, cHex/EtOAc 8:2) to give the title compound as a clear oil (10 mg, 50%).

Cyclopropylmethyl-[7-(2,4-dichlorophenyl)-2-methyl-6,7-dihydro-5H-cyclopentapyrimidin-4-yl]-propyl-amine (2-3-6)

Intermediate 34 (12 mg, 0.038 mmol) was dissolved in cyclopropylmethyl-propylamine (0.3 mL, 55 eq) and the mixture was stirred in a screw cap vial at 160° C. for 22 hr. The excess amine was evaporated and the residue was purified by flash chromatography (silica gel, gradient: cHex/EtOAc 95:5 to 9:1). The title compound was obtained as a colourless oil (7 mg, 0.018 mmol, 47%).

The compounds 2-3-1, 2-3-1, 2-3-3, 2-3-4 and 2-3-7, whose analytical data reported in the following Table 2-3, were prepared analogously starting from the appropriate amine.

In particular a differently substituted Grignard reagent, (intermediate 41), phenyl acetic ester (intermediate 31) or phenyl boronic acid (intermediate 35) was used:
- compound 2-3-1: 2-bromo-5-methyltoluene (commercially available);
- compound 2-3-2: methyl 2,4-difluorophenylacetate (commercially available);
- compound 2-3-3: 2-bromo-5-methyltoluene (commercially available);
- compound 2-3-4: 2-bromo-5-methyltoluene (commercially available);
- compound 2-2-7: 1-bromo-3,4-dimethoxybenzene (commercially available).

All the analytical data are set forth in the following Table 2-3.

TABLE 2-3

| Cpd. No. | R | $R_1$ | $R_2$— | $R_3$— | Analytical Data |
|---|---|---|---|---|---|
| 2-3-1 | 3-methyl-5-methyl-phenyl | $CH_3$ | propyl | cyclopropylmethyl | NMR($^1$H, $CDCl_3$): δ6.85(d, 1H), 6.73 (m, 2H), 4.05(dd, 1H), 3.45-3.7(m, 3H), 3.13(m, 1H), 3.05(m, 1H), 2.40 (s, 3H), 2.25(s, 6H), 2.00(m, 1H), 1.67(m, 2H), 1.10(m, 1H), 1.95(m, 5H), 0.55(m, 2H), 0.30(m, 2H). MS(m/z): 350[MH]$^+$. |
| 2-3-2 | 2,4-difluoro-phenyl | $CH_3$ | propyl | cyclopropylmethyl | NMR($^1$H, $CDCl_3$): δ6.87(m, 1H), 6.77(m, 2H), 4.40(t, 1H), 3.58(m, 2H), 3.45(m, 2H), 3.04(m, 2H), 2.55 (m, 1H), 2.43(s, 3H), 1.86(m, 1H), 1.65(m, 2H), 1.07(m, 1H), 0.92(t, 3H), 0.58(m, 2H), 0.27(m, 2H). MS(m/z): 358[MH]$^+$(100%). |
| 2-3-3 | 2,4-dimethyl-phenyl | $CH_3$ | propyl | cyclopropylmethyl | NMR($^1$H, $CDCl_3$): δ6.98(d, 1H), 6.87 (dd, 1H), 6.58(d, 1H), 4.33(m, 1H), 3.66-3.44(m, 2H+2H), 3.05(m, 2H), 2.50(m, 1H), 2.42(s, 3H), 2.35(s, 3H), 2.26(s, 3H), 1.85(m, 1H), 1.60 (m, 2H), 1.08(m, 1H), 0.91(t, 3H), 0.53(m, 2H), 0.29(m, 2H). MS(m/z): 350[MH]$^+$(100%) |
| 2-3-4 | 2-methyl-4-fluoro-phenyl | $CH_3$ | propyl | cyclopropylmethyl | NMR($^1$H, $CDCl_3$): δ6.87(dd, 1H), 6.74(td, 1H), 6.63(dd, 1H), 4.31(dd, 1H), 3.56(m, 2H), 3.51(dd, 2H), 3.04 (m, 2H), 2.50(m, 1H), 2.44(s, 3H), 2.38(s, 3H), 1.80(m, 1H), 1.66(q, 2H), 0.92(t, 3H), 1.08-0.85(m, 1H), 0.54(m, 2H), 0.29(m, 2H). MS(m/z): 353[M]$^+$. |
| 2-3-5 | 2,4-dimethoxy-phenyl | $CH_3$ | propyl | cyclopropylmethyl | NMR($^1$H, $CDCl_3$): δ6.64(d, 1H), 6.45 (d, 1H), 6.36(dd, 1H), 4.45(dd, 1H), 3.78(s, 3H), 3.76(s, 3H), 3.6-3.4(m, 2H), 3.55-3.49(m, 2H), 3.1-2.9(m, 2H), 2.45(m, 1H), 2.44(s, 3H), 1.81 (m, 1H), 1.66(m, 2H), 1.08(m, 1H), 0.91(t, 3H), 0.6-0.2(m, 4H). MS(m/z): 382[MH]$^+$. |

TABLE 2-3-continued

| Cpd. No. | R | $R_1$ | $R_2$— | $R_3$— | Analytical Data |
|---|---|---|---|---|---|
| 2-3-6 | 2,4-dichloro-phenyl | $CH_3$ | ~~~ | ▷~ | NMR($^1$H, CDCl$_3$): δ7.35(d, 1H), 7.10 (dd, 1H), 6.75(d, 1H), 4.55(dd, 1H), 3.65-3.40(m, 4H), 3.00(t, 2H), 2.60 (m, 1H), 2.40(s, 3H), 1.75(m, 1H), 1.60(m, 2H), 1.05(m, 1H), 0.90(t, 3H), 0.55(m, 2H), 0.25(m, 2H). MS(m/z): 390[MH]$^+$. |

Synthesis of Representative Compounds of Structure (2-4)

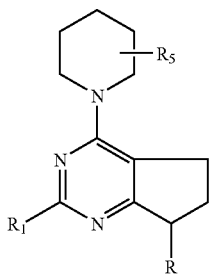

(2-4)

Representative compounds of this invention were prepared by the procedure set forth above for the compounds of general formula (2-1) (intermediate 41: phenyl magnesium bromide was used as the Grignard reagent).

All the analytical data are set forth in the following Table 2-4.

TABLE 2-4

| Cpd. No. | R | $R_1$ | $R_2$-$R_3$— | Analytical Data |
|---|---|---|---|---|
| 2-4-1 | phenyl | $CH_3$ | [morpholine] | NMR($^1$H, CDCl$_3$): δ7.27(m, 2H), 7.20(m, 1H), 7.13(d, 2H), 4.22(dd, 1H), 3.78(m, 4H), 3.75(m, 4H), 3.07 (m, 1H), 2.96(m, 1H), 2.54(m, 1H), 2.46(s, 3H), 2.05(m, 1H). MS(m/z): 295[MH]$^+$. |

Synthesis of Representative Compounds of Structure (2-5)

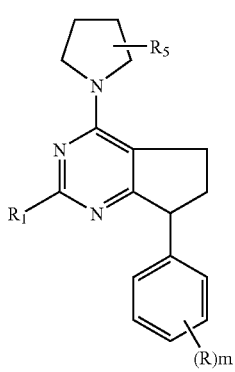

(2-5)

7-(2,4-Dichlorophenyl)-4-[(2R,5R)-2,5-dimethyl-pyrrolidin-1-yl]-2-methyl-6,7-dihydro-5H-cyclopentapyrimidine (2-5-1) and 7-(2,4-dichlorophenyl)-4-[(2R,5R)-2,5-dimethyl-pyrrolidin-1-yl]-2-methyl-6,7-dihydro-5H-cyclopentapyrimidine (2-5-2)

Intermediate 34 (27 mg, 0.086 mmol) was dissolved in anh. DMSO (0.3 mL). Enantiomerically pure (2R,5R)-(−)-2,5-dimethylpyrrolidine (0.1 mL, 10 eq) was added and the mixture was stirred in a screw cap vial at 160° C. for 4 hr. The mixture was cooled to r.t., diluted with EtOAc, washed with water (3×10 mL) and dried over anh. Na$_2$SO$_4$. The solids were filtered and the solvent evaporated. The two diastereoisomers were separated by flash chromatography (silica gel, cHex/EtOAc 9:1). The two title compounds were obtained as colourless oils (isomer 1: 11 mg, 0.029 mmol, 34%) (isomer 2: 13 mg, 0.035 mmol, 40%)

All the analytical data are set forth in the following Table 2-5.

TABLE 2-5

| Cpd. No. | R | $R_1$ | $R_2$-$R_3$— | Analytical Data |
|---|---|---|---|---|
| 2-5-1 | α-2,4-di-chloro-phenyl | $CH_3$ | [pyrrolidine] | NMR($^1$H, CDCl$_3$): δ7.39(d, 1H), 7.13 (dd, 1H), 6.75(d, 1H), 4.64(dd, 1H), 4.50(br s, 1H), 2.99(m, 2H), 2.65(m, 1H), 2.47(s, 3H), 2.22(m, 2H), 1.78 (m, 1H), 1.65(m, 2H), 1.15(br d, 6H). MS(m/z): 376[MH]$^+$. |
| 2-5-2 | β-2,4-di-chloro-phenyl | $CH_3$ | [pyrrolidine] | NMR($^1$H, CDCl$_3$): δ7.39(d, 1H), 7.12 (dd, 1H), 6.77(d, 1H), 4.54(dd, 1H), 4.50(br s, 1H), 2.95(m, 2H), 2.63(m, 1H), 2.48(s, 3H), 2.23(m, 2H), 1.81 (m, 1H), 1.66(m, 2H), 1.14(br d, 6H). MS(m/z): 376[MH]$^+$. |

EXAMPLE 3

Synthesis of Representative Compounds of Structure (Ib-1)

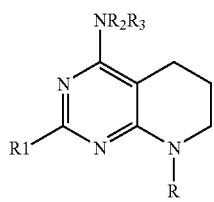
(Ib-1)

[8-(2,4-Bis-trifluoromethylphenyl)-2-methyl-5,6,7,8-tetrahydro-pyrido[2,3-d]pyrimidin-4-yl]-(1-propyl-butyl)amine (3-1-1)

A mixture of intermediate 51 (22 mg, 0.0505 mmol) and 4-heptylamine (150 μl) was heated at 130° C. (screw cap vial) for 18 hr. The crude oil was directly purified by flash chromatography (silica gel, cHex/EtOAc 95:5) to give the title compound as light yellow oil (7 mg, 30%).

Butyl[8-(2,4-dichlorophenyl)-2-methyl-5,6,7,8-tetrahydro-pyrido[2,3-d]pyrimidin-4-yl]ethyl-amine (3-1-2)

A mixture of intermediate 30 (8 mg) and n-butyl-ethylamine (300 μl) was heated in a sealed vial at 160° C. for 18 hr. The crude oil was directly purified by flash chromatography (silica gel, cHex/EtOAc 9:1) to give the title compound (4 mg) as a light yellow oil.

Cyclopropylmethyl[8-(2,4-dichlorophenyl)-2-methyl-5,6,7,8-tetrahydropyrido[2,3-d]-pyrimidin-4-yl]-propyl-amine (3-1-3)

Intermediate 30 (8 mg, 0.024 mmol) and cyclopropylmethyl-propyl-amine (300 μl) were heated at 160° C. (screw cap vial) for 18 hr. The crude oil was directly purified by flash chromatography (silica gel, cHex/EtOAc 9:1) to give the title compound as light yellow oil (4 mg, 41%).

All the analytical data are set forth in the following Table 3.

Synthesis of Representative Compounds of Structure (3-2)

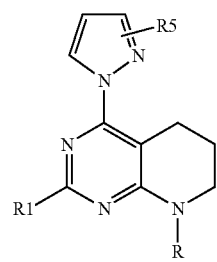
(3-2)

Representative compounds of this invention were prepared by the procedure set forth above for the compounds of general formula 1-10.

All the analytical data are set forth in the following Table 3-2.

TABLE 3-2

| Cpd. No. | R | $R_1$ | $R_2$-$R_3$— | Analytical Data |
|---|---|---|---|---|
| 3-2-1 | 2,4-bis-trifluoro-methylphenyl | $CH_3$ | (pyrazolyl with CF$_3$) | NMR($^1$H, CDCl$_3$): δ8.45(d, 1H), 8.04/7.93(bs/bd, 2H), 7.43(d, 1H), 6.69(d, 1H), 3.67(m, 2H), 3.21(m, 2H), 2.28/2.11(s/m, 5H). MS(m/z): 496[MH]$^+$. |

TABLE 3

| Cpd. No. | R | $R_1$ | $R_2$— | $R_3$— | Analytical Data |
|---|---|---|---|---|---|
| 3-1-1 | 2,4-bistrifluoro-methylphenyl | $CH_3$ | (4-heptyl) | H | NMR($^1$H, CDCl$_3$): δ7.96(d, 1H), 7.79(dd, 1H), 7.39(d, 1H), 4.31(m, 1H), 3.86(da, 1H), 3.51(m, 2H), 2.39 (m, 2H), 2.15(m, 2H), 2.13(s, 3H), 1.5-1.2(m, 8H), 0.88(t, 6H). MS(m/z): 475[MH]$^+$. |
| 3-1-2 | 2,4-dichloro-phenyl | $CH_3$ | (butyl) | Et | NMR($^1$H, CDCl$_3$): δ7.4-7.2(m, 3H), 3.63(bm, 1H), 3.50(bm, 1H), 3.32-3.26(m, 4H), 2.63(m, 2H), 2.21(s, 3H), 2.00(m, 2H), 1.5(m, 2H), 1.30 (m, 2H), 1.14(t, 3H), 0.92(t, 3H). MS(m/z): 405[MH]$^+$, 2Cl. |
| 3-1-3 | 2,4-dichloro-phenyl | $CH_3$ | (propyl) | (cyclopropylmethyl) | NMR($^1$H, CDCl$_3$): δ7.46(d, 1H), 7.26-7.21(dd/d, 2H), 3.64(bm, 1H), 3.50(bm, 1H), 3.35(dd, 2H), 3.17(dd, 2H), 2.67(t, 2H), 2.21(s, 3H), 2.01(m, 2H), 1.57(m, 2H), 1.03(m, 1H), 0.88 (t, 3H), 049(m, 2H), 0.17(m, 2H). MS(m/z): 405[MH]$^+$, 2Cl. |

EXAMPLE 4

Synthesis of Representative Compounds of Structure (Ib-2)

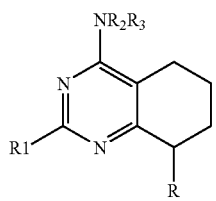

(Ib-2)

Synthesis of Representative Compounds of Structure (4-1)

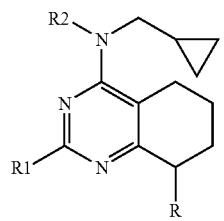

(4-1)

Representative compounds of this invention were prepared by the procedure set forth below for the compounds of general formula (4-2).

All the analytical data are set forth in the following Table 4-1.

Synthesis of Representative Compounds of Structure (4-2)

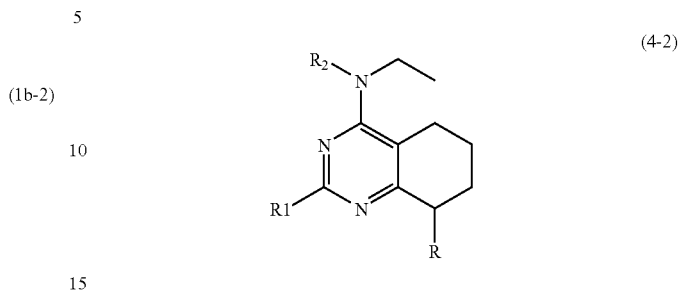

(4-2)

Butyl[8-(2,4-dichlorophenyl)-2-methyl-5,6,7,8-tetrahydro-quinazolin-4-yl]ethylamine Intermediate 40 (89 mg, 0.27 mmol) and butyl ethyl amine (0.4 mL, 10 eq) dissolved in anh. DMSO (4 mL) were heated at 100° C. (screw cap vial) for 4 h. The reaction mixture was then cooled down to r.t. and poured in EtOAc/H$_2$O. The phases were separated and the organic layer was dried over anh. Na$_2$SO$_4$. The solids were filtered, the solvent was evaporated and the crude oil was purified by flash chromatography (silica gel, toluene/acetone 97:3). The title compound was obtained as a yellow oil (25 mg, 0.06 mmol, 24%).

Compounds 4-1-1, 4-1-2, 4-2-1, 4-2-2 and 4-2-3 were prepared analogously using the appropriate amine. The chloro-pyrimidine intermediates of examples 4-1-1, 4-1-2, 4-2-1, 4-2-2 and 4-2-3 were prepared using the procedure set forth for intermediate 41, except that:

a) 2-chloro-cyclohexanone was used instead of 2-chloro-pentanone, and
b) different Grignard reagents were used:
4-1-1 and 4-2-1 (1-bromo-2,4-dimethoxybenzene),
4-1-2 and 4-2-2 (2-bromo-5-fluoro-toluene) and 4-2-3 (2-bromo-5-methyl-toluene).

TABLE 4-1

| Cpd. No. | R | R$_1$ | R$_2$— | R$_3$— | Analytical Data |
|---|---|---|---|---|---|
| 4-1-1 | 2,4-dimethoxy-phenyl | CH$_3$ | *n-propyl* | *cyclopropylmethyl* | NMR($^1$H, CDCl$_3$): δ6.47(d, 1H), 6.44 (d, 1H), 6.33(dd, 1H), 4.35(t, 1H), 3.77(s, 6H), 3.46(m, 1H), 3.40(m, 1H), 3.27(m, 2H), 2.58(m, 2H), 2.40 (s, 3H), 2.11(m, 1H), 1.78(m, 2H), 1.60(m, 3H), 1.08(m, 1H), 0.89(t, 3H), 0.51(m, 2H), 0.20(m, 2H). MS(m/z): 396[MH]$^+$. |
| 4-1-2 | 2-methyl-4-fluoro-phenyl | CH$_3$ | *n-propyl* | *cyclopropylmethyl* | NMR($^1$H, CDCl$_3$): δ6.87(dd, 1H), 6.72(td, 1H), 6.51(dd, 1H), 4.26(bt, 1H), 3.50(m, 1H), 3.40(m, 1H), 3.29 (d, 2H), 2.63(m, 2H), 2.41(s, 3H), 2.39(s, 3H), 2.18(m, 1H), 1.80(m, 1H), 1.72(m, 1H), 1.60(m, 3H) 1.09 (m, 1H), 0.91(t, 3H), 0.53(dm, 2H), 0.21(m, 2H). MS(m/z):368[MH]$^+$. |

TABLE 4-2

| Cpd. No. | R | $R_1$ | $R_2$— | $R_3$— | Analytical Data |
|---|---|---|---|---|---|
| 4-2-1 | 2,4-dimethoxyphenyl | $CH_3$ | [structure] | Et | NMR ($^1$H, $CDCl_3$): δ 6.47(d, 1H), 6.44 (d, 1H), 6.33(dd, 1H), 4.36(t, 1H), 3.76(s, 6H), 3.45-3.30(m, 4H), 2.60 (m, 2H), 2.40(s, 3H), 2.10(m, 1H), 1.70-1.60(m, 5H), 1.32(q, 2H), 1.17 (t, 3H), 0.94(t, 3H). MS(m/z): 383 $[MH]^+$. |
| 4-2-2 | 2-methyl-4-fluorophenyl | $CH_3$ | [structure] | Et | NMR ($^1$H, $CDCl_3$): δ 6.87(dd, 1H), 6.72(m, 1H), 6.51(dd, 1H), 4.25(m, 1H), 3.5-3.3(m, 4H), 2.60(m, 2H), 2.41(s, 3H), 2.39(s, 3H), 2.17(m, 1H), 1.78(m, 1H), 1.75-1.60(m, 2H), 1.60(m, 2H), 1.34(m, 2H), 1.21(t, 3H), 0.95(t, 3H). MS(m/z): 356 $[MH]^+$. |
| 4-2-3 | 2,4-dimethylphenyl | $CH_3$ | [structure] | Et | NMR ($^1$H, $CDCl_3$): δ 6.98(bs, 1H), 6.84(bd, 1H), 6.46(d, 1H), 4.25(t, 1H), 3.50(m, 1H), 3.38(m, 1H), 3.28 (m, 2H), 2.60(m, 2H), 2.38(s, 3H), 2.37(s, 3H), 2.26(s, 3H), 2.17(m, 1H), 1.82(m, 1H), 1,72(m, 1H), 1.63 (m, 3H), 1.08(m, 1H), 0.89(t, 3H), 0.51(m, 2H), 0.20(m, 2H). MS(m/z): 364 $[MH]^+$. |
| 4-2-4 | 2,4-dichlorophenyl | $CH_3$ | [structure] | Et | NMR ($^1$H, $CDCl_3$): δ 7.37(d, 1H), 7.07 (dd, 1H), 6.57(d, 1H), 4.45(t, 1H), 3.43(m, 4H), 2.59(m, 2H), 2.38(s, 3H), 2.24(m, 2H), 1.73(m, 2H), 1.6-1.5(m, 2H), 1.32(m, 2H), 1.38(t, 3H), 0.94(t, 3H). MS(m/z): 392 $[MH]^+$ (2Cl) |

EXAMPLE 5

CRF Binding Activity

CRF binding affinity has been determined in vitro by the compounds' ability to displace $^{125}$I-oCRF and $^{125}$I-Sauvagine for CRF1 and CRF2 SPA, respectively, from recombinant human CRF receptors expressed in Chinese Hamster Ovary (CHO) cell membranes. For membrane preparation, CHO cells from confluent T-flasks were collected in SPA buffer (HEPES/KOH 50 mM, EDTA 2 mM; $MgCl_2$ 10 mM, pH 7.4.) in 50 mL centrifuge tubes, homogenized with a Polytron and centrifuged (50'000 g for 5 min at 4° C.: Beckman centrifuge with JA20 rotor). The pellet was resuspended, homogenized and centrifuged as before.

The SPA experiment has been carried out in Optiplate by the addition of 100 μL the reagent mixture to 1 μL of compound dilution (100% DMSO solution) per well. The assay mixture was prepared by mixing SPA buffer, WGA SPA beads (2.5 mg/mL), BSA (1 mg/mL) and membranes (50 and 5 μg of protein/mL for CRF1 and CRF2 respectively) and 50 pM of radioligand.

The plate was incubated overnight (>18 hrs) at room temperature and read with the Packard Topcount with a WGA-SPA $^{125}$I counting protocol.

EXAMPLE 6

CRF Functional Assay

Compounds of the invention were characterised in a functional assay for the determination of their inhibitory effect. Human CRF-CHO cells were stimulated with CRF and the receptor activation was evaluated by measuring the accumulation of cAMP.

CHO cells from a confluent T-flask were resuspended with culture medium without G418 and dispensed in a 96-well plate, 25'000 c/well, 100 μL/well and incubated overnight. After the incubation the medium was replaced with 100 μL of cAMP IBMX buffer warmed at 37° C. (5 mM KCl, 5 mM $NaHCO_3$, 154 mM NaCl, 5 mM HEPES, 2.3 mM $CaCl_2$, 1 mM $MgCl_2$; 1 g/L glucose, pH 7.4 additioned by 1 mg/mL BSA and 1 mM IBMX) and 1 μL of antagonist dilution in neat DMSO. After 10 additional minutes of incubation at 37° C. in a plate incubator without CO2, 1 μL of agonist dilution in neat DMSO was added. As before, the plate was incubated for 10 minutes and then cAMP cellular content was measured by using the Amersham RPA 538 kit.

All publications, including but not limited to patents and patent applications, cited in this specification are herein incorporated by reference as if each individual publication were specifically and individually indicated to be incorporated by reference herein as though fully set forth.

It is to be understood that the present invention covers all combinations of particular and preferred groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A compound of formula (I) and stereoisomers, prodrugs and pharmaceutically acceptable salts thereof

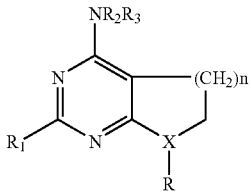

wherein
R is aryl or heteroaryl, each of which may be substituted by 1 to 4 groups selected from: halogen, C1-C6 alkyl, C1-C6 alkoxy, halo C1-C6 alkyl, C2-C6 alkenyl, C2-C6 alkynyl, halo C1-C6 alkoxy, —COR$_4$, nitro, —NR$_9$R$_{10}$ cyano, and a group R$_5$;
R$_1$ is hydrogen, C1-C6 alkyl, C2-C6 alkenyl, C2-C6 alkynyl, halo C1-C6 alkyl, halo C1-C6 alkoxy, halogen, NR$_9$R$_{10}$ or cyano;
R$_2$ and R$_3$ together with N form a saturated or unsaturated heterocycle, which may be substituted by 1 to 3 R$_7$ groups; or
R$_2$ and R$_3$ together with N form a 5-10 membered heteroaryl group, in which the 5-membered heteroaryl group contains at least one heteroatom selected from oxygen, sulphur or nitrogen and the 6-10 membered heteroaryl group contains from 1 to 3 nitrogen atoms and wherein said 5-10 membered heteroaryl may be substituted by 1 to 3 R$_7$ groups;
R$_4$ is a C1-C4 alkyl, —OR$_9$ or —NR$_9$R$_{10}$;
R$_5$ is a 5-6 membered heterocycle, which may be saturated or may contain one to three double bonds, and which may be substituted by 1 or more R$_8$ groups;
R$_6$ is a C1-C6 alkyl that may be substituted by one or more groups selected from: C3-C7 cycloalkyl, C1-C6 alkoxy, haloC1-C6 alkoxy, hydroxy, and haloC1-C6 alkyl;
R$_7$ is a group R$_5$, a group R$_6$, C3-C7 cycloalkyl, C1-C6 alkoxy, hydroxy, halogen, nitro, cyano, C(O)NR$_9$R$_{10}$, or phenyl which may be substituted by 1 to 4 R$_8$ groups;
R$_8$ is C1-C6 alkyl, halo C1-C2 alkyl, halogen, nitro, C1-C6 alkoxy or cyano;
R$_9$ is hydrogen or C1-C6 alkyl;
R$_{10}$ is hydrogen or C1-C6 alkyl;
X is nitrogen; and
n is 1.

2. A compound, according to claim 1, in which the group NR$_2$R$_3$ represents a 5-6 membered heterocycle.

3. A compound, according to claim 2, of formula (1-10)

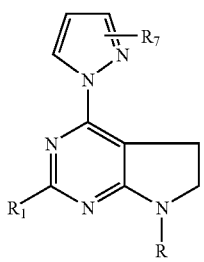

in which R, R$_1$, and R$_7$ are defined as in claim 1.

4. A compound, according to claim 1 wherein R$_1$ is C1-C3 alkyl group or halo C1-C3 alkyl group.

5. A compound, according to claim 1 wherein R is an aryl group selected from: 2,4-dichlorophenyl, 2-chloro-4-methylphenyl, 2-chloro-4-trifluoromethylphenyl, 2-chloro-4-methoxyphenyl, 2,4,5-trimethylphenyl, 2,4-dimethylphenyl, 2-methyl-4-methoxyphenyl, 2-methyl-4-chlorophenyl, 2-methyl-4-trifluoromethylphenyl, 2,4-dimethoxyphenyl, 2-methoxy-4-trifluoromethylphenyl, 2-methoxy-4-chlorophenyl, 3-methoxy-4-chlorophenyl, 2,5-dimethoxy-4-chlorophenyl, 2-methoxy-4-isopropylphenyl, 2-methoxy-4-trifluoromethylphenyl, 2-methoxy-4-isopropylphenyl, 2-methoxy-4-methylphenyl, 2-trifluoromethyl-4-chlorophenyl, 2,4-trifluoromethylphenyl, 2-trifluoromethyl-4-methylphenyl, 2-trifluoromethyl-4-methoxyphenyl, 2-bromo-4-isopropylphenyl, 4-methyl-6-dimethylaminopyridin-3-yl, 3,5-dichloro-pyridin-2-yl, 2,6-bismethoxy-pyridin-3-yl and 3-chloro-5-tricloromethyl-pyridin-2-yl.

6. A compound, according to claim 1 selected in a group consisting of:
7-(2,4-dichlorophenyl)-4-(2-ethyl-piperidin-1-yl)-2-methyl-6,7-dihydro-5H-pyrrolo[2,3-d]pyrimidine;
7-(2,4-dichlorophenyl)-4-[(2R,5R)-2,5-dimethylpyrrolidin-1-yl]-2-methyl-6,7-dihydro-5H-pyrrolo[2,3-d]pyrimidine;
7-(2,4-dichlorophenyl)-2-methyl-4-(3-thiazol-2-yl-pyrazol-1-yl)-6,7-dihydro-5-H-pyrrolo[2,3-d]pyrimidine;
7-(2,4-bis-trifluoromethylphenyl)-2-methyl-4-(3-thiazol-2-yl-pyrazol-1-yl)-6,7-dihydro-5H-pyrrolo[2,3-d]pyrimidine;
7-(2-bromo-4-isopropylphenyl)-2-methyl-4-(3-trifluoromethyl-pyrazol-1-yl)-6,7-dihydro-5H-pyrrolo[2,3-d]pyrimidine; 7-(2,4-dichlorophenyl)-4-(5-isopropyl-3-trifluoromethyl-pyrazol-1-yl)-2-methyl-6,7-dihydro-5H-pyrrolo[2,3-d]pyrimidine and 7-(2,4-dichlorophenyl)-4-(3-isopropyl-5-trifluoromethyl-pyrazol-1-yl)-2-methyl-6,7-dihydro-5H-pyrrolo[2,3-d]pyrimidine;
7-(2,4-dichlorophenyl)-4-(3-ethyl-5-trifluoromethylpyrazol-1-yl)-2-methyl-6,7-dihydro-5H-pyrrolo[2,3-d]pyrimidine;
7-(2,4-dichlorophenyl)-4-(3,5-dimethylpyrazol-1-yl)-2-methyl-6,7-dihydro-5H-pyrrolo[2,3-d]pyrimidine;
7-(2,4-dichlorophenyl)-4-(3-dimethoxymethyl-pyrazol-1-yl)-2-methyl-6,7-dihydro-5H-pyrrolo[2,3-d]pyrimidine;
7-(2,4-dichlorophenyl)-4-(3-ethyl-5-trifluoromethylpyrazol-1-yl)-2-methyl-6,7-dihydro-5H-pyrrolo[2,3-d]pyrimidine;
4-(4-bromo-3-methyl-pyrazol-1-yl)-7-(2,4-dichlorophenyl)-2-methyl-6,7-dihydro-5H-pyrrolo[2,3-d]pyrimidine; 4-(4-bromopyrazol-1-yl)-7-(2,4-dichlorophenyl)-2-methyl-6,7-dihydro-5H-pyrrolo[2,3-d]pyrimidine;
7-(2,4-dichlorophenyl)-4-[3-(4-chlorophenyl)-pyrazol-1-yl]-2-methyl-6,7-dihydro-5H-pyrrolo[2,3-d]pyrimidine;
7-(2,4-dichlorophenyl)-4-[3-(2-nitrophenyl)-pyrazol-1-yl]-2-methyl-6,7-dihydro-5H-pyrrolo[2,3-d]pyrimidine;
7-(2,6-dimethoxy-pyridin-3-yl)-2-methyl-4-(3-thiazol-2-yl-pyrazol-1-yl)-6,7-dihydro-5H-pyrrolo[(2,3-d)]pyrimidine;
7-(2,4-bis-trifluoromethyl-phenyl)-2-methyl-4-(3-morpholyn-4-yl-pyrazol-1-yl)-6,7-dihydro-5H-pyrrolo[(2,3-d)]pyrimidine;
7-(2,4-bis-trifluoromethyl-phenyl)-2-methyl-4-(3-pyridin-3-yl-pyrazol-1-yl)-6,7-dihydro-5H-pyrrolo[(2,3-d)]pyrimidine;
7-(2,4-bis-trifluoromethyl-phenyl)-2-methyl-4-(3-pyrazin-2-yl-pyrazol-1-yl)-6,7-dihydro-5H-pyrrolo[(2,3-d)]pyrimidine; and
7-(2,4-bis-trifluoromethyl-phenyl)-2-methyl-4-(3-oxalol-5-yl-pyrazol-1-yl)-6,7-dihydro-5H-pyrrolo(2,3-d)pyrimidine.

7. A process for the preparation of a compound of formula (I) as claimed in claim 1, which comprises the reaction of a compound of formula (II), wherein L is a leaving group,

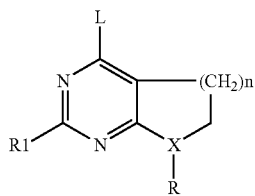

(II)

with the amino compound R₂R₃NH (III), wherein R, R₂ and R₃ are defined as in claim 1, followed where necessary or desired by isolation of the compound as the salt thereof.

8. A process, according to claim 7, for preparing compounds of formula (IIa),

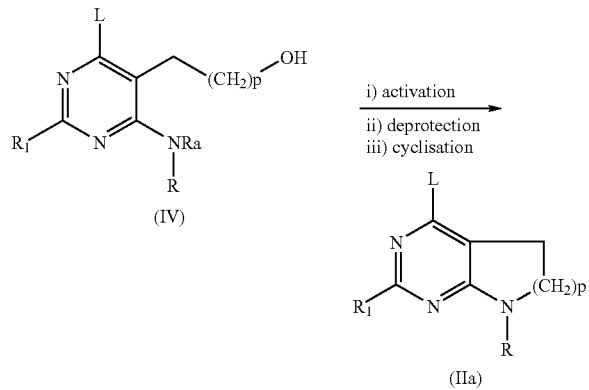

which are equivalent to compounds of formula (II) wherein X is nitrogen, comprising the following steps:

i) activation of the hydroxy group of compounds of formula (IV), wherein p is 1, Ra is a suitable protecting group for the amino group, R and $R_1$ are defined as in claim 1, by conversion into a suitable leaving group;

ii) deprotection of the amino protecting group; and iii) cyclisation.

9. A pharmaceutical composition comprising a compound according to claim 1, in admixture with one or more physiologically acceptable carriers or excipients.

10. A method for the treatment of a condition mediated by CRF (corticotropin-releasing factor), wherein the condition is depression, comprising administration, to a mammal in need of treatment thereof, of an effective amount of a compound according to claim 1.

11. A method for the treatment of a condition mediated by CRF (corticotropin-releasing factor), wherein the condition is IBS (irritable bowel syndrome, comprising administration, to a mammal in need of treatment thereof, of an effective amount of a compound according to claim 1.

12. A method for the treatment of a condition mediated by CRF (corticotropin-releasing factor), wherein the condition is anxiety, comprising administration, to a mammal in need of treatment thereof, of an effective amount of a compound according to claim 1.

* * * * *